United States Patent
Sharma et al.

(10) Patent No.: US 12,084,416 B2
(45) Date of Patent: Sep. 10, 2024

(54) SUBSTITUTED SULFONYLUREA DERIVATIVES

(71) Applicant: Zydus Lifesciences Limited, Gujarat (IN)

(72) Inventors: Rajiv Sharma, Gujarat (IN); Sameer Agarwal, Gujarat (IN)

(73) Assignee: Zydus Lifesciences Limited, Gujarat (IN)

( * ) Notice: Subject to any disclaimer, the term of this patent is extended or adjusted under 35 U.S.C. 154(b) by 415 days.

(21) Appl. No.: 17/422,500

(22) PCT Filed: Jan. 13, 2020

(86) PCT No.: PCT/IB2020/050216
§ 371 (c)(1),
(2) Date: Jul. 13, 2021

(87) PCT Pub. No.: WO2020/148619
PCT Pub. Date: Jul. 23, 2020

(65) Prior Publication Data
US 2022/0169605 A1 Jun. 2, 2022

(30) Foreign Application Priority Data
Jan. 14, 2019 (IN) .............................. 201921001555

(51) Int. Cl.
| | | |
|---|---|---|
| C07D 207/48 | (2006.01) |
| C07D 205/04 | (2006.01) |
| C07D 207/08 | (2006.01) |
| C07D 211/24 | (2006.01) |
| C07D 211/96 | (2006.01) |
| C07D 401/04 | (2006.01) |
| C07D 403/04 | (2006.01) |
| C07D 403/06 | (2006.01) |
| C07D 405/04 | (2006.01) |
| C07D 405/06 | (2006.01) |
| C07D 409/04 | (2006.01) |
| C07D 409/06 | (2006.01) |
| C07D 409/12 | (2006.01) |
| C07D 417/04 | (2006.01) |
| C07D 417/06 | (2006.01) |

(52) U.S. Cl.
CPC ......... *C07D 207/48* (2013.01); *C07D 205/04* (2013.01); *C07D 207/08* (2013.01); *C07D 211/24* (2013.01); *C07D 211/96* (2013.01); *C07D 401/04* (2013.01); *C07D 403/04* (2013.01); *C07D 403/06* (2013.01); *C07D 405/04* (2013.01); *C07D 405/06* (2013.01); *C07D 409/04* (2013.01); *C07D 409/06* (2013.01); *C07D 409/12* (2013.01); *C07D 417/04* (2013.01); *C07D 417/06* (2013.01)

(58) Field of Classification Search
CPC .. C07D 207/48; C07D 205/04; C07D 207/08; C07D 211/24; C07D 211/96; C07D 401/04; C07D 403/04; C07D 403/06; C07D 405/04; C07D 405/06; C07D 409/04; C07D 409/06; C07D 409/12; C07D 417/04; C07D 417/06; C07D 209/10; C07D 307/10; C07D 309/04; C07D 401/06; C07D 401/12; C07D 211/18
See application file for complete search history.

(56) References Cited

U.S. PATENT DOCUMENTS

| | | |
|---|---|---|
| 2,979,437 A | 4/1961 | Laubach et al. |
| 6,147,115 A | 11/2000 | Crowell et al. |

FOREIGN PATENT DOCUMENTS

| | | | |
|---|---|---|---|
| GB | 1473200 A | * 5/1977 | ........... C07D 211/02 |
| WO | WO-1998/032733 A1 | 7/1998 | |
| WO | WO-2001/019390 A1 | 3/2001 | |
| WO | WO-2014/190015 A1 | 11/2014 | |
| WO | WO-2016/123229 A1 | 8/2016 | |
| WO | WO-2016/131098 A1 | 8/2016 | |

(Continued)

OTHER PUBLICATIONS

Chemical Abstracts Registry No. 1821760-52-4, indexed in the Registry file on STN CAS Online Dec. 3, 2015. (Year: 2015).*

(Continued)

*Primary Examiner* — Laura L Stockton
(74) *Attorney, Agent, or Firm* — Goodwin Procter LLP

(57) ABSTRACT

The present invention relates to novel heterocyclic compounds of the general formula (I) their pharmaceutically acceptable salts, pharmaceutically acceptable solvates, enantiomers, diastereomers and polymorphs. The invention also relates to processes for the preparation of the compounds of invention, pharmaceutical compositions containing the compounds and their use as the compounds of the invention belong to the family of NOD-like receptor family (NLR) protein NLRP3 modulators. The present invention thus relates to novel NLRP3 modulators as well as to the use of the novel inhibitor compounds in the treatment of diseases or conditions in which interleukin 1β activity is implicated.

Formula (I)

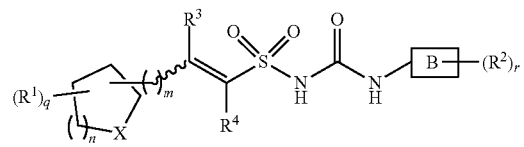

13 Claims, No Drawings

(56) References Cited

FOREIGN PATENT DOCUMENTS

| WO | WO-2017/017469 A1 | 2/2017 |
|----|-------------------|--------|
| WO | WO-2017/031161 A1 | 2/2017 |
| WO | WO-2017/079352 A2 | 5/2017 |
| WO | WO-2017/129897 A1 | 8/2017 |
| WO | WO-2017/140778 A1 | 8/2017 |
| WO | WO-2017/184623 A1 | 10/2017 |
| WO | WO-2018/225018 A1 | 12/2018 |
| WO | WO-2019/008029 A1 | 1/2019 |
| WO | WO-2019/023147 A1 | 1/2019 |
| WO | WO-2019/043610 A1 | 3/2019 |
| WO | WO-2019/068772 A1 | 4/2019 |
| WO | WO-2020/148619 A1 | 7/2020 |

OTHER PUBLICATIONS

Dinarello et al. (2012) "Treating inflammation by blocking interleukin-1 in a broad spectrum of diseases," Nature Review Drug Discovery 11:633-652.

Guo et al. (2015) "Inflammasomes: mechanism of action, role in disease, and therapeutics," Nature Medicine 21:677-687.

Ising et.al. (2019) "NLRP3 inflammasome activation drives tau pathology," Nature 669-673 24 pages.

Lamkanfi et al. (2014) "Mechanisms and Functions of Inflammasomes," Cell 157:1013-1022.

Latz et al. (2013) "Activation and regulation of the inflammasomes," Nature Reviews Immunology 13:397-341.

Masters et al. (2009) "Horror Autoinflammaticus: The Molecular Pathophysiology of Autoinflammatory Disease," Annu. Rev. Immunol. 27:621-668.

Mridha et al. (2017) "NLRP3 inflammasome blockade reduces liver inflammation and fibrosis in experimental NASH in mice," Journal of Hepatology 66(5) 30 pages.

Strowig et al. (2013) "Inflammasomes in health and disease," Nature 481:278-286.

Wen et al. (2013) "Mechanisms of NOD-like Receptor-Associated Inflammasome Activation," Immunity 39:432-441.

* cited by examiner

SUBSTITUTED SULFONYLUREA DERIVATIVES

CROSS-REFERENCE TO RELATED APPLICATIONS

This application is a U.S. national stage patent application under 35 U.S.C. § 371 of International Application No. PCT/IB2020/050216, filed on Jan. 13, 2020, which application claims the benefit of and priority to Indian Patent Application No. 201921001555, filed on Jan. 14, 2019.

FIELD OF THE INVENTION

The present invention relates to novel heterocyclic compounds of the general formula (I) their pharmaceutically acceptable salts, pharmaceutically acceptable solvates, enantiomers, diastereomers and polymorphs. The invention also relates to processes for the preparation of the compounds of invention, pharmaceutical compositions containing the compounds and their use as the compounds of the invention belong to the family of NOD-like receptor family (NLR) protein NLRP3 modulators. The present invention thus relates to novel NLRP3 modulators as well as to the use of the novel inhibitor compounds in the treatment of diseases or conditions in which interleukin 1β activity is implicated.

BACKGROUND OF THE INVENTION

The NOD-like receptor family (NLR) protein NLRP3 is an intracellular signaling molecule that senses many pathogens, environmental and host-derived factors. (Wen., et. al., Immunity. 2013; 39:432-441). Activation of NLRP3 leads to binding with apoptosis associated speck-like protein containing a CARD (ASC). ASC in turn interacts with the cysteine protease caspase-1, forming a complex termed the inflammasome. This results in the activation of caspase-1, which cleaves the pro-inflammatory cytokines IL-1β and IL-18 to their active forms and mediates a type of inflammatory cell death known as pyroptosis. Other intracellular pattern recognition receptors (PRRs) are also capable of forming inflammasomes. These include other NLR family members such as NLRP1 and NLRC4 and non-NLR PRRs such as the double-stranded DNA (dsDNA) sensors absent in melanoma 2 (AIM2) and interferon, gamma inducible protein 16 (IFI16) (Latz, et. al., Nat Rev Immunol. 2013; 13:397-411). NLRP3-dependent IL-1β processing can also be activated by an indirect, non-canonical pathway downstream of caspase-1 (Lamkanfi, et. al., Cell. 2014; 157:1013-1022).

Inflammasome components such as NLRP3, ASC and caspase-1 are expressed in immune cells in the liver including Kupffer cells, infiltrating macrophages, hepatocytes, and hepatic stellate cells. Inflammasome activation is dependent on two successive signals. Signal 1 is driven by TLR and IL-AR signaling, includes expression of component proteins including NLRP3, ASC, pro-caspase-1, pro-IL-1β, and pro-IL-18. Signal 2 is provided by danger signals (DAMPS) that during NASH development are mainly released by stressed or dying hepatocytes or via a "leaky" gut (PAMPs). This process leads to oligomerization of the inflammasome components and cleavage of pro-caspase-1, leading to the release of active pro-inflammatory cytokines.

The NLRP3 inflammasome acts as a key mediator of inflammatory responses through the activation of caspase-1 leading to processing and release of the pro-inflammatory cytokines interleukin-1β (IL-1β) and interleukin-18 (IL-18). The NLRP3 inflammasome is a component of the inflammatory process and its aberrant activation is pathogenic in inherited disorders such as the rare periodic fever syndrome, cryopyrin associated periodic syndromes (CAPS), Tumor necrosis factor receptor-associated periodic syndrome (TRAPS) and complex diseases such as multiple sclerosis, Inflammatory bowel disease (IBD), type 2 diabetes, atherosclerosis, asthma, gouty arthritis, and inflammatory central nervous system (CNS) diseases including Parkinson's, Alzheimer's and other brain diseases. (Masters, et. al., Annu Rev Immunol. 2009; 27:621-668; Strowig, et. al., Nature 2012, 481, 278-286; Guo, et. al., Nat. Med. 2015, 21, 677; Ising, et. al., Nature 2019, 575, 669-673.)

Inflammation is an essential host response to infection and injury. The regulation of the pro-inflammatory cytokine interleukin-1β (IL-1β), which is central to host responses to infection, also causes tissue injury when activated inappropriately. (Dinarello, et. al., Nat. Rev. Drug Discovery 2012, 11, 633-652.) NLRP3 inflammasome activation plays a key role in each of the components including induction of pro-inflammatory signaling, hepatocellular injury and cell death, and activation of the hepatic stellate cells (HSC) that are responsible for collagen deposition and liver fibrosis. In particular, the transition from NAFLD to NASH associates with NLRP3-inflammasome activation and an increased expression of inflammasome-related components, including apoptosis-associated speck-like protein containing a carboxy-terminal CARD (ASC), caspase-1 (CASP-1) and pannexin. (Mridha, et. al., Journal of Hepatology, 2017, 66 (5), 1037-1046)

Current treatments for NLRP3 related diseases include biologic agents that target IL-1. These are the recombinant IL-1 receptor antagonist Anakinra, the neutralizing IL-1β antibody Canakinumab and the soluble decoy IL-1 receptor Rilonacept.

Wipo patent application WO98/32733, WO2001/019390, WO2014/190015, WO2016/123229 WO2016/131098 disclosed sulfonylureas derivatives and related compounds as NLRP3 inflammasome inhibitors. WO2017/017469 disclosed certain cyclic diarylboron derivatives as NLRP3 inflammasome inhibitors for the treatment of diseases or conditions in which interleukin 1β activity is implicated. Some of the recent patent applications such as WO2017/031161, WO2017/079352, WO2017/129897, WO2017/184623, WO2018/225018, WO2019/043610, WO2019/023147, WO2019/008029, WO2019/068772 also disclosed certain class of compounds as NLRP3 inhibitors.

We herein disclose novel heterocyclic compounds of general formula (I) which are NLRP3 modulators for the prevention and treatment of disease states mediated by NLRP3 or conditions in which interleukin 1β activity is implicated, including inflammation, Cryopyrin-associated periodic syndrome (CAPS), gouty arthritis, multiple sclerosis, Inflammatory bowel disease (IBD), type 2 diabetes, atherosclerosis, liver fibrosis inflammatory central nervous system (CNS) diseases like Parkinson's, Alzheimer's and other brain diseases, mediated via NLRP3 pathway. More particularly, embodiments of the present invention are useful as therapeutics in the treatment of a variety of pathological conditions including (but not limited to) lymphoma, autoimmune diseases, heteroimmune diseases, inflammatory diseases, cancer, and neurodegenerative diseases or conditions.

SUMMARY OF THE INVENTION

The present invention discloses heterocyclic compounds as defined by the general formula (I) that are NLRP3 modulators for the prevention and treatment of disease states mediated by NLRP3 as well as treatment of diseases or conditions in which interleukin 1β activity is implicated. The compounds of the present invention are useful in the treatment of human or animal body, by inhibition of NLRP3. The compounds of this invention are therefore suitable for the prevention and treatment of disease states mediated by NLRP3.

EMBODIMENT(S) OF THE INVENTION

An embodiment of the present invention provides novel heterocyclic compounds represented by the general formula (I), their tautomeric forms, their enantiomers, their diastereoisomers, their stereoisomers, their pharmaceutically acceptable salts and pharmaceutical compositions containing them or their mixtures thereof.

In an another embodiment of the present invention is provided pharmaceutical compositions containing compounds of the general formula (I), their tautomeric forms, their enantiomers, their diastereoisomers, their stereoisomers, their pharmaceutically acceptable salts, or their mixtures in combination with suitable carriers, solvents, diluents and other media normally employed in preparing such compositions.

In a further embodiment is provided the use of heterocyclic compounds of the present invention as NLRP3 modulators, by administering a therapeutically effective and non-toxic amount of compounds of general formula (I) or their pharmaceutically acceptable compositions to the mammals.

In a still further embodiment compound of formula (I) of the present invention may be used in combination with one or more suitable pharmaceutically active agents.

In another further embodiment is provided a process for preparing the novel compounds of the present invention.

A further objective of the present invention is to provide novel intermediates involved in the process.

A further objective of the present invention to provide process for the preparation of intermediates involved in the process.

DESCRIPTION OF THE INVENTION

Accordingly, the present invention relates to the compounds of the general formula (I)

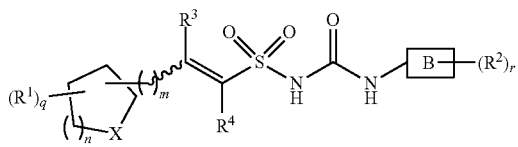

Formula (I)

their tautomeric forms, their stereoisomers, their enantiomers, their pharmaceutically acceptable salts, and pharmaceutical compositions containing them wherein, $R^1$ at each occurrence independently represents hydrogen, halogen, haloalkyl, cyano, optionally substituted groups selected from $(C_1-C_6)$alkyl, $(C_1-C_6)$haloalkyl, $(C_2-C_6)$alkenyl, $(C_1-C_6)$alkoxy, $(C_3-C_7)$cycloalkyl, $NH_2$, $NH(C_1-C_6)$alkyl, $N(C_3-C_7)$cycloalkyl; $N(C_1-C_6$ alkyl$)_2$, aryl, heteroaryl, heterocyclyl, benzyl, thiol, mercapto alkyl, $SO_2(C_1-C_6)$alkyl, $(C_1-C_6)$thio-alkoxy, amide;

m and n is independently selected from integer 0-3;
q and r is independently selected from integer 1-4;
X is N—$R^5$; O, S, $SO_2$;
$R^5$ at each occurrence independently represents hydrogen, halogen, haloalkyl, cyano, optionally substituted groups selected from $(C_1-C_6)$alkyl, $(C_1-C_6)$haloalkyl, $(C_2-C_6)$alkenyl, $(C_2-C_6)$alkynyl, $(C_1-C_6)$alkoxy, $(C_3-C_7)$cycloalkyl, $(C_1-C_6)$alkylSO$_2(C_1-C_6)$alkyl, $(C_1-C_6)$alkylN$(C_1-C_6)$alkyl, $(C_1-C_6)$alkylN$(C_3-C_7)$cycloalkyl, aryl, heteroaryl, heterocyclyl, benzyl, tert-butyloxycarbonyl, thiol, mercaptoalkyl, $SO_2(C_1-C_6)$alkyl, $SO_2(C_3-C_7)$cycloalkyl, $SO_2$-aryl, $SO_2$-heterocyclyl, $(C_1-C_6)$thioalkyl, $(C_1-C_6)$thioalkoxy, $(C_1-C_6)$alkylSO$_2$NH$_2$, —CONH$_2$, —CO(C$_1$-C$_6$)alkyl, —CO(C$_1$-C$_6$)haloalkyl, —CO-aryl, —CO-heteroaryl, —CO— heterocyclyl, 4- to 7-membered heterocyclic ring, 7- to 14-membered bicyclic heterocyclic ring system, bridged or spiro ring system having optionally one or more than one heteroatoms;

$R^2$ at each occurrence independently represents hydrogen, halogen, haloalkyl, cyano, optionally substituted groups selected from $(C_1-C_6)$alkyl, $(C_1-C_6)$alkoxy, $(C_2-C_6)$alkenyl, $(C_3-C_7)$cycloalkyl, benzyl, aryl, heteroaryl, heterocyclyl, thiol, thioalkyl, thio-alkoxy, $SO_2(C_1-C_6)$alkyl, $SO(C_1-C_6)$alkyl, bridged or spiro ring system having optionally one or more than one heteroatoms;

Each of $R^3$ and $R^4$ at each occurrence represents hydrogen, halogen, haloalkyl, cyano, nitro, amide, sulphonamide, acyl, hydroxyl, optionally substituted groups selected from $(C_1-C_6)$alkyl, $(C_1-C_6)$haloalkyl, $(C_3-C_6)$cycloalkyl, $(C_1-C_6)$alkoxy, $SO_2(C_1-C_6)$alkyl, thiol, mercapto alkyl benzyl, aryl, heteroaryl, heterocyclyl;
Alternatively $R_3$, and $R_4$ forms a bond;
'B' is selected from the following ring system

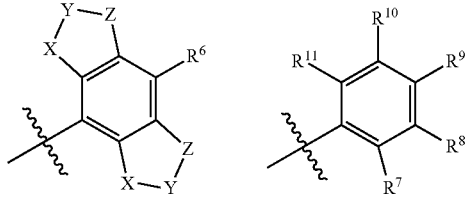

Where in W, Y, Z at each occurrence independently represents C, N, S, $SO_2$, and O, which may be optionally substituted;

Each of $R^6$, $R^7$, $R^8$, $R^9$, $R^{10}$ and $R^{11}$ at each occurrence are independently selected from hydrogen, halogen, cyano, amide, sulphonamide, acyl, hydroxyl, optionally substituted groups selected from $(C_1-C_6)$alkyl, $(C_1-C_6)$haloalkyl, $(C_3-C_6)$cycloalkyl, $(C_1-C_6)$alkoxy, benzyl, aryl, heteroaryl, heterocyclyl; Alternatively each of $R^7$ and $R^8$, $R^8$ and $R^9$, $R^9$ and $R^{10}$ and $R^{10}$ and $R^{11}$ wherever possible, together may form a 4 to 7 membered saturated or partially saturated ring containing from 0-2 additional heteroatoms selected from the group consisting of N, O, and $S(O)_p$; p=1-2.

When any of above defined group is substituted the substitutions on them may be selected from those described above or may be selected from hydrogen, hydroxy, cyano, halo, haloalkyl, haloalkyloxy, alkylthio $(C_1-C_6)$alkyl, $(C_2-C_6)$alkenyl, $(C_2-C_6)$alkynyl, $(C_3-C_7)$cycloalkyl, $C_1-C_6$ alkoxy, aryl, heterocyclyl, heteroaryl, —COR$_{12}$, —CSR$_{12}$, C(O)OR$_{12}$, C(O)—R$_{12}$, —C(O)—NR$_{12}$R$_{13}$, —C(S)—NR$_{12}$R$_{13}$, —SO$_2$R$_{12}$ group, wherein each of R$_{12}$ and R$_{13}$ is independently selected from hydrogen, optionally substituted group selected from $(C_1-C_6)$alkyl, $(C_2-C_6)$alkenyl, $(C_2-C_6)$alkynyl, $(C_3-C_7)$cycloalkyl, aryl, heteroaryl, heterocyclyl groups;

In a preferred embodiment $R^1$ at each occurrence independently represents hydrogen, halogen, haloalkyl optionally substituted groups selected from $(C_1-C_6)$alkyl;

In a preferred embodiment $R^2$ at each occurrence independently represents hydrogen, halogen, haloalkyl, optionally substituted groups selected from $(C_1-C_6)$alkyl;

In a preferred embodiment Each of $R^3$ and $R^4$ at each occurrence independently represents hydrogen, halogen, haloalkyl, optionally substituted groups selected from $(C_1-C_6)$alkyl.

In a preferred embodiment each of $R^6$, $R^7$, $R^8$, $R^9$. $R^{10}$ and $R^{11}$ at each occurrence independently selected from hydrogen, halogen optionally substituted groups selected from $(C_1-C_6)$alkyl, $(C_1-C_6)$haloalkyl;

In a preferred embodiment, the groups, radicals described above may be selected from:

"Alkyl", as well as other groups having the prefix "alk", such as alkoxy and alkanoyl, means a carbon chain which may further be substituted with an oxygen atom as is well understood by a skilled artisan, which may further be either linear or branched, and combinations thereof, unless the carbon chain is defined otherwise. Examples of alkyl group include but not limited to methyl, ethyl, propyl, isopropyl, butyl, sec-butyl, tert.-butyl, pentyl, hexyl etc. Where the specified number of carbon atoms permits e.g. from $C_{3-10}$, the term alkyl also includes cycloalkyl groups, and combinations of linear or branched alkyl chains combined with cycloalkyl structures. When no number of carbon atoms is specified, $C_{1-6}$ is intended. Substituted alkyl includes alkyl substituted with one or more moieties selected from the group consisting of halo (e.g., CI, F, Br, and I); halogenated alkyl (e.g., $CF_3$, 2-Br-ethyl, $CH_2F$, $CH_2CI$, $CH_2CF_3$, or $CF_2CF_3$); hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate as well as those described under the definition of 'Optionally substituted'.

"Alkenyl" means carbon chains which contain at least one carbon-carbon double bond, and which may be linear or branched or combinations thereof, unless the carbon chain is defined otherwise. Examples of alkenyl include but not limited to vinyl, allyl, isopropenyl, hexenyl, pentenyl, heptenyl, 1-propenyl, 2-butenyl, 2-methyl-2-butenyl etc. Where the specified number of carbon atoms permits, e.g., from $C_{5-10}$, the term alkenyl also includes cycloalkenyl groups and combinations of linear, branched and cyclic structures. When no number of carbon atoms is specified, $C_{2-6}$) is intended.

"Alkynyl" means carbon chains which contain at least one carbon-carbon triple bond, and which may be linear or branched or combinations thereof. Examples of alkynyl include ethynyl, propargyl, 3-methyl-1-pentynyl etc. When no number of carbon atoms is specified, is intended.

the "thioalkyl" group used either alone or in combination with other radicals, denotes an alkyl group, as defined above, attached to a group of formula —SR', (sulfur and its oxidized forms) where R' represents hydrogen, alkyl or aryl group, e.g. thiomethyl, methylthiomethyl, phenylthiomethyl and the like, which may be optionally substituted.

As used herein, "carbocycle" or "carbocyclic residue" is intended to mean any stable monocyclic or bicyclic or tricyclic ring, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). In a broader perspective, the term carbocycle is intended to include, wherever applicable, the groups representing cycloalkyl, phenyl and other saturated, partially saturated or aromatic residues;

The terms "cycloalkyl" and "cycloalkenyl" refers to optionally substituted, saturated and unsaturated monocyclic, bicyclic or tricyclic carbon groups. Where appropriate, the cycloalkyl or cycloalkenyl group may have a specified number of carbon atoms, for example, $C_3-C_6$ cycloalkyl or cycloalkenyl includes within its scope a carbocyclic group having 3, 4, 5 or 6 carbon atoms. Examples of such substituents may be selected from the group consisting of cyclopropyl, cyclobutyl, cyclopentyl, cyclopentenyl, cyclohexyl, cyclohexenyl, cyclohexadienyl and the like. Substituted cycloalkyl or cycloalkenyl includes substitutions with one or more moieties selected from the group consisting of halo (e.g., CI, F, Br, and I); halogenated alkyl (e.g., $CF_3$, 2-Br-ethyl, $CH_2F$, $CH_2CI$, $CH_2CF_3$, or $CF_2CF_3$); hydroxyl; amino; carboxylate; carboxamido; alkylamino; arylamino; alkoxy; aryloxy; nitro; azido; cyano; thio; sulfonic acid; sulfate; phosphonic acid; phosphate; and phosphonate as well as those described under the definition of 'Optionally substituted'.

The "alkoxy" refers to the straight or branched chain alkoxides of the number of carbon atoms specified.

"Aryl" means a mono- or polycyclic aromatic ring system containing carbon ring atoms. The preferred aryls are monocyclic or bicyclic 6-10 membered aromatic ring systems. Phenyl and naphthyl are preferred aryls.

"Heterocyclyl" means a saturated, partially saturated or unsaturated aromatic or non-aromatic mono, bi or tricyclic radicals, containing one or more heteroatoms selected from nitrogen, sulfur and oxygen, further optionally including the oxidized forms of sulfur, namely SO & $SO_2$. Heterocyclyl systems may be attached to another moiety via any number of carbon atoms or heteroatoms of the radical and may be both saturated and unsaturated. Examples of heterocycles include tetrahydrofuran (THF), dihydrofuran, 1,4-dioxane, morpholine, 1,4-dithiane, piperazine, piperidine, 1,3-dioxolane, imidazoline, imidazolidine, pyrrolidine, pyrroline, tetrahydropyran, tetrahydro-2H-thiopyran, dihydropyran, oxathiolane, dithiolane, 1,3-dioxane, 1,3-dithiane, oxathiane, thiomorpholine, etc. The term "heterocycloalkyl" refers to a heterocyclic group as defined above connected to an alkyl group as defined above;

"Heteroaryl" means an aromatic or partially aromatic heterocycle that contains at least one ring heteroatom selected from O, S and N. Heteroaryls thus include heteroaryls fused to other kinds of rings, such as aryls, cycloalkyls, and heterocycles that are not aromatic. Examples of heteroaryl groups include; pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furyl, triazinyl, thienyl, pyrimidyl, benzisoxazolyl, benzoxazolyl, benzthiazolyl, benzothiadiazolyl, dihydrobenzofuranyl, indolinyl, pyridazinyl, indazolyl, isoindolyl, dihydrobenzothienyl, indolinyl, pyridazinyl, indazolyl, isoindolyl, dihydrobenzothienyl, indolizinyl, cinnolinyl, phthalazinyl, quinazolinyl, napthyridinyl, carbazolyl, benzodioxolyl, quinoxalinyl, purinyl, furazanyl, isobenzylfuranyl, benzimidazolyl, benzofuranyt, benzothienyl, quinolyl, indolyl, isoquinolyl, dibenzofuranyl etc. For heterocyclyl and heteroaryl groups, rings and ring systems containing from 3-15 carbon atoms are included, forming 1-3 rings.

The term "haloalkyl" means an alkyl structure in which at least one hydrogen is replaced with a halogen atom. In certain embodiments in which two or more hydrogen atoms are replaced with halogen atoms, the halogen atoms are all the same as one another.

the "haloalkoxy" group is selected from suitable haloalkyl, as defined above, directly attached to an oxygen atom, more preferably groups selected from fluoromethoxy, chloromethoxy, fluoroethoxy, chloroethoxy and the like;

In certain other embodiment in which two or more hydrogen atoms are replaced with halogen atoms, the halogen atoms are not all the same as one another.

"Aryloxyalkyl" means an alkyl radical substituted with aryloxy group as defined herein.

"Aryloxyaryl" means an aryl radical substituted with aryloxy group as defined herein.

"Aryloxyheteroaryl" means a heteroaryl radical substituted with aryloxy group as defined herein.

"Halo/Halogen" refers to fluorine, chlorine, bromine, iodine. Chlorine and fluorine are generally preferred.

Suitable groups and substituents on the groups may be selected from those described anywhere in the specification.

The term "substituted," as used herein, means that any one or more hydrogen on the designated atom is replaced with a selection from the indicated group, provided that the designated atom's normal valency is not exceeded, and that the substitution results in a stable compound. The term "substituted," as used herein, means that any one or more hydrogens on the designated atom is replaced with a selection from the indicated group, provided that the designated atom's normal valency is not exceeded, and that the substitution results in a stable compound.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of the basic residues. Such conventional non-toxic salts include, but are not limited to, those derived from inorganic and organic acids selected from sodium, potassium, 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromie, hydrochloric, hydroiodide, hydroxymaleic, hydroxynaphthoic, isethionic, lactic, lactobionic, -lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The term 'optional' or 'optionally' means that the subsequent described event or circumstance may or may not occur, and the description includes instances where the event or circumstance occur and instances in which it does not. For example, optionally substituted alkyl' means either 'alkyl' or 'substituted alkyl'. Further an optionally substituted group includes an unsubstituted group.

Unless otherwise stated in the specification, structures depicted herein are also meant to include compounds which differ only in the presence of one or more isotopically enriched atoms.

Particularly useful compounds may be selected from but not limited to the following:

(R,E)-2-(1-ethylpyrrolidin-2-yl)-N-((1,2,3,5,6,7-hexahydro-s-indacen-4-yl)carbamoyl)-ethanesulfonamide;

(S,E)-2-(1-ethylpyrrolidin-2-yl)-N-((1,2,3,5,6,7-hexahydro-s-indacen-4-yl)carbamoyl)-ethanesulfonamide;

(R,E)-N-((1,2,3,5,6,7-hexahydro-s-indacen-4-yl)carbamoyl)-2-(pyrrolidin-2-yl)ethene-1-sulfonamide;

(R,E)-N-((1,2,3,5,6,7-hexahydro-s-indacen-4-yl)carbamoyl)-2-(1-propylpyrrolidin-2-yl)ethene-1-sulfonamide;

(R,E)-2-(1-(cyclopropylmethyl)pyrrolidin-2-yl)-N-((1,2,3,5,6,7-hexahydro-s-indacen-4-yl)carbamoyl)ethene-1-sulfonamide;

(R,E)-N-((1,2,3,5,6,7-hexahydro-s-indacen-4-yl)carbamoyl)-2-(1-methylpyrrolidin-2-yl)ethene-1-sulfonamide;

(R,E)-N-((1,2,3,5,6,7-hexahydro-s-indacen-4-yl)carbamoyl)-2-(1-(methylsulfonyl)-pyrrolidin-2-yl)ethene-1-sulfonamide;

(R,E)-2-(1-acetylpyrrolidin-2-yl)-N-(1,2,3,5,6,7-hexahydro-s-indacen-4-yl)carbamoyl)-ethene-1-sulfonamide;

(E)-2-(1-benzylpiperidin-4-yl)-N-((1,2,3,5,6,7-hexahydro-s-indacen-4-yl)carbamoyl)-ethanesulfonamide;

tert-butyl (R,E)-2-(2-(N-((1,2,3,5,6,7-hexahydro-s-indacen-4-yl)carbamoyl)sulfamoyl)-vinyl)pyrrolidine-1-carboxylate;

(R,E)-N-((1,2,3,5,6,7-hexahydro-s-indacen-4-yl)carbamoyl)-2-(1-(2-methoxyethyl)pyrrolidin-2-yl)ethenesulfonamide;

(R,E)-N-((1,2,3,5,6,7-hexahydro-s-indacen-4-yl)carbamoyl)-2-(1-(isopropylsulfonyl)pyrrolidin-2-yl)ethenesulfonamide;

(R,E)-2-(1-((3-fluorophenyl)sulfonyl)pyrrolidin-2-yl)-N-((1,2,3,5,6,7-hexahydro-s-indacen-4-yl)carbamoyl)ethenesulfonamide;

(R,E)-N-((1,2,3,5,6,7-hexahydro-s-indacen-4-yl)carbamoyl)-2-(1-(pyrazine-2-carbonyl)pyrrolidin-2-yl)ethenesulfonamide;

(R,E)-2-(2-(N-((1,2,3,5,6,7-hexahydro-s-indacen-4-yl)carbamoyl)sulfamoyl)vinyl)pyrrolidine-1-carboxamide;

(R,E)-2-(1-(cyclopropanecarbonyl)pyrrolidin-2-yl)-N-((1,2,3,5,6,7-hexahydro-s-indacen-4-yl)carbamoyl)ethene-1-sulfonamide;

(R,E)-N-((1,2,3,5,6,7-hexahydro-s-indacen-4-yl)carbamoyl)-2-(1-(2,2,2-trifluoroacetyl)pyrrolidin-2-yl)ethene-1-sulfonamide;

(R,E)-N-((1,2,3,5,6,7-hexahydro-s-indacen-4-yl)carbamoyl)-2-(1-(2-(methylthio)ethyl)pyrrolidin-2-yl)ethene-1-sulfonamide;

(R,E)-N-((1,2,3,5,6,7-hexahydro-s-indacen-4-yl)carbamoyl)-2-(1-(2,2,2-trifluoroethyl)pyrrolidin-2-yl)ethene-1-sulfonamide;

(R,E)-N-((1,2,3,5,6,7-hexahydro-s-indacen-4-yl)carbamoyl)-2-(1-isobutylpyrrolidin-2-yl)ethene-1-sulfonamide;

(R,E)-2-(1-(ethylsulfonyl)pyrrolidin-2-yl)-N-((1,2,3,5,6,7-hexahydro-s-indacen-4-yl)carbamoyl)ethene-1-sulfonamide;

(R,E)-N-((1,2,3,5,6,7-hexahydro-s-indacen-4-yl)carbamoyl)-2-(1-isopropylpyrrolidin-2-yl)ethene-1-sulfonamide;

(R,E)-N-((1,2,3,5,6,7-hexahydro-s-indacen-4-yl)carbamoyl)-2-(1-(3-(methylsulfonyl)propyl)pyrrolidin-2-yl)ethenesulfonamide;

(R,E)-2-(1-benzoylpyrrolidin-2-yl)-N-((1,2,3,5,6,7-hexahydro-s-indacen-4-yl)carbamoyl)ethenesulfonamide;

(R,E)-N-((2-(1-benzoylpyrrolidin-2-yl)vinyl)sulfonyl)-N-((1,2,3,5,6,7-hexahydro-s-indacen-4-yl)carbamoyl)benzamide;

(R,E)-N-((1,2,3,5,6,7-hexahydro-s-indacen-4-yl)carbamoyl)-2-(pyrrolidin-2-yl)ethenesulfonamide;
(R,E)-N-((1,2,3,5,6,7-hexahydro-s-indacen-4-yl)carbamoyl)-2-(1-(thiophene-3-carbonyl)pyrrolidin-2-yl)ethenesulfonamide;
(R,E)-N-((1,2,3,5,6,7-hexahydro-s-indacen-4-yl)carbamoyl)-2-(pyrrolidin-2-yl)ethene-1-sulfonamide methane sulfonate;
(R,E)-N-((1,2,3,5,6,7-hexahydro-s-indacen-4-yl)carbamoyl)-2-(pyrrolidin-2-yl)ethene-1-sulfonamide maleate;
(R,Z)—N-((1,2,3,5,6,7-hexahydro-s-indacen-4-yl)carbamoyl)-2-(pyrrolidin-2-yl)ethene-1-sulfonamide;
(S,E)-N-((1,2,3,5,6,7-hexahydro-s-indacen-4-yl)carbamoyl)-3-(pyrrolidin-2-yl)prop-1-ene-1-sulfonamide;
(R,E)-2-(1-(cyclohexylsulfonyl)pyrrolidin-2-yl)-N-((1,2,3,5,6,7-hexahydro-s-indacen-4-yl)carbamoyl)ethene-1-sulfonamide;
(R,Z)—N-((1,2,3,5,6,7-hexahydro-s-indacen-4-yl)carbamoyl)-2-(1-methylpyrrolidin-2-yl)ethene-1-sulfonamide;
(R,E)-2-(1-(cyclohexylmethyl)pyrrolidin-2-yl)-N-((1,2,3,5,6,7-hexahydro-s-indacen-4-yl)carbamoyl)ethene-1-sulfonamide;
(R,E)-2-(1-cyclohexylpyrrolidin-2-yl)-N-((1,2,3,5,6,7-hexahydro-s-indacen-4-yl)carbamoyl)ethene-1-sulfonamide;
(R,E)-N-((1,2,3,5,6,7-hexahydro-s-indacen-4-yl)carbamoyl)-2-(1-(1-methylpiperidin-4-yl)pyrrolidin-2-yl)ethene-1-sulfonamide;
(R,Z)—N-((1,2,3,5,6,7-hexahydro-s-indacen-4-yl)carbamoyl)-2-(1-isopropylpyrrolidin-2-yl)ethene-1-sulfonamide;
(R,E)-N-((1,2,3,5,6,7-hexahydro-s-indacen-4-yl)carbamoyl)-2-(1-(tetrahydro-2H-pyran-4-yl)pyrrolidin-2-yl)ethene-1-sulfonamide;
(R,E)-N-((1,2,3,5,6,7-hexahydro-s-indacen-4-yl)carbamoyl)-2-(1-(oxetan-3-yl)pyrrolidin-2-yl)ethene-1-sulfonamide;
(R,E)-N-((1,2,3,5,6,7-hexahydro-s-indacen-4-yl)carbamoyl)-2-(1-(tetrahydro-2H-thiopyran-4-yl)pyrrolidin-2-yl)ethene-1-sulfonamide;
(R,E)-N-((1,2,3,5,6,7-hexahydro-s-indacen-4-yl)carbamoyl)-2-(1-(thiazol-2-ylmethyl)pyrrolidin-2-yl)ethene-1-sulfonamide;
(E)-N-((1,2,3,5,6,7-hexahydro-s-indacen-4-yl)carbamoyl)-2-(piperidin-4-yl)ethenesulfonamide;
(E)-N-((1,2,3,5,6,7-hexahydro-s-indacen-4-yl)carbamoyl)-2-(1-methylpiperidin-4-yl)ethenesulfonamide;
(E)-N-((1,2,3,5,6,7-hexahydro-s-indacen-4-yl)carbamoyl)-2-(1-(methylsulfonyl)piperidin-4-yl)ethenesulfonamide;
(E)-2-(1-acetylpiperidin-4-yl)-N-((1,2,3,5,6,7-hexahydro-s-indacen-4-yl)carbamoyl)ethene-sulfonamide;
tert-butyl (E)-4-(2-(N-((1,2,3,5,6,7-hexahydro-s-indacen-4-yl)carbamoyl)sulfamoyl)vinyl)-piperidine-1-carboxylate;
(E)-2-(1-ethylpiperidin-4-yl)-N-((1,2,3,5,6,7-hexahydro-s-indacen-4-yl)carbamoyl)ethene-1-sulfonamide;
(R,E)-2-(1-ethylpyrrolidin-3-yl)-N-((1,2,3,5,6,7-hexahydro-s-indacen-4-yl)carbamoyl)-ethenesulfonamide;
(R,E)-1,1-diethyl-3-(2-(N-((1,2,3,5,6,7-hexahydro-s-indacen-4-yl)carbamoyl)sulfamoyl)-vinyl)pyrrolidin-1-iumbromide;
(E)-N-((1,2,3,5,6,7-hexahydro-s-indacen-4-yl)carbamoyl)-2-(pyrrolidin-3-yl)ethene-sulfonamide;
(R,E)-N-((1,2,3,5,6,7-hexahydro-s-indacen-4-yl)carbamoyl)-2-(2-methylpyrrolidin-2-yl)ethene-1-sulfonamide;
tert-butyl (R,E)-2-(2-(N-((1,2,3,5,6,7-hexahydro-s-indacen-4-yl)carbamoyl)sulfamoyl)vinyl)-2-methylpyrrolidine-1-carboxylate;
(R,E)-2-(1-acetyl-2-methylpyrrolidin-2-yl)-N-((1,2,3,5,6,7-hexahydro-s-indacen-4-yl)carbamoyl)ethene-1-sulfonamide;
(R,E)-1,1-diethyl-2-(2-(N-((1,2,3,5,6,7-hexahydro-s-indacen-4-yl)carbamoyl)sulfamoyl)-vinyl)-2-methylpyrrolidin-1-ium bromide;
(R,E)-N-((1,2,3,5,6,7-hexahydro-s-indacen-4-yl)carbamoyl)-2-(2-methyl-1-(methylsulfonyl)-pyrrolidin-2-yl)ethene-1-sulfonamide;
(R,E)-2-(1,2-dimethylpyrrolidin-2-yl)-N-((1,2,3,5,6,7-hexahydro-s-indacen-4-yl)carbamoyl)ethene-1-sulfonamide;
(R,E)-2-(1-ethyl-2-methylpyrrolidin-2-yl)-N-((1,2,3,5,6,7-hexahydro-s-indacen-4-yl)carbamoyl)ethene-1-sulfonamide;
(R,E)-2-(1-(cyclopropylmethyl)-2-methylpyrrolidin-2-yl)-N-((1,2,3,5,6,7-hexahydro-s-indacen-4-yl)carbamoyl)ethene-1-sulfonamide;
(S,E)-N-((1,2,3,5,6,7-hexahydro-s-indacen-4-yl)carbamoyl)-2-(pyrrolidin-2-yl)ethene-sulfonamide;
(S,E)-N-((1,2,3,5,6,7-hexahydro-s-indacen-4-yl)carbamoyl)-2-(1-methylpyrrolidin-2-yl)ethenesulfonamide;
(S,E)-tert-butyl2-(2-(N-((1,2,3,5,6,7-hexahydro-s-indacen-4-yl)carbamoyl)sulfamoyl)vinyl)pyrrolidine-1-carboxylate;
(S,E)-2-(1-(cyclopropylmethyl)pyrrolidin-2-yl)-N-((1,2,3,5,6,7-hexahydro-s-indacen-4-yl)carbamoyl)ethenesulfonamide;
(S,E)-N-((1,2,3,5,6,7-hexahydro-s-indacen-4-yl)carbamoyl)-2-(1-(pyridin-3-ylsulfonyl)-pyrrolidin-2-yl)ethenesulfonamide;
(S,E)-N-((2,6-diisopropylphenyl)carbamoyl)-2-(pyrrolidin-2-yl)ethenesulfonamide;
(S,E)-N-((2,6-diisopropylphenyl)carbamoyl)-2-(1-ethylpyrrolidin-2-yl)ethenesulfonamide;
(S,E)-N-((2,6-diisopropylphenyl)carbamoyl)-2-(1-(methylsulfonyl)pyrrolidin-2-yl)ethene-sulfonamide;
(S,E)-N-((2,6-diisopropylphenyl)carbamoyl)-2-(1-methylpyrrolidin-2-yl)ethenesulfonamide;
(S,E)-2-(1-acetylpyrrolidin-2-yl)-N-((2,6-diisopropylphenyl)carbamoyl)ethenesulfonamide;
(S,E)-2-(1-acetylpyrrolidin-2-yl)-N-((1,2,3,5,6,7-hexahydro-s-indacen-4-yl)carbamoyl)-ethenesulfonamide;
(S,E)-N-((1,2,3,5,6,7-hexahydro-s-indacen-4-yl)carbamoyl)-2-(1-(tetrahydro-2H-pyran-4-carbonyl)pyrrolidin-2-yl)ethenesulfonamide;
(E)-N-((1,2,3,5,6,7-hexahydro-s-indacen-4-yl)carbamoyl)-2-(tetrahydro-2H-pyran-4-yl)ethenesulfonamide;
(S,E)-N-((1,2,3,5,6,7-hexahydro-s-indacen-4-yl)carbamoyl)-2-(1-nicotinoylpyrrolidin-2-yl)ethenesulfonamide;
(E)-N-((1,2,3,5,6,7-hexahydro-s-indacen-4-yl)carbamoyl)-2-(tetrahydrofuran-2-yl)ethene-1-sulfonamide;
(S,E)-N-((1,2,3,5,6,7-hexahydro-s-indacen-4-yl)carbamoyl)-2-(1-(thiophen-2-ylmethyl)-pyrrolidin-2-yl)ethene-1-sulfonamide;
tert-butyl (S,E)-2-(2-(N-((4-fluoro-2,6-diisopropylphenyl)carbamoyl)sulfamoyl)vinyl)-pyrrolidine-1-carboxylate;
(S,E)-N-((4-fluoro-2,6-diisopropylphenyl)carbamoyl)-2-(pyrrolidin-2-yl)ethene-1-sulfonamide;
(S,E)-N-((4-fluoro-2,6-diisopropylphenyl)carbamoyl)-2-(1-methylpyrrolidin-2-yl)ethene-1-sulfonamide;
(R,E)-N-((1,2,3,5,6,7-hexahydro-s-indacen-4-yl)carbamoyl)-2-(1-isobutyl-2-methyl-pyrrolidin-2-yl)ethene-1-sulfonamide;
(R,E)-N-((1,2,3,5,6,7-hexahydro-s-indacen-4-yl)carbamoyl)-2-(2-methyl-1-propylpyrrolidin-2-yl)ethene-1-sulfonamide;

(S,E)-N-((1,2,3,5,6,7-hexahydro-s-indacen-4-yl)carbamoyl)-2-(1-(thiazol-2-yl)pyrrolidin-2-yl)ethene-1-sulfonamide;
(E)-N-((1,2,3,5,6,7-hexahydro-s-indacen-4-yl)carbamoyl)-2-(piperidin-3-yl)ethene-sulfonamide;
(E)-2-(1-ethylpiperidin-3-yl)-N-((1,2,3,5,6,7-hexahydro-s-indacen-4-yl)carbamoyl)ethene-sulfonamide;
(E)-tert-butyl 3-(2-(N-((1,2,3,5,6,7-hexahydro-s-indacen-4-yl)carbamoyl)sulfamoyl)vinyl)-piperidine-1-carboxylate;
(E)-N-((1,2,3,5,6,7-hexahydro-s-indacen-4-yl)carbamoyl)-2-(1-(methylsulfonyl)piperidin-3-yl)ethenesulfonamide;
(E)-2-(1-acetylpiperidin-3-yl)-N-((1,2,3,5,6,7-hexahydro-s-indacen-4-yl)carbamoyl)ethene-sulfonamide;
tert-butyl (E)-2-(2-(N-((1,2,3,5,6,7-hexahydro-s-indacen-4-yl)carbamoyl)sulfamoyl)vinyl)-azetidine-1-carboxylate;
(E)-N-((1,2,3,5,6,7-hexahydro-s-indacen-4-yl)carbamoyl)-2-(1-methylazetidin-2-yl)ethene-1-sulfonamide;
(E)-2-(azetidin-2-yl)-N-((1,2,3,5,6,7-hexahydro-s-indacen-4-yl)carbamoyl)ethene-1-sulfonamide;
(R,E)-N-((1,2,3,5,6,7-hexahydro-s-indacen-4-yl)carbamoyl)-2-(1-(tetrahydro-2H-pyran-4-yl)pyrrolidin-2-yl)ethene-1-sulfonamide;
(S,E)-2-(1-((5-chlorothiophen-2-yl)sulfonyl)pyrrolidin-2-yl)-N-((1,2,3,5,6,7-hexahydro-s-indacen-4-yl)carbamoyl)ethenesulfonamide;
(S,E)-2-(1-(benzylsulfonyl)pyrrolidin-2-yl)-N-((1,2,3,5,6,7-hexahydro-s-indacen-4-yl)carbamoyl)ethenesulfonamide;
(S,E)-N-((1,2,3,5,6,7-hexahydro-s-indacen-4-yl)carbamoyl)-2-(1-((4-methoxyphenyl)sulfonyl) pyrrolidin-2-yl)ethenesulfonamide;
(S,E)-N-((1,2,3,5,6,7-hexahydro-s-indacen-4-yl)carbamoyl)-2-(1-((4-fluorophenyl)sulfonyl) pyrrolidin-2-yl)ethenesulfonamide;
(S,E)-2-(1-((2-cyanophenyl)sulfonyl)pyrrolidin-2-yl)-N-((1,2,3,5,6,7-hexahydro-s-indacen-4-yl)carbamoyl)ethenesulfonamide;
(S,E)-2-(1-(cyclohexylsulfonyl)pyrrolidin-2-yl)-N-((1,2,3,5,6,7-hexahydro-s-indacen-4-yl)carbamoyl)ethenesulfonamide;
(S,E)-2-(1-(4-fluorobenzyl)pyrrolidin-2-yl)-N-((1,2,3,5,6,7-hexahydro-s-indacen-4-yl)carbamoyl)ethenesulfonamide;
(S,E)-2-(1-((4-cyanophenyl)sulfonyl)pyrrolidin-2-yl)-N-((1,2,3,5,6,7-hexahydro-s-indacen-4-yl)carbamoyl)ethene-1-sulfonamide;
(S,E)-2-(1-(4-cyanobenzyl)pyrrolidin-2-yl)-N-((1,2,3,5,6,7-hexahydro-s-indacen-4-yl)carbamoyl)ethene-1-sulfonamide;
(S,E)-N-((1,2,3,6,7,8-hexahydro-as-indacen-4-yl)carbamoyl)-2-(pyrrolidin-2-yl)ethene-1-sulfonamide;
(E)-N-((1,2,3,5,6,7-hexahydro-s-indacen-4-yl)carbamoyl)-2-(piperidin-2-yl)ethene-1-sulfonamide;
(E)-N-((1,2,3,5,6,7-hexahydro-s-indacen-4-yl)carbamoyl)-2-(1-methylpiperidin-2-yl)ethene-1-sulfonamide;
(E)-N-((1,2,3,6,7,8-hexahydro-as-indacen-4-yl)carbamoyl)-2-(1-methylpyrrolidin-2-yl)ethene-1-sulfonamide;
(E)-N-((1,2,3,6,7,8-hexahydro-as-indacen-4-yl)carbamoyl)-2-(1-(methylsulfonyl)pyrrolidin-2-yl)ethene-1-sulfonamide; ((E)-N-((1,2,3,5,6,7-hexahydro-s-indacen-4-yl)carbamoyl)-3-(piperidin-2-yl)prop-1-ene-1-sulfonamide;
(S,E)-N-((1,2,3,5,6,7-hexahydro-s-indacen-4-yl)carbamoyl)-2-(2-methylpyrrolidin-2-yl)ethene-1-sulfonamide;
(S,E)-2-(1,2-dimethylpyrrolidin-2-yl)-N-((1,2,3,5,6,7-hexahydro-s-indacen-4-yl)carbamoyl)ethene-1-sulfonamide;
(E)-N-((1,2,3,5,6,7-hexahydro-s-indacen-4-yl)carbamoyl)-2-(indolin-2-yl)ethene-1-sulfonamide;
tert-butyl(E)-2-(2-(N-((1,2,3,5,6,7-hexahydro-s-indacen-4-yl)carbamoyl)sulfamoyl)vinyl)indoline-1-carboxylate;
((S,E)-2-(1-(cyclopropylmethyl)-2-methylpyrrolidin-2-yl)-N-((1,2,3,5,6,7-hexahydro-s-indacen-4-yl)carbamoyl) ethene-1-sulfonamide;
(S,E)-2-(1-(cyclopropylsulfonyl)pyrrolidin-2-yl)-N-((1,2,3,5,6,7-hexahydro-s-indacen-4-yl)carbamoyl)ethene-1-sulfonamide;
tert-butyl (S,E)-2-(2-(N-((1,2,3,5,6,7-hexahydro-s-indacen-4-yl)carbamoyl)sulfamoyl)vinyl)-2-methylpyrrolidine-1-carboxylate;
tert-butyl (R,E)-2-(2-(N-((2,6-diisopropylphenyl)carbamoyl)sulfamoyl)vinyl)-2-methylpyrrolidine-1-carboxylate;
(R,E)-N-((2,6-diisopropylphenyl)carbamoyl)-2-(2-methylpyrrolidin-2-yl)ethene-1-sulfonamide 2,2,2-trifluoroacetate;
(R,E)-N-((2,6-diisopropylphenyl)carbamoyl)-2-(1,2-dimethylpyrrolidin-2-yl)ethene-1-sulfonamide;
(S,E)-2-(1-ethyl-2-methylpyrrolidin-2-yl)-N-((1,2,3,5,6,7-hexahydro-s-indacen-4-yl)carbamoyl)ethene-1-sulfonamide;
Bis sodium (R,E)-((2-(1,2-dimethylpyrrolidin-2-yl)vinyl)sulfonyl)(1,2,3,5,6,7-hexahydro-s-indacen-4-yl)carbamoyl)amide;
Sodium (R,E)-((2-(1,2-dimethylpyrrolidin-2-yl)vinyl)sulfonyl)((1,2,3,5,6,7-hexahydro-s-indacen-4-yl)carbamoyl) amide;
tert-butyl (S,E)-2-(2-(N-((2,6-diisopropylphenyl)carbamoyl)sulfamoyl)vinyl)-2-methylpyrrolidine-1-carboxylate;
(S,E)-N-((2,6-diisopropylphenyl)carbamoyl)-2-(2-methylpyrrolidin-2-yl)ethene-1-sulfonamide 2,2,2-trifluoroacetate;
(S,E)-N-((2,6-diisopropylphenyl)carbamoyl)-2-(1,2-dimethylpyrrolidin-2-yl)ethene-1-sulfonamide;
(R,E)-N-((1,2,3,5,6,7-hexahydro-s-indacen-4-yl)carbamoyl)-2-(2-methyl-1-(oxetan-3-yl)pyrrolidin-2-yl)ethene-1-sulfonamide;
tert-butyl (S,E)-2-(2-(N-((4-fluoro-2,6-diisopropylphenyl)carbamoyl)sulfamoyl)vinyl)-2-methylpyrrolidine-1-carboxylate;
(S,E)-N-((4-fluoro-2,6-diisopropylphenyl)carbamoyl)-2-(2-methylpyrrolidin-2-yl)ethene-1-sulfonamide 2,2,2-trifluoroacetate;
(S,E)-2-(1,2-dimethylpyrrolidin-2-yl)-N-((4-fluoro-2,6-diisopropylphenyl)carbamoyl)ethene-1-sulfonamide;
(E)-2-(1-acetylazetidin-2-yl)-N-((1,2,3,5,6,7-hexahydro-s-indacen-4-yl)carbamoyl)ethene-1-sulfonamide;
tert-butyl (R,E)-(2-(2-(2-(N-((1,2,3,5,6,7-hexahydro-s-indacen-4-yl)carbamoyl)sulfamoyl)vinyl)pyrrolidin-1-yl) ethylxmethyl)carbamate;
(S,E)-2-(1-allylpyrrolidin-2-yl)-N-((1,2,3,5,6,7-hexahydro-s-indacen-4-yl)carbamoyl)ethene-1-sulfonamide;
(S,E)-2-(1-(1H-benzo[d]imidazole-6-carbonyl)pyrrolidin-2-yl)-N-((1,2,3,5,6,7-hexahydro-s-indacen-4-yl)carbamoyl) ethene-1-sulfonamide;
(S,E)-2-(1-(cyclopropylsulfonyl)-2-methylpyrrolidin-2-yl)-N-((1,2,3,5,6,7-hexahydro-s-indacen-4-yl)carbamoyl) ethene-1-sulfonamide;
(S,E)-N-((1,2,3,5,6,7-hexahydro-s-indacen-4-yl)carbamoyl)-2-(1-(4-methoxybenzyl)pyrrolidin-2-yl)ethene-1-sulfonamide;
tert-butyl 5-((R)-2-((E)-2-(N-((1,2,3,5,6,7-hexahydro-s-indacen-4-yl)carbamoyl)sulfamoyl)vinyl)pyrrolidin-1-yl) hexahydrocyclopenta[c]pyrrole-2 (1H)-carboxylate;
(E)-N-((1,2,3,5,6,7-hexahydro-s-indacen-4-yl)carbamoyl)-2-((2R)-1-(octahydrocyclo-penta[c]pyrrol-5-yl)pyrrolidin-2-yl)ethene-1-sulfonamide 2,2,2-trifluoroacetate;

(E)-2-(1-(cyclopropylsulfonyl)azetidin-2-yl)-N-((1,2,3,5,6,7-hexahydro-s-indacen-4-yl)carbamoyl)ethene-1-sulfonamide;

(S,E)-N-((2,6-diisopropylphenyl)carbamoyl)-2-(1-(thiazol-2-yl)pyrrolidin-2-yl)ethene-1-sulfonamide;

tert-butyl (S,E)-(2-(2-(2-(N-((1,2,3,5,6,7-hexahydro-s-indacen-4-yl)carbamoyl)sulfamoyl)vinyl)-2-methylpyrrolidin-1-yl)ethyl)(methyl)carbamate;

potassium (R,E)-((2-(1,2-dimethylpyrrolidin-2-yl)vinyl)sulfonyl)((1,2,3,5,6,7-hexahydro-s-indacen-4-yl)carbamoyl)amide;

tert-butyl (E)-(2-(2-(2-(N-((1,2,3,5,6,7-hexahydro-s-indacen-4-yl)carbamoyl)sulfamoyl)vinyl)azetidin-1-yl)ethyl)(methyl)carbamate;

(S,E)-2-(1-(cyclohexylmethyl)-2-methylpyrrolidin-2-yl)-N-((1,2,3,5,6,7-hexahydro-s-indacen-4-yl)carbamoyl)ethene-1-sulfonamide;

Sodium (R,E)-((1,2,3,5,6,7-hexahydro-s-indacen-4-yl)carbamoyl)((2-(1-(tetrahydro-2H-thiopyran-4-yl)pyrrolidin-2-yl)vinyl)sulfonyl)amide;

sodium (R,E)-((2-(1-cyclohexylpyrrolidin-2-yl)vinyl)sulfonyl)((1,2,3,5,6,7-hexahydro-s-indacen-4-yl)carbamoyl)amide;

sodium (S,E)-((2,6-diisopropylphenyl)carbamoyl)((2-(1,2-dimethylpyrrolidin-2-yl)vinyl)sulfonyl)amide;

sodium (R,E)-((1,2,3,5,6,7-hexahydro-s-indacen-4-yl)carbamoyl)((2-(1-methylpyrrolidin-2-yl)vinyl)sulfonyl)amide;

potassium (R,E)-((1,2,3,5,6,7-hexahydro-s-indacen-4-yl)carbamoyl)((2-(1-methylpyrrolidin-2-yl)vinyl)sulfonyl)amide;

sodium (S,E)-((2-(1,2-dimethylpyrrolidin-2-yl)vinyl)sulfonyl)((1,2,3,5,6,7-hexahydro-s-indacen-4-yl)carbamoyl)amide;

sodium (S,E)-((2-(1-ethylpyrrolidin-2-yl)vinyl)sulfonyl)((1,2,3,5,6,7-hexahydro-s-indacen-4-yl)carbamoyl)amide;

(S,E)-N-((1,2,3,5,6,7-hexahydro-s-indacen-4-yl)carbamoyl)-2-(1-(2-hydroxyethyl)pyrrolidin-2-yl)ethene-1-sulfonamide;

tert-butyl (E)-2-(2-(N-((1,2,3,5,6,7-hexahydro-s-indacen-4-yl)carbamoyl)sulfamoyl)vinyl)-2-methylazetidine-1-carboxylate;

(E)-2-(1,2-dimethylazetidin-2-yl)-N-((1,2,3,5,6,7-hexahydro-s-indacen-4-yl)carbamoyl)ethene-1-sulfonamide;

tert-butyl (S,E)-2-ethyl-2-(2-(N-((1,2,3,5,6,7-hexahydro-s-indacen-4-yl)carbamoyl)sulfamoyl)vinyl)pyrrolidine-1-carboxylate;

tert-butyl (S,E)-2-(2-(N-((1,2,3,6,7,8-hexahydro-as-indacen-4-yl)carbamoyl)sulfamoyl)vinyl)-2-methylpyrrolidine-1-carboxylate;

(S,E)-2-(2-ethylpyrrolidin-2-yl)-N-((1,2,3,5,6,7-hexahydro-s-indacen-4-yl)carbamoyl)ethene-1-sulfonamide 2,2,2-trifluoroacetate;

(S,E)-N-((1,2,3,6,7,8-hexahydro-as-indacen-4-yl)carbamoyl)-2-(2-methylpyrrolidin-2-yl)ethene-1-sulfonamide 2,2,2-trifluoroacetate;

(S,E)-2-(1,2-dimethylpyrrolidin-2-yl)-N-((1,2,3,6,7,8-hexahydro-as-indacen-4-yl)carbamoyl)ethene-1-sulfonamide;

tert-butyl (R,E)-2-(2-(N-((1,2,3,6,7,8-hexahydro-as-indacen-4-yl)carbamoyl)sulfamoyl)vinyl)-2-methylpyrrolidine-1-carboxylate;

(R,E)-N-((1,2,3,6,7,8-hexahydro-as-indacen-4-yl)carbamoyl)-2-(2-methylpyrrolidin-2-yl)ethene-1-sulfonamide 2,2,2-trifluoroacetate;

(R,E)-2-(1,2-dimethylpyrrolidin-2-yl)-N-((1,2,3,6,7,8-hexahydro-as-indacen-4-yl)carbamoyl)ethene-1-sulfonamide;

tert-butyl (R,E)-2-(3-(N-((1,2,3,5,6,7-hexahydro-s-indacen-4-yl)carbamoyl)sulfamoyl)allyl)-2-methylpyrrolidine-1-carboxylate;

tert-butyl (R,E)-(2-(2-(3-(N-((1,2,3,5,6,7-hexahydro-s-indacen-4-yl)carbamoyl)sulfamoyl)allyl)-2-methylpyrrolidin-1-yl)ethyl)(methyl)carbamate;

(R,E)-3-(1,2-dimethylpyrrolidin-2-yl)-N-((1,2,3,5,6,7-hexahydro-s-indacen-4-yl)carbamoyl)prop-1-ene-1-sulfonamide;

tert-butyl (S,E)-(3-(2-(2-(N-((1,2,3,5,6,7-hexahydro-s-indacen-4-yl)carbamoyl)sulfamoyl)vinyl)pyrrolidin-1-yl)propyl)(methyl)carbamate;

tert-butyl (E)-(3-(2-(2-(N-((1,2,3,5,6,7-hexahydro-s-indacen-4-yl)carbamoyl)sulfamoyl)vinyl)-2-methylazetidin-1-yl)propyl)(methyl)carbamate;

tert-butyl (E)-(2-(2-(2-(N-((1,2,3,5,6,7-hexahydro-s-indacen-4-yl)carbamoyl)sulfamoyl)vinyl)-2-methylazetidin-1-yl)ethyl)(methyl)carbamate;

(E)-N-((1,2,3,5,6,7-hexahydro-s-indacen-4-yl)carbamoyl)-2-(2-methyl-1-(2-(methylthio)ethyl)azetidin-2-yl)ethene-1-sulfonamide;

(E)-N-((1,2,3,5,6,7-hexahydro-s-indacen-4-yl)carbamoyl)-2-(2-methyl-1-(oxetan-3-yl)azetidin-2-yl)ethene-1-sulfonamide;

tert-butyl (S)-2-(((S)-2-((E)-2-(N-((1,2,3,5,6,7-hexahydro-s-indacen-4-yl)carbamoyl)sulfamoyl)vinyl)-2-methylazetidin-1-yl)methyl)-2-methylpyrrolidine-1-carboxylate;

tert-butyl (S)-2-(((R)-2-((E)-2-(N-((1,2,3,5,6,7-hexahydro-s-indacen-4-yl)carbamoyl)sulfamoyl)vinyl)-2-methylazetidin-1-yl)methyl)-2-methylpyrrolidine-1-carboxylate;

(R,E)-N-((1,2,3,5,6,7-hexahydro-s-indacen-4-yl)carbamoyl)-2-(1-(2-sulfamoylethyl)pyrrolidin-2-yl)ethene-1-sulfonamide;

(S,E)-2-(2-ethyl-1-methylpyrrolidin-2-yl)-N-((1,2,3,5,6,7-hexahydro-s-indacen-4-yl)carbamoyl)ethene-1-sulfonamide;

(R,E)-2-(1-(but-2-yn-1-yl)pyrrolidin-2-yl)-N-((1,2,3,5,6,7-hexahydro-s-indacen-4-yl)carbamoyl)ethene-1-sulfonamide;

or pharmaceutically acceptable salts of any of the compounds above.

Following is a list of abbreviations used in the description of the preparation of the compounds of the present invention:

μg: microgram
$^1$H NMR: Proton nuclear magnetic resonance
bs: broad singlet
CDCl$_3$: Deuterated chloroform
CHCl$_3$: Chloroform
d: doublet
DAMP: damage-associated molecular pattern;
DCM: Dichloromethane
dd: doublet of doublet
DMAC: N,N-(Dimethylacetamide)
DMAP: 4-(Dimethylamino) pyridine
DMF: N,N-Dimethyl formamide
DMSO: Dimethyl sulfoxide
dt: doublet of triplet
EDTA: Ethylenediaminetertraacetic acid
EtOAc: Ethyl acetate
EtOH: Ethanol
HCl(g): Hydrogen chloride (gas)
ILIβ: Interleukin 1 beta
K2CO3: Potassium carbonate
LPS: Lipopolysaccharide
m: multiplet
MeOH: Methanol mmol: millimoles
MS: Mass spectrum
N₂: Nitrogen
Na₂CO₃: Sodium carbonate
ng: nanogram
NIS: N-iodosuccinimide
NLRP3: NOD-like receptor family, pyrin domain-containing protein 3
PAMP: pathogen-associated molecular pattern;
PMA: Phorbol 12-myristate 13-acetate
POCl₃: Phosphorylchloride
RM: reaction mixture
R.T; r.t: room temperature
s: singlet
t: Triplet
td: triplet of doublet
THF: Tetrahydrofuran
TLC: Thin layer chromatography
TLR: Toll-like receptor.
TNF α: Tumor necrosis factor alpha General Process for Preparation The novel compounds of the present invention can be prepared using the reactions and techniques described below, together with conventional techniques known to those skilled in the art of organic synthesis, or variations thereon as appreciated by those skilled in the art.

The reactions can be performed in solvents appropriate to the reagents and materials employed and suitable for the transformations being affected. Preferred methods include, but not limited to those described below, where all symbols are as defined earlier unless and otherwise defined below.

The compounds of the general formula (I) can be prepared as described in schemes below along with suitable modifications/variations which are well within the scope of a person skilled in the art.

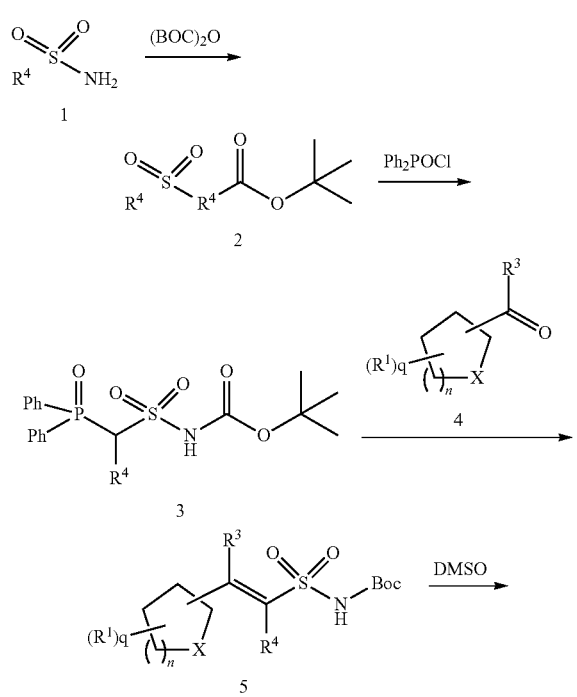

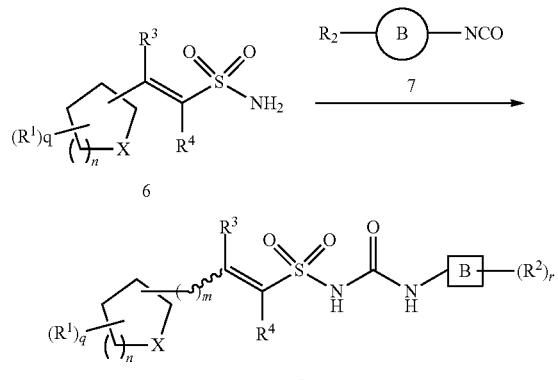

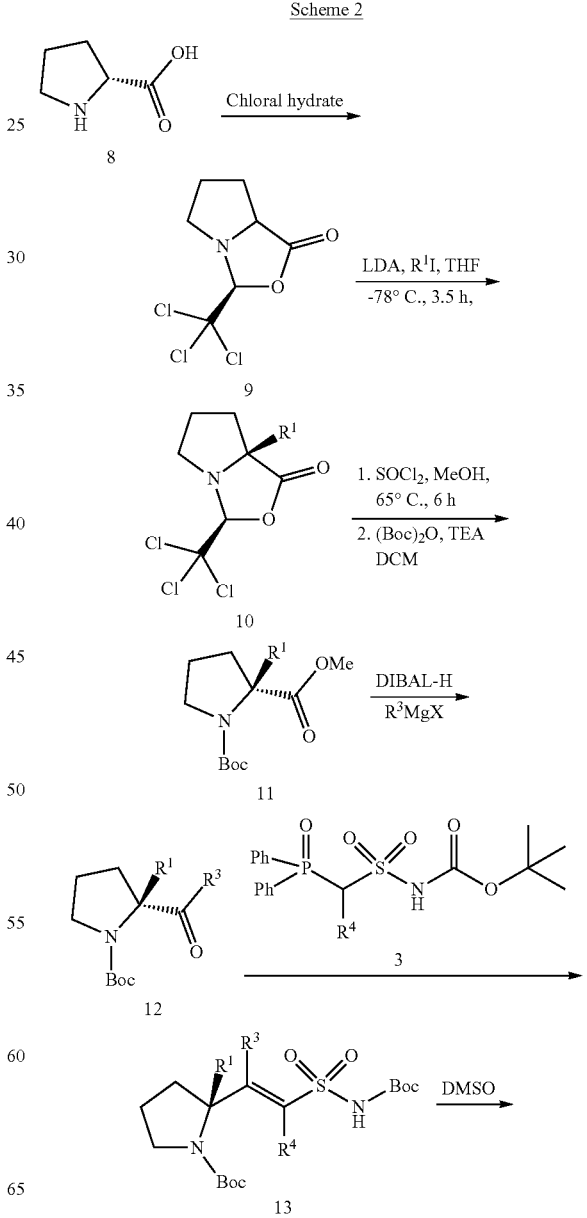

-continued

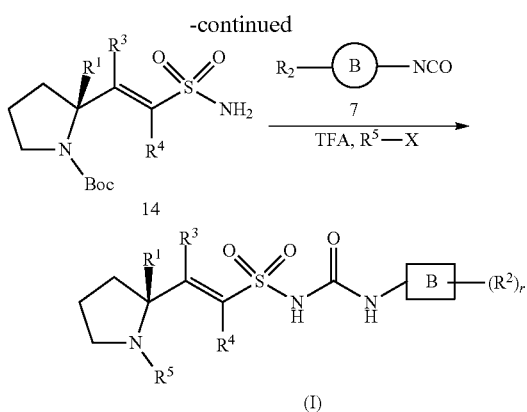

Scheme 3

(Scheme 3 structures 3, 15, 16, I)

Wherein each of A, B, $R^1$, $R^2$, $R^3$, and $R^4$, are as defined earlier. Compound (2) can be prepared by variety of methods familiar to those skilled in art using a reagent like Boc anhydride from commercially available methane sulfonamide (1). Compound (2) on treatment with diphenylphosphinic chloride under suitable conditions and appropriate solvents provided compound 3 (ref. Synthesis 2003, 15, 2321-24). Compound 3 on treatment with aldehyde or ketone derivative (4) under suitable conditions in presence of base like sodium hydride and appropriate solvent provided compound (5), which can be deprotected under suitable conditions to afford compound (6). Compound (3) on treatment with isocyanato derivative (7) under suitable conditions in presence of base like sodium hydride and appropriate solvent to afford compound of formula (I) (Scheme 1).

Alternatively, compound of formula (I) can also be prepared as depicted in Scheme 2 and Scheme 3.

Specific reaction conditions, solvents and other parameters necessary for carrying out the process steps as described above are well within the capabilities of a person skilled in the art.

The invention is further illustrated by the following non-limiting examples which describe the preferred way of carrying out the present invention. These are provided without limiting the scope of the present invention in any way.

$^1$H NMR spectral data given in the examples (vide infra) are recorded using a 400 MHz spectrometer (Bruker AVANCE-400) and reported in S scale. Until and otherwise mentioned the solvent used for NMR is $CDCl_3$ using TMS as the internal standard.

According to a feature of the present invention, there is provided general structure of an intermediate of formula (5), formula (6)

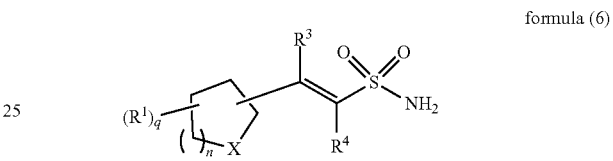

where all symbols are as defined above.

In another embodiment, there is provided general structure of an Intermediate of formula (6)

Formula (5)

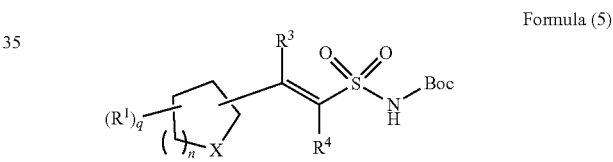

where all symbols are as defined above.

In another embodiment, there is provided general structure of an intermediate of formula (15)

Formula (15)

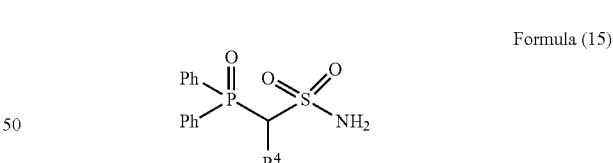

Where all symbols are as defined above.

In another embodiment, there is provided general structure of an intermediate of formula (16)

(Formula 16)

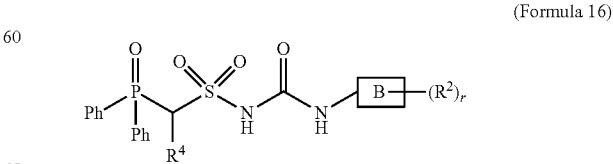

Where all symbols are as defined above.

In yet another embodiment, there is provided a process for the preparation of intermediate of formula (5), (6), 15) and (16) as per Scheme 1 and 3 disclosed in the specification.

Intermediate-1a: Preparation of tert-butyl (R,E)-2-(2-(N-(tert-butoxycarbonyl)-sulfamoyl)-vinyl)pyrrolidine-1-carboxylate

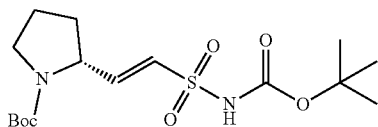 [SMILES: CC(C)(C)OC(=O)NS(=O)(=O)/C=C/[C@H]1CCCN1C(=O)OC(C)(C)C]

A 500 mL, three neck, round-bottomed flask was equipped with magnetic stirrer, N2 balloon, thermos-pocket, dry ice bath. tert-butyl ((diphenylphosphoryl)methyl)sulfonylcarbamate (3) (10 g, 25.3 mmol) was dissolved in DMF (100 mL) under Nitrogen atmosphere. It was cooled to −20° C. and added NaH (2.023 g, 50.6 mmol). It was gradually warmed to 25° C. and stirred for 30 min. Again cooled to −20° C. and a solution of (R)-tert-butyl 2-formylpyrrolidine-1-carboxylate (Org. Lett. 2008, 10, 4, 3045-3048) (6.05 g, 30.3 mmol) in DMF (50 mL) was added dropwise over a period of 1 h at −20° C. temp. After the addition reaction mixture was warmed to r.t. and further stirred for 17 h. Reaction mixture was cooled to 0° C. and acidified with saturated citric acid solution (30 mL), and water (200 mL), solid was precipitate out, which was filtered, washed and dried to yield, (R,E)-tert-butyl 2-(2-(N-(tert-butoxycarbonyl)sulfamoyl)vinyl)pyrrolidine-1-carboxylate (4.6 g, 12.22 mmol, 48% yield).

$^1$H NMR (400 MHz, DMSO-d$_6$): δ=11.33 (s, 1H), 6.78-6.67 (m, 1H), 6.52 (d, J=14.2 Hz, 1H), 4.50-4.42 (m, 1H), 3.33-3.27 (m, 2H), 2.1 (br s, 1H), 1.79-1.71 (m, 3H), 1.44-1.35 (m, 18H); MS (ESI): m/z (%)=375.30 (100%) (M−H)$^-$.

Intermediate-1b: Preparation of tert-butyl (S,E)-2-(2-(N-(tert-butoxycarbonyl)-sulfamoyl)-vinyl)pyrrolidine-1-carboxylate

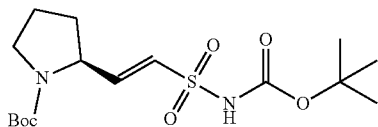 [SMILES: CC(C)(C)OC(=O)NS(=O)(=O)/C=C/[C@@H]1CCCN1C(=O)OC(C)(C)C]

Intermediate-1b was also prepared as per the procedure described for synthesis of Intermediate-1a using (S)-tert-butyl 2-formylpyrrolidine-1-carboxylate.

Intermediate-2a: Preparation of (RE)-tert-butyl 2-(2-sulfamoylvinyl)pyrrolidine-1-carboxylate

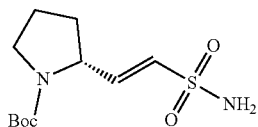 [SMILES: CC(C)(C)OC(=O)N1CCC[C@@H]1/C=C/S(N)(=O)=O]

The compound [Intermediate 1a] (18 g) was dissolved in DMSO (180 mL) and heated to 85° C. (disappearance of the starting material was monitored by TLC). The reaction was cooled, poured into water (900 mL) & extracted with EtOAc (3×300 mL). The solvent was concentrated in vacuo & purified by column chromatography on silica gel (50% EtOAc:n-Hexane) to give product (R,E)-tert-butyl 2-(2-sulfamoylvinyl)pyrrolidine-1-carboxylate (14.3 g, 53.7 mmol, 67% yield).

$^1$H NMR (400 MHz, DMSO-d$_6$): δ=6.99 (s, 2H), 6.40-6.38 (m, 1H), 6.34-6.30 (m, 1H), 4.40-4.32 (m, 2H), 3.28-3.25 (m, 1H), 2.21-1.99 (m, 1H), 1.81-1.67 (m, 3H), 1.38 (m, 9H); MS (ESI): m/z (%)=299.09 (50%) (M+Na)$^+$, 275.09 (100%) (M−1).

Intermediate-2b: Preparation of (S,E)-tert-butyl 2-(2-sulfamoylvinyl)pyrrolidine-1-carboxylate

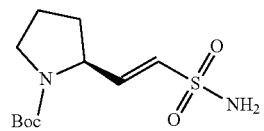 [SMILES: CC(C)(C)OC(=O)N1CCC[C@H]1/C=C/S(N)(=O)=O]

Intermediate-2b was also prepared as per the procedure described for synthesis of Intermediate-2a using Intermediate 1b.

Intermediate-2c: Preparation of tert-butyl (R,Z)-2-(2-sulfamoylvinyl)pyrrolidine-1-carboxylate

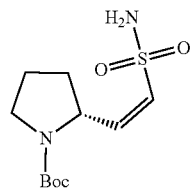 [SMILES: CC(C)(C)OC(=O)N1CCC[C@@H]1/C=C\S(N)(=O)=O]

Intermediate-2c was also obtained as per the procedure described for synthesis of Intermediate-2a.

$^1$H NMR (400 MHz, DMSO-d$_6$): δ=7.06 (s, 2H), 6.22 (d, J=12 Hz, 1H), (dd, J=12 Hz, J=11.2 Hz, 1H), 5.24-4.92 (m, 1H), 3.41-3.23 (m, 1H), 2.31-2.03 (m, 2H), 1.99-1.71 (m, 1H), 1.68-1.62 (m, 1H), 1.39 (m, 9H); MS (ESI): m/z (%)=299.09 (40%) (M+Na)$^+$.

Intermediate-2d: Preparation of tert-butyl (S,Z)-2-(2-sulfamoylvinyl)pyrrolidine-1-carboxylate

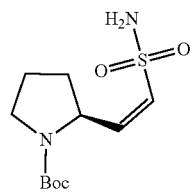 [SMILES: CC(C)(C)OC(=O)N1CCC[C@H]1/C=C\S(N)(=O)=O]

Intermediate-2d was also obtained as per the procedure described for synthesis of Intermediate-2b.

Intermediate-3a (Example 10): Preparation of tert-butyl (R,E)-2-(2-(N-((1,2,3,5,6,7-hexahydro-s-indacen-4-yl)carbamoyl)sulfamoyl)-vinyl)pyrrolidine-1-carboxylate

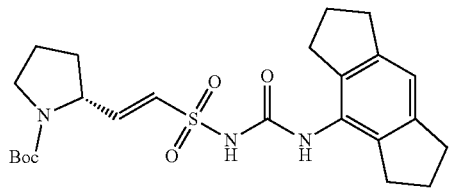 [SMILES: CC(C)(C)OC(=O)N1CCC[C@@H]1/C=C/S(=O)(=O)NC(=O)Nc1c2c(cc3c1CCC3)CCC2]

To a solution of the sulfonamide [Intermediate 2a] (22.0 gm, 80 mmol) in DMF (220 mL) at 0° C. was added NaH (60% dispersion in mineral oil) (3.82 gm, 96 mmol). The reaction was allowed to warm to r.t. and stirred for 30 min. 4-isocyanato-1,2,3,5,6,7-hexahydro-s-indacene (19.03 gm, 96 mmol) was added portionwise at 0° C. the reaction was warm to r.t. and stirred overnight. The reaction was acidified using 50% aq. citric acid up to pH=2.0, diluted with water (1500 mL), precipitate was filtered and dried to give product (38 g, 80 mmol, 100% yield). 1H NMR (400 MHz, DMSO-d6): δ=10.42 (s, 1H), 8.09 (s, 1H), 6.96 (s, 1H), 6.71-6.68 (m, 1H), 6.59 (d, J=14.8 Hz, 1H), 4.45-4.38 (m, 1H), 3.29-3.27 (m, 2H), 2.79 (t, J=7.2 Hz, 4H), 2.65 (t, J=7.2 Hz, 4H), 2.30-1.93 (m, 5H), 1.78-1.71 (m, 3H), 1.39-1.33 (m, 9H); MS (ESI): m/z (%)=498.18 (40%) (M+Na)+, 474.18 (100%) (M−1).

Intermediate-3b (Example 61): Preparation of tert-butyl (S,E)-2-(2-(N-((1,2,3,5,6,7-hexahydro-s-indacen-4-yl)carbamoyl)sulfamoyl)-vinyl)pyrrolidine-1-carboxylate

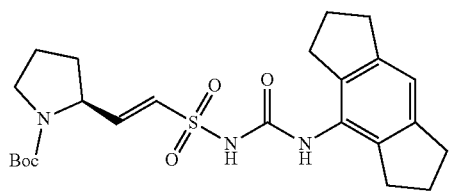 [SMILES: CC(C)(C)OC(=O)N1CCC[C@H]1/C=C/S(=O)(=O)NC(=O)Nc1c2c(cc3c1CCC3)CCC2]

Intermediate-3b was also prepared as per the procedure described for synthesis of Intermediate-2b.

$^1$H NMR (400 MHz, DMSO): δ=10.42 (bs, 1H), 8.09 (s, 1H), 6.96 (s, 1H), 6.71-6.67 (m, 1H), 6.61-6.57 (m, 1H), 4.45-4.38 (m, 1H), 3.29-3.25 (m, 2H), 2.81 (t, J=7.2 Hz, 4H), 2.67 (t, J=7.2 Hz, 4H), 2.09-1.93 (m, 5H), 1.78-1.71 (m, 3H), 1.33 (s, 9H); MS (ESI): m/z (%)=498.18 (80%) (M+Na)+.

Intermediate-4a: Preparation of tert-butyl (R)-2-formyl-2-methylpyrrolidine-1-carboxylate

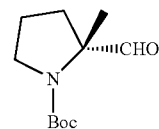

To a solution of 1-(tert-butyl) 2-methyl (R)-2-methylpyrrolidine-1,2-dicarboxylate (Singh et. al., RSC Adv., 2013, 3, 19533-19544) (98 g, 403 mmol) in dry DCM (2000 mL) to give a solution. DIBAL-H (806 mL of 1.5M in Toluene, 537 mmol) was added dropwise at −78° C. The reaction mixture was stirred at −78° C. for 2 h then was quenched with methanol (100 mL) at −78° C. temperature. The reaction mixture was acidified with 50% citric acid solution up to pH=4.0. Water (1000 mL) and DCM (1000 mL) were added. The aqueous layer was extracted with DCM (2×1500 mL). The combined organic layers was washed with water (1500 mL), brine (1000 mL), and dried over Na$_2$SO$_4$. The solvent was removed to give a product (83 g, 389 mmol, 97% yield).

$^1$H NMR (400 MHz, DMSO-d$_6$): δ=9.28 (m, 1H), 3.64-3.41 (m, 2H), 1.97-1.85 (m, 2H), 1.70-1.50 (m, 2H), 1.38-1.28 (m, 12H), rotamers; MS (ESI): m/z (%)=214.3 (100%) (M+H)$^+$.

Intermediate-4b: Preparation of tert-butyl (S)-2-formyl-2-methylpyrrolidine-1-carboxylate

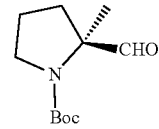

Intermediate-4b was also prepared as per the procedure described for synthesis of Intermediate-4a using 1-(tert-butyl) 2-methyl (S)-2-methylpyrrolidine-1,2-dicarboxylate.

Intermediate-5a: Preparation of tert-butyl (R,E)-2-(2-(N-(tert-butoxycarbonyl)sulfamoyl)vinyl)-2-methylpyrrolidine-1-carboxylate

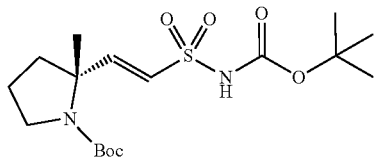 [SMILES: CC(C)(C)OC(=O)NS(=O)(=O)/C=C/[C@@]1(C)CCCN1C(=O)OC(C)(C)C]

To a solution of tert-butyl (((diphenylphosphoryl)methyl) sulfonyl)carbamate (153.0 gm, 387 mmol) in DMF (1530 mL) at 0° C. was added NaH (60% dispersion in mineral oil) (34 gm, 851 mmol). The reaction was allowed to warm to r.t. and stirred for 30 min. The aldehyde (tert-butyl (R)-2-formyl-2-methylpyrrolidine-1-carboxylate) (83 gm, 387 mmol) in DMF (830 mL) was added at dropwise at −20° C. the reaction was warm to r.t. & stirred overnight. The reaction was acidified using 50% aqueous citric acid (~500 mL) up to pH=2.0 the diluted with water (3000 mL) & extracted with EtOAc (2000 mL×2). The combined organic layer was washed with water (2000 mL×3), brine (1000 mL), dried over Na₂SO₄, concentrated & dried to give crude product. The residue was purified by column chromatography on silica gel using 25% EtOAC:n-Hexane, to obtain title compound (121 g, 310 mmol, 80% yield).

$^1$H NMR (400 MHz, DMSO-d₆): δ=11.35 (s, 1H), 6.78 (d, J=15.2 Hz, 1H), 6.44 (d, J=15.6 Hz, 1H), 3.42-3.36 (m, 2H), 1.99-1.92 (m, 1H), 1.88-1.59 (m, 3H), 1.49-1.36 (m, 21H); MS (ESI): m/z (%)=413.15 (90%) (M+Na), 389.15 (100%) (M−1).

Intermediate-5b: Preparation of tert-butyl (S,E)-2-(2-(N-(tert-butoxycarbonyl)sulfamoyl)vinyl)-2-methylpyrrolidine-1-carboxylate

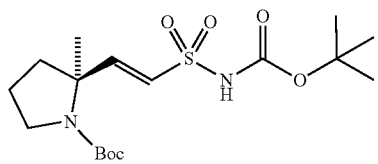 [SMILES: CC(C)(C)OC(=O)NS(=O)(=O)/C=C/[C@]1(C)CCCN1C(=O)OC(C)(C)C]

Intermediate-5b was also prepared as per the procedure described for synthesis of Intermediate-5a using tert-butyl (S)-2-formyl-2-methylpyrrolidine-1-carboxylate.

Intermediate-6a: Preparation of tert-butyl (R,E)-2-methyl-2-(2-sulfamoylvinyl)pyrrolidine-1-carboxylate

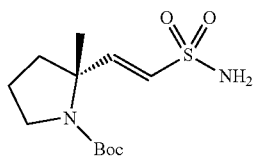 [SMILES: CC(C)(C)OC(=O)N1CCC[C@]1(C)/C=C/S(N)(=O)=O]

Intermediate 5a (121 g) was dissolved in DMSO (1200 mL) & heated to 85° C. (disappearance of the starting material was monitored by TLC). The reaction was cooled, poured into water (3000 mL) & extracted with EtOAc (2000 mL×4) & dried over Na₂SO₄. The solvent was concentrated in vacuo & purified by column chromatography on silica gel (50% EtOAc:n-Hexane) to give product (61.4 g, 211 mmol, 68.2% yield).

$^1$H NMR (400 MHz, DMSO-d₆): δ=6.98 (s, 2H), 6.61-6.49 (m, 1H), 6.25 (d, J=15.2 Hz, 1H), 3.43-3.35 (m, 2H), 1.99-1.66 (m, 4H), 1.47-1.43 (m, 3H), 1.40-1.37 (m, 9H); MS (ESI): m/z (%)=289.13 (100%) (M−1).

Intermediate-6b: Preparation of tert-butyl (S,E)-2-methyl-2-(2-sulfamoylvinyl)pyrrolidine-1-carboxylate

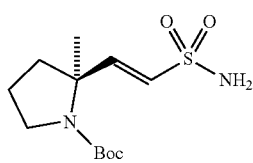 [SMILES: CC(C)(C)OC(=O)N1CCC[C@@]1(C)/C=C/S(N)(=O)=O]

Intermediate-6b was also prepared as per the procedure described for synthesis of Intermediate-6a using Intermediate-5b.

Intermediate-7a (Example 52): Preparation of tert-butyl (R,E)-2-(2-(N-((1,2,3,5,6,7-hexahydro-s-indacen-4-yl)carbamoyl)sulfamoyl)vinyl)-2-methylpyrrolidine-1-carboxylate

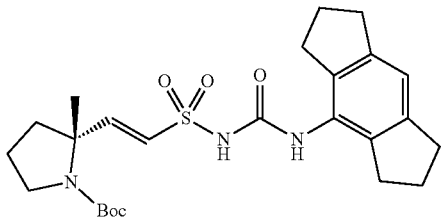 [SMILES: CC(C)(C)OC(=O)N1CCC[C@]1(C)/C=C/S(=O)(=O)NC(=O)Nc1c2c(cc3c1CCC3)CCC2]

To a solution of the tert-butyl (R,E)-2-methyl-2-(2-sulfamoylvinyl)pyrrolidine-1-carboxylate (Intermediate 6a) (61.0 gm, 210 mmol) in DMF (610 mL) at 0° C. was added NaH (60% dispersion in mineral oil) (10.08 gm, 252 mmol). The reaction was allowed to warm to r.t. and stirred for 30 minutes. 4-isocyanato-1,2,3,5,6,7-hexahydro-s-indacene (50.2 gm, 252 mmol) was added portion wise at 0° C. the reaction was warm to r.t. & stirred overnight. The reaction was acidified at 0° C. using 50% aq. citric acid up to pH=2.0 and diluted with cold water (3000 mL), precipitate was filtered through Buchner funnel & dried to give product (100 g, 204 mmol, 97% yield).

$^1$H NMR (400 MHz, DMSO-d₆): δ=10.41 (s, 1H), 8.06 (s, 1H), 6.96 (s, 1H), 6.87-6.77 (m, 1H), 6.55 (d, J=15.2 Hz), 3.43-3.37 (m, 2H), 2.81 (t, J=6.8 Hz, 4H), 2.67 (t, J=6.8 Hz, 4H), 2.00-1.93 (m, 5H), 1.86-1.65 (m, 3H), 1.41-1.43 (m, 3H), 1.40-1.38 (s, 9H); MS (ESI): m/z (%)=488.16 (100%) (M−1).

Intermediate-7b (Example 111): Preparation of tert-butyl (S,E)-2-(2-(N-((1,2,3,5,6,7-hexahydro-s-indacen-4-yl)carbamoyl)sulfamoyl)vinyl)-2-methylpyrrolidine-1-carboxylate

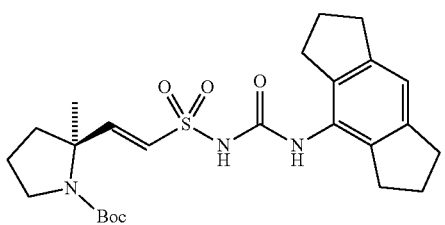 [SMILES: CC(C)(C)OC(=O)N1CCC[C@@]1(C)/C=C/S(=O)(=O)NC(=O)Nc1c2c(cc3c1CCC3)CCC2]

Intermediate-7b (Example 111) was also prepared as per the procedure described for synthesis of Intermediate-7a using Intermediate-6b.

Intermediate-8: Preparation of (diphenylphosphoryl)methanesulfonamide

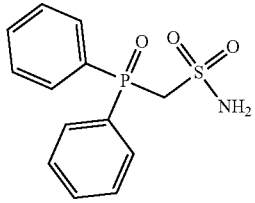 [SMILES: NS(=O)(=O)CP(=O)(c1ccccc1)c1ccccc1]

tert-butyl(((diphenylphosphoryl)methyl)sulfonyl)carbamate (Synthesis 2003, 15, 2321-24) (10.0 g, 25.3 mmol) was dissolved in DCM (100 mL) under $N_2$ atm. It was cooled to 0° C. temp. and added TFA (19.48 mL, 253 mmol) dropwise, after the addition ice bath was removed and RM was stirred further for 4 h. TLC was checked no starting material observed. The R.M was concentrated under reduced pressure and added water (50 mL) solid was ppt out, it was filtered and washed with water (25 mL×2) and dried over $P_2O_5$ to yield, (diphenylphosphoryl)methanesulfonamide (7.3 g, 24.72 mmol, 98% yield). $^1H$ NMR (400 MHz, DMSO-$d_6$): δ=7.86-7.81 (m, 4H), 7.61-7.51 (m, 6H), 6.84 (s, 2H), 4.63 (d, J=9.2 Hz, 2H); MS (ESI): m/z (%)=296.05 (100%) $(M+H)^+$.

Intermediate-9: Preparation of 1-(diphenylphosphoryl)-N-((1,2,3,5,6,7-hexahydro-s-indacen-4-yl)carbamoyl)methanesulfonamide

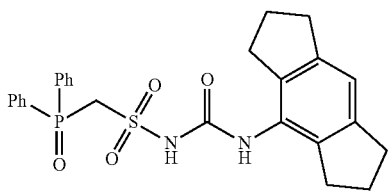 [SMILES: O=C(Nc1c2c(cc3c1CCC3)CCC2)NS(=O)(=O)CP(=O)(c1ccccc1)c1ccccc1]

(diphenylphosphoryl)methanesulfonamide [Intermediate 8] (6.0 g, 20.32 mmol) was taken in DMF (60 mL) under $N_2$ atm. it was cooled to 0° C. temp. and NaH (1.170 g, 24.38 mmol) was added and RM was stirred for 30 min. at RT. then a solution of 4-isocyanato-1,2,3,5,6,7-hexahydro-s-indacene (4.86 g, 24.38 mmol) in DMF (15 mL) was added and the RM was stirred further for 17 h at RT. TLC was checked no starting material observed. The reaction mixture was poured into ice cold water (180 mL) and acidified with sat. Citric acid, stirred and filtered to give crude product. It was purified by triturating in ethyl acetate gives, 1-(diphenylphosphoryl)-N-((1,2,3,5,6,7-hexahydro-s-indacen-4yl) carbamoyl)methanesulfonamide (9.1 g, 18.40 mmol, 91% yield).

$^1H$ NMR (400 MHz, DMSO-$d_6$): δ=10.4 (bs, 1H), 8.14 (s, 1H), 7.88-7.83 (m, 4H), 7.63-7.53 (m, 6H), 6.96 (s, 1H), 4.99 (d, J=8.8 Hz, 2H), 2.81 (t, J=7.2 Hz, 4H), 2.71 (t, J=7.2 Hz, 4H), 2.00-1.91 (m, 4H); MS (ESI): m/z (%)=495.14 (100%) $(M+H)^+$.

Intermediate-7b (Example 111): Preparation of tert-butyl (S,E)-2-(2-(N-((1,2,3,5,6,7-hexahydro-s-indacen-4-yl)carbamoyl)sulfamoyl) vinyl)-2-methylpyrrolidine-1-carboxylate

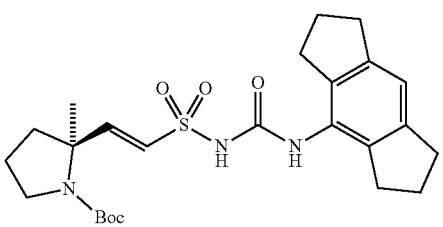 [SMILES: CC(C)(C)OC(=O)N1CCC[C@@]1(C)/C=C/S(=O)(=O)NC(=O)Nc1c2c(cc3c1CCC3)CCC2]

1-(diphenylphosphoryl)-N-((1,2,3,5,6,7-hexahydro-s-indacen-4-yl)carbamoyl)methanesulfonamide [Intermediate 9] (0.5 g, 1.011 mmol) was dissolved in DMF (5 mL) under N2 atm. It was cooled to 0° C. and added NaH (0.089 g, 2.224 mmol) under N2 atm at 0° C. After that ice bath was removed and RM was stirred at RT for 30 min. Then a solution of tert-butyl (S)-2-formyl-2-methylpyrrolidine-1-carboxylate (0.259 g, 1.213 mmol) in DMF (2.5 mL) was added dropwise to above suspension at −20° C. Then RM was warmed to RT & stirred further for 18 h. TLC was checked small amount of starting material observed. RM was diluted with water (15 mL), aqueous layer it was acidified with citric acid solution solid ppt, it was filtered off and washed with water (15 mL), dried under on P2O5. Crude product was purified by column chromatography using 40% EtOAc:Hexane to give tert-butyl (S,E)-2-(2-(N-((1,2,3,5,6,7-hexahydro-s-indacen-4-yl)carbamoyl)sulfamoyl)vinyl)-2-methylpyrrolidine-1-carboxylate (0.125 g, 0.255 mmol, 25.3% yield).

Intermediate-7a (Example 52) was also be prepared as per the procedure described for synthesis of Intermediate-7b (Example 111) using tert-butyl (R)-2-formyl-2-methylpyrrolidine-1-carboxylate.

Intermediate-3a (Example 10) was also be prepared as per the procedure described for synthesis of Intermediate-7b using tert-butyl (R)-2-formylpyrrolidine-1-carboxylate.

Intermediate-3b (Example 61) was also be prepared as per the procedure described for synthesis of Intermediate-7b using tert-butyl (S)-2-formylpyrrolidine-1-carboxylate.

Intermediate-10a: Preparation of tert-butyl 2-formylazetidine-1-carboxylate

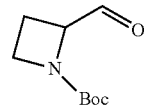

To a solution of 1-(tert-butyl) 2-methyl azetidine-1,2-dicarboxylate (European Journal of Medicinal Chemistry, 2000, 35(11), 979-988; Journal of the American Chemical Society (2010), 132(40), 14027-14029) (4.26 gm, 19.79 mmol) in dry DCM (86 mL) to give a solution. DIBAL-H (26.4 mL of 1.5M in Toluene, 39.6 mmol) was added dropwise at −78° C. The reaction mixture was stirred at −78° C. for 2 h then was quenched with methanol (5 mL) at −78° C. temperature. The reaction mixture was acidified with 50% citric acid solution up to pH=4.0. Water (100 mL) and DCM (50 mL) were added. The aqueous layer was extracted with DCM (2×80 mL). The combined organic layers was washed with water (150 mL), brine (10 mL), dried over Na$_2$SO$_4$ and solvent was evaporated to give a product tert-butyl 2-formylazetidine-1-carboxylate (3.4 gm, 18.36 mmol, 93% yield).

Intermediate-10b: Preparation of tert-butyl 2-formyl-2-methylazetidine-1-carboxylate

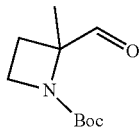

Intermediate-10b was also prepared as per the procedure described for synthesis of Intermediate-10a using 1-(tert-butyl) 2-methyl 2-methylazetidine-1,2-dicarboxylate.

Intermediate-11a: Preparation of tert-butyl (E)-2-(2-(N-(tert-butoxycarbonyl)sulfamoyl)vinyl)azetidine-1-carboxylate

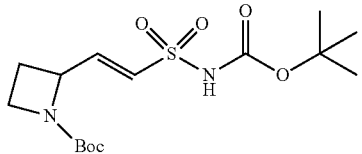 [SMILES: CC(C)(C)OC(=O)NS(=O)(=O)/C=C/C1CCN1C(=O)OC(C)(C)C]

To a solution of tert-butyl ((((diphenylphosphoryl)methyl)sulfonyl)carbamate (6.0 gm, 15.17 mmol) in DMF (60 mL) at 0° C. was added NaH (60% dispersion in mineral oil) (1.34 gm, 33.4 mmol). The reaction was allowed to warm to r.t. and stirred for 30 min. The tert-butyl 2-formylazetidine-1-carboxylate (3.37 g, 18.21 mmol) in DMF (35 mL) was added at dropwise at −20° C. the reaction was warm to r.t. & stirred overnight. The reaction was acidified using 50% aqueous citric acid (~10 mL) up to pH=2.0 the diluted with water (200 mL) & extracted with EtOAc (100 mL×3). The combined organic layer was washed with water (150 mL×3), brine (80 mL), dried over Na$_2$SO$_4$, concentrated & dried to give crude product. The residue was purified by column chromatography on silica gel using 30% EtOAC:n-Hexane to obtain tert-butyl (E)-2-(2-(N-(tert-butoxycarbonyl)sulfamoyl)vinyl)azetidine-1-carboxylate (1.8 g, 4.97 mmol, 33% yield).

$^1$H NMR (400 MHz, DMSO-d$_6$): δ=11.36 (s, 1H), 6.86 (d, J=15.2 Hz, J=5.6 Hz, 1H), 6.65 (d, J=14.8 Hz, 1H), 4.88-4.83 (m, 1H), 3.84-3.72 (m, 2H), 2.46-2.40 (m, 1H), 2.02-1.96 (m, 1H), 1.44 (s, 9H), 1.41 (s, 9H); MS (TOF): m/z (%)=385.2035 (100%) (M+Na), 361.1853 (100%) (M−1).

Intermediate-11: Preparation of tert-butyl (E)-2-(2-sulfamoylvinyl)azetidine-1-carboxylate tert-butyl

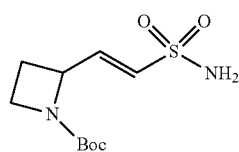 [SMILES: CC(C)(C)OC(=O)N1CCC1/C=C/S(N)(=O)=O]

(E)-2-(2-(N-(tert-butoxycarbonyl)sulfamoyl)vinyl)azetidine-1-carboxylate (Intermediate 11a) (1.8 g, 4.97 mmol) was dissolved in DMSO (18 mL) & heated to 85° C. (disappearance of the starting material was monitored by TLC). The reaction was cooled, poured into water (90 mL) & extracted with EtOAc (40 mL×4) & dried over Na$_2$SO$_4$. The solvent was concentrated in vacuo & purified by column chromatography on silica gel (60% EtOAc:n-Hexane) to give tert-butyl (E)-2-(2-sulfamoylvinyl)azetidine-1-carboxylate (2.02 g, 3.74 mmol, 83% yield).

$^1$H NMR (400 MHz, DMSO-d$_6$): δ=7.06 (s, 2H), 6.62-6.57 (m, 1H), 6.49 (dd, J=14.8 Hz, J=1.2 Hz, 1H), 4.81-4.76 (m, 1H), 3.81-3.71 (m, 2H), 2.41-2.37 (m, 1H), 2.00-1.93 (m, 1H), 1.38 (s, 9H); MS (TOF): m/z (%)=285.1431 (100%) (M+Na), 261.1290 (100%) (M−1).

Intermediate-12a: Preparation of tert-butyl (E)-2-(2-(N-(tert-butoxycarbonyl)sulfamoyl)vinyl)-2-methyl-azetidine-1-carboxylate

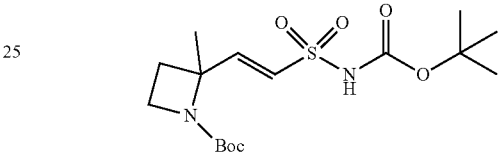

To a solution of tert-butyl ((((diphenylphosphoryl)methyl)sulfonyl)carbamate (4.5 gm, 11.38 mmol) in DMF (45 mL) at 0° C. was added NaH (60% dispersion in mineral oil) (1.00 gm, 25.04 mmol). The reaction was allowed to warm to r.t. and stirred for 30 min. tert-butyl 2-formyl-2-methyl-azetidine-1-carboxylate (*Journal of Medicinal Chemistry*, 2014, 57(23), 10044-10057) (2.72 gm, 13.66 mmol) in DMF (30 mL) was added at dropwise at −20° C. the reaction was warm to r.t. & stirred overnight. The reaction was acidified using 50% aqueous citric acid up to pH=2.0 the diluted with water (100 mL) & extracted with EtOAc (80 mL×3). The combined organic layer was washed with water (100 mL×3), brine (50 mL), dried over Na$_2$SO$_4$, concentrated & dried to give crude product. The residue was purified by column chromatography on silica gel using 30% EtOAC:n-Hexane to tert-butyl (E)-2-(2-(N-(tert-butoxycarbonyl)sulfamoyl)vinyl)-2-methylazetidine-1-carboxylate (3.73 g, 9.91 mmol, 87% yield). $^1$H NMR (400 MHz, DMSO-d$_6$): δ=11.39 (s, 1H), 6.94-6.88 (m, 1H), 6.63-6.56 (m, 1H), 3.75-3.71 (m, 1H), 3.66-3.63 (m, 1H), 2.21-2.11 (m, 2H), 1.44-1.41 (m, 9H), 1.38-136 (m, 9H); MS (ESI): m/z (%)=399.20 (100%) (M+Na), 375.20 (100%) (M−1).

Intermediate-12: Preparation of tert-butyl (E)-2-methyl-2-(2-sulfamoylvinyl)azetidine-1-carboxylate

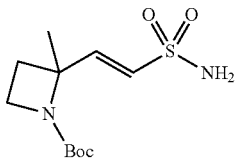 [SMILES: CC(C)(C)OC(=O)N1CCC1(C)/C=C/S(N)(=O)=O]

tert-butyl(E)-2-(2-(N-(tert-butoxycarbonyl)sulfamoyl)vinyl)-2-methylazetidine-1-carboxylate (Intermediate-12a)

(3.73 g, 9.91 mmol) was dissolved in DMSO (20 mL) & heated to 85° C. (disappearance of the starting material was monitored by TLC). The reaction was cooled, poured into water (70 mL) & extracted with EtOAc (30 mL×4) & dried over $Na_2SO_4$. The solvent was concentrated in vacuo & purified by column chromatography on silica gel (60% EtOAc:n-Hexane) to give tert-butyl (E)-2-methyl-2-(2-sulfamoylvinyl)azetidine-1-carboxylate (2.52 g, 9.12 mmol, 92% yield).

$^1$H NMR (400 MHz, DMSO-$d_6$): δ=7.06 (s, 2H), 6.68-6.61 (m, 1H), 6.46-6.40 (m, 1H), 3.82-3.60 (m, 2H), 2.19-1.99 (m, 2H), 1.50 (m, 3H), 1.39-1.37 (m, 9H); MS (ESI): m/z (%)=299.10 (100%) (M+Na), 275.05 (100%) (M−1).

Example-1

(R,E)-2-(1-ethylpyrrolidin-2-yl)-N-((1,2,3,5,6,7-hexahydro-s-indacen-4-yl)carbamoyl)-ethanesulfonamide

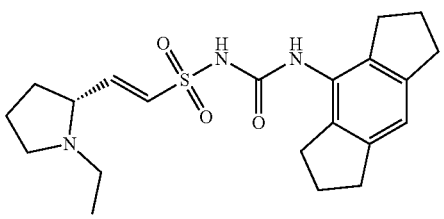 [SMILES: CCN1CCC[C@@H]1/C=C/S(=O)(=O)NC(=O)Nc1c2c(cc3c1CCC3)CCC2]

To solution of Intermediate 3 a (1 eq.) in DCM (2.5 mL) added TFA (1 eq.) at 0° C. The reaction was warmed to r.t. & stirred further for 3 h. The reaction mixture was concentrated in vacuo & purified by prep. HPLC to give product. To a solution of this product (1 eq.) in MeOH (7.0 mL) was added NaHCO$_3$ (1.2 eq.) at r.t. & stirred for 5 min. Acetaldehyde (5 eq.) was added at r.t. and stirred for 2 h. Thereafter reaction mixture was treated with NaBH$_4$ (1.5 eq.) portion wise at 0° C. then reaction mixture was allowed to warm to r.t. stirred overnight. The reaction mixture was purified by prep. HPLC to give pure product (Example 1).

Alternatively: To a solution of Intermediate 3 (1 eq.) in DCM (2.5 mL) added TFA (1 eq.) at 0° C. The reaction was warmed to r.t. & stirred further for 3 h. The reaction mixture was concentrated in vacuo & purified by prep. HPLC to give product. To a solution of this product (1 eq.) in dry THF (5.0 mL) was added NaH (1.2 eq.) at 0° C. & stirred for 5 min. Ethyl bromide (1.6 eq.) was added and stirred for 14 h at r.t. The reaction mixture was purified by prep. HPLC to give pure product (Example 1).

Alternatively: To a solution of (R,E)-tert-butyl 2-(2-(N-(tert-butoxycarbonyl)sulfamoyl)-vinyl)pyrrolidine-1-carboxylate (3.4 g, 9.04 mmol) in DCM was added trifluoro acetic acid (15.3 mL) and stirred for 1 h at room temperature. DCM was distilled and excess of trimethylamine (5.23 g, 7.2 mL, 53.1 mmol) was added to the reaction mixture at 0° C., followed by addition of ethyl bromide (1.35 g, 0.926 mL, 12.74 mmol). Crude mixture afforded (R,E)-2-(1-ethylpyrrolidin-2-yl)ethene-1-sulfonamide. To a solution of (R,E)-2-(1-ethylpyrrolidin-2-yl)ethene-1-sulfonamide (2.11 g, 10.33 mmol) in DMF (50 mL) under Nitrogen atmosphere conditions was added sodium hydride (60% in mineral oil) (0.5 g, 12.39 mmol) in one portion. The resulted suspension was stirred further for 1 h at room temperature. Further 4-isocyanato-1,2,3,5,6,7-hexahydro-s-indacene (2 g, 10.05 mmol) was added and reaction mixture (RM) was stirred rt for 16 h. The reaction mixture was concentrated under reduced pressure, and acidified with citric acid. Crude product was purified by preparative HPLC to give pure product (Example 1).

$^1$H NMR (400 MHz, DMSO-$d_6$): δ=8.03 (s, 1H), 6.92 (s, 1H), 6.87 (d, J=14.8 Hz, 1H), 6.60-6.54 (m, 1H), 3.27-3.16 (m, 3H), 2.80 (t, J=7.2 Hz, 4H), 2.67 (t, J=7.2 Hz, 4H), 2.35-2.33 (m, 2H), 2.09-1.94 (m, 6H), 1.81-1.73 (m, 2H), 1.03 (t, J=7.2 Hz, 3H); MS (ESI): m/z (%)=404.20 (100%) (M+H)$^+$.

Using appropriate starting materials and suitable modifications of the process described in example 1, including suitable addition and/or deletion of steps as may be necessary which are well within the scope of a person skilled in the art, the following compounds were prepared in an analogues manner.

Example-2

(S,E)-2-(1-ethylpyrrolidin-2-yl)-N-((1,2,3,5,6,7-hexahydro-s-indacen-4-yl)carbamoyl)-ethanesulfonamide

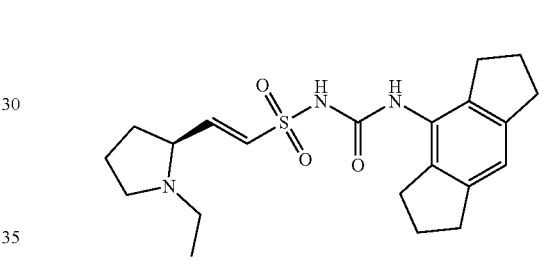

$^1$H NMR (400 MHz, DMSO-$d_6$): δ=8.03 (s, 1H), 6.92 (s, 1H), 6.87 (d, J=14.8 Hz, 1H), 6.60-6.54 (m, 1H), 3.27-3.16 (m, 3H), 2.80 (t, J=7.2 Hz, 4H), 2.67 (t, J=7.2 Hz, 4H), 2.35-2.33 (m, 2H), 2.09-1.94 (m, 6H), 1.81-1.73 (m, 2H), 1.03 (t, J=7.2 Hz, 3H); MS (ESI): m/z (%)=404.20 (100%) (M+H)$^+$.

Example-3

(R,E)-N-((1,2,3,5,6,7-hexahydro-s-indacen-4-yl)carbamoyl)-2-(pyrrolidin-2-yl)ethene-1-sulfonamide

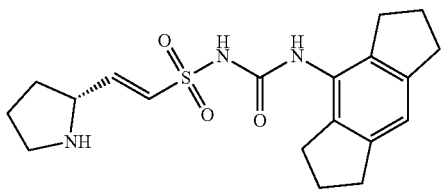 [SMILES: O=C(Nc1c2c(cc3c1CCC3)CCC2)NS(=O)(=O)/C=C/[C@H]1CCCN1]

$^1$H NMR (400 MHz, DMSO-$d_6$): δ=9.71 (brs, 1H), 7.49 (s, 1H), 6.95 (d, J=15.2 Hz, 1H), 6.80 (s, 1H), 6.36 (dd, J=7.2 Hz, J=15.2 Hz, 1H), 4.08-4.02 (m, 1H), 3.18-3.03 (m, 2H), 2.77 (t, J=7.2 Hz, 4H), 2.70 (t, J=7.2 Hz, 4H), 2.14-2.07 (m, 4H), 2.03-1.80 (m, 6H), 1.70-1.60 (m, 1H); MS (ESI): m/z (%)=376.10 (100%) (M+H)$^+$, 374.05 (100%) (M−1).

Example-4

(R,E)-N-((1,2,3,5,6,7-hexahydro-s-indacen-4-yl)carbamoyl)-2-(1-propylpyrrolidin-2-yl)ethene-1-sulfonamide

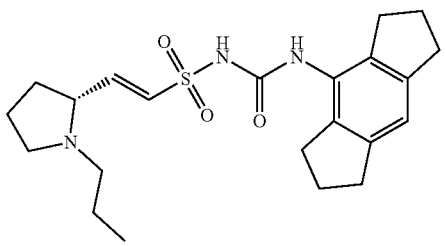 [SMILES: CCCN1CCC[C@@H]1/C=C/S(=O)(=O)NC(=O)Nc1c2c(cc3c1CCC3)CCC2]

¹H NMR (400 MHz, DMSO-d₆): δ=8.00 (s, 1H), 6.93 (s, 1H), 6.84 (d, J=14.8 Hz, 1H), 6.58 (dd, J=7.6 Hz, J=15.2 Hz, 1H), 3.15 (s, 1H), 2.80 (t, J=7.2 Hz, 4H), 2.67 (t, J=7.2 Hz, 4H), 2.33-2.22 (m, 2H), 2.09-1.91 (m, 6H), 1.78-1.73 (m, 2H), 1.62-1.50 (m, 1H), 1.46-1.33 (m, 2H), 0.82 (t, J=7.2 Hz, 3H); MS (ESI): m/z (%)=418.22 (100%) (M+H)⁺.

Example-5

(R,E)-2-(1-(cyclopropylmethyl)pyrrolidin-2-yl)-N-((1,2,3,5,6,7-hexahydro-s-indacen-4-yl)carbamoyl)ethene-1-sulfonamide

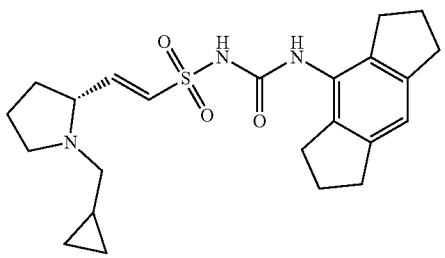 [SMILES: O=C(Nc1c2c(cc3c1CCC3)CCC2)NS(=O)(=O)/C=C/[C@H]1CCCN1CC1CC1]

¹H NMR (400 MHz, DMSO-d₆): δ=10.42 (brs, 1H), 8.03 (s, 1H), 6.93 (s, 1H), 6.87 (d, J=15.2 Hz, 1H), 6.62 (dd, J=7.2 Hz, J=15.2 Hz, 1H), 3.38-3.22 (m, 3H), 2.80 (t, J=7.2 Hz, 4H), 2.67 (t, J=7.2 Hz, 4H), 2.60-2.57 (m, 1H), 2.30-2.05 (m, 1H), 2.04-1.91 (m, 5H), 1.87-1.71 (m, 2H), 1.70-1.50 (m, 1H), 0.91-0.67 (m, 1H), 0.53-0.35 (m, 1H), 0.18-0.09 (m, 2H); MS (ESI): m/z (%)=430.20 (100%) (M+H)⁺, 428.11 (100%) (M−1).

Example-6

(R,E)-N-((1,2,3,5,6,7-hexahydro-s-indacen-4-yl)carbamoyl)-2-(1-methylpyrrolidin-2-yl)ethene-1-sulfonamide

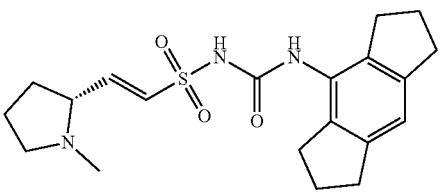 [SMILES: CN1CCC[C@@H]1/C=C/S(=O)(=O)NC(=O)Nc1c2c(cc3c1CCC3)CCC2]

To solution of Intermediate 3a (1 eq.) in DCM (2.5 mL) added TFA (1 eq.) at 0° C. The reaction was warmed to r.t. & stirred further for 3 h. The reaction mixture was concentrated in vacuo & purified by prep. HPLC to give product. To a solution of this product (1 eq.) in MeOH (7.0 mL) at r.t. was added Solid NaHCO₃ (1.2 eq.) & stirred for 5 min. Formaldehyde (37% solution) (5 eq.) was added at r.t. and stirred for 2 h. Thereafter reaction mixture was treated with NaBH₄ (1.5 eq.) portion wise at 0° C. then reaction mixture was allowed to warm to r.t. stirred overnight. The reaction mixture was purified by prep. HPLC to give pure product.

Alternatively, Example 6 was also be prepared as per the procedure described for synthesis of Intermediate-7b (Example 111) using Intermediate 9 and (R)-1-methylpyrrolidine-2-carbaldehyde, together with conventional techniques known to those skilled in the art of organic synthesis.

¹H NMR (400 MHz, DMSO-d₆): δ=10.53 (brs, 1H), 7.97 (s, 1H), 6.92 (s, 1H), 6.84 (d, J=15.2 Hz, 1H), 6.53 (dd, J=7.6 Hz, J=15.2 Hz, 1H), 3.13-3.04 (m, 1H), 3.05-2.92 (m, 1H), 2.80 (t, J=7.2 Hz, 4H), 2.67 (t, J=7.2 Hz, 4H), 2.33-2.28 (m, 1H), 2.26 (s, 3H), 2.05-1.91 (m, 5H), 1.79-1.72 (m, 2H), 1.59-1.54 (m, 1H); MS (ESI): m/z (%)=390.17 (100%) (M+H)⁺, 388.07 (30%) (M−1).

Example-7

(R,E)-N-((1,2,3,5,6,7-hexahydro-s-indacen-4-yl)carbamoyl)-2-(1-(methylsulfonyl)-pyrrolidin-2-yl)ethene-1-sulfonamide

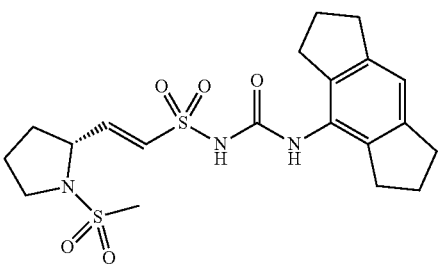 [SMILES: CS(=O)(=O)N1CCC[C@@H]1/C=C/S(=O)(=O)NC(=O)Nc1c2c(cc3c1CCC3)CCC2]

¹H NMR (400 MHz, DMSO-d₆): δ=10.55 (bs, 1H), 8.06 (s, 1H), 6.94 (s, 1H), 6.79-6.69 (m, 2H), 4.50-4.47 (m, 1H), 3.34-3.33 (m, 1H), 2.94 (s, 3H), 2.80 (t, J=7.2 Hz, 4H), 2.68 (t, J=7.6 Hz, 4H), 2.11-2.07 (m, 2H), 1.95 (quin, J=7.6 Hz, 4H), 1.88-1.85 (m, 1H), 1.80-1.79 (m, 2H); MS (ESI): m/z (%)=454.17 (100%) (M+H)⁺.

Example-8

(R,E)-2-(1-acetylpyrrolidin-2-yl)-N-((1,2,3,5,6,7-hexahydro-s-indacen-4-yl)carbamoyl)-ethene-1-sulfonamide

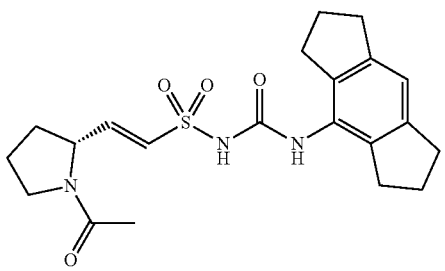 [SMILES: CC(=O)N1CCC[C@@H]1/C=C/S(=O)(=O)NC(=O)Nc1c2c(cc3c1CCC3)CCC2]

$^1$H NMR (400 MHz, DMSO-d$_6$): δ=10.25 (bs, 1H), 8.07 (s, 1H), 6.95 (s, 1H), 6.73-6.67 (m, 1H), 6.63 (d, J=15.2 Hz, 1H), 4.69-4.62 (m, 1H), 3.55-3.42 (m, 1H), 2.83 (t, J=7.2 Hz, 4H), 2.69 (q, J=7.2 Hz, 4H), 2.21-2.09 (m, 1H), 2.01-1.95 (m, 6H), 1.85 (s, 3H), 1.82-1.72 (m, 2H); MS (ESI): m/z (%)=418.20 (100%) (M+H)$^+$.

Example-9

(E)-2-(1-benzylpiperidin-4-yl)-N-((1,2,3,5,6,7-hexahydro-s-indacen-4-yl)carbamoyl)-ethanesulfonamide

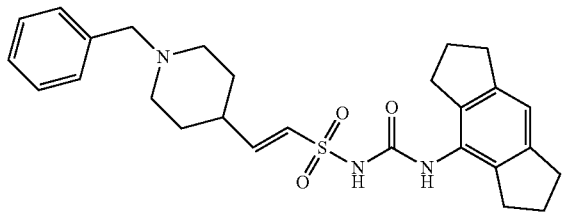 [SMILES: O=C(Nc1c2c(cc3c1CCC3)CCC2)NS(=O)(=O)/C=C/C1CCN(Cc2ccccc2)CC1]

$^1$H NMR (400 MHz, DMSO-d$_6$): δ=10.23 (br s, 1H), 8.02 (s, 1H), 7.35-7.25 (s, 5H), 6.94 (s, 1H), 6.76-6.63 (m, 2H), 3.55 (s, 2H), 2.89-2.69 (m, 6H), 2.65 (t, J=7.2 Hz, 4H), 2.30-2.27 (m, 1H), 2.12-2.07 (m, 2H), 2.00-1.91 (m, 4H), 1.71-1.69 (m, 2H), 1.43-1.38 (m, 2H); MS (ESI): m/z (%)=480.23 (100%) (M+H)$^+$.

Example-10 tert-butyl (R,E)-2-(2-(N-((1,2,3,5,6,7-hexahydro-s-indacen-4-yl)carbamoyl)sulfamoyl)-vinyl)pyrrolidine-1-carboxylate

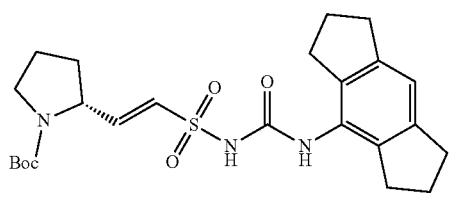 [SMILES: CC(C)(C)OC(=O)N1CCC[C@@H]1/C=C/S(=O)(=O)NC(=O)Nc1c2c(cc3c1CCC3)CCC2]

1H NMR (400 MHz, DMSO-d6): δ=10.42 (s, 1H), 8.09 (s, 1H), 6.96 (s, 1H), 6.71-6.68 (m, 1H), 6.59 (d, J=14.8 Hz, 1H), 4.45-4.38 (m, 1H), 3.29-3.27 (m, 2H), 2.79 (t, J=7.2 Hz, 4H), 2.65 (t, J=7.2 Hz, 4H), 2.30-1.93 (m, 5H), 1.78-1.71 (m, 3H), 1.39-1.33 (m, 9H); MS (ESI): m/z (%)=498.18 (40%) (M+Na)+, 474.18 (100%) (M−1).

Example-11

(R,E)-N-((1,2,3,5,6,7-hexahydro-s-indacen-4-yl)carbamoyl)-2-(1-(2-methoxyethyl)pyrrolidin-2-yl)ethenesulfonamide

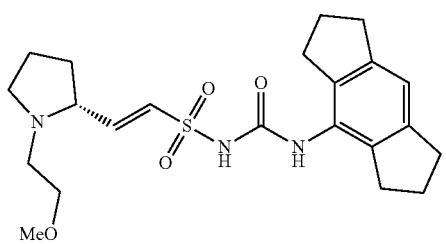 [SMILES: COCCN1CCC[C@@H]1/C=C/S(=O)(=O)NC(=O)Nc1c2c(cc3c1CCC3)CCC2]

1H NMR (400 MHz, DMSO-d6): δ=7.38 (s, 1H), 6.77 (s, 1H), 6.67 (d, J=15.2 Hz, 1H), 6.04 (dd, J1=8.0 Hz, J2=15.2 Hz, 1H), 3.37 (t, J=6.0 Hz, 2H), 3.37 (s, 3H), 3.13-3.10 (m, 1H), 2.82-2.74 (m, 6H), 2.69 (t, J=7.2 Hz, 4H), 2.22-2.13 (m, 2H), 1.95-1.93 (m, 5H), 1.76-1.67 (m, 2H), 1.48-1.41 (m, 1H); MS (ESI): m/z (%)=434.19 (100%) (M+H)+.

Example-12

(R,E)-N-((1,2,3,5,6,7-hexahydro-s-indacen-4-yl)carbamoyl)-2-(1-(isopropylsulfonyl)pyrrolidin-2-yl)ethenesulfonamide

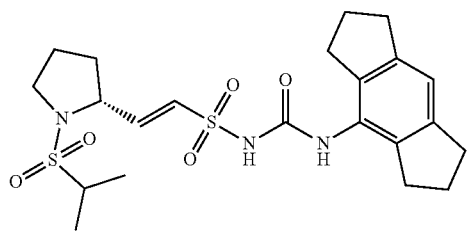 [SMILES: CC(C)S(=O)(=O)N1CCC[C@@H]1/C=C/S(=O)(=O)NC(=O)Nc1c2c(cc3c1CCC3)CCC2]

$^1$H NMR (400 MHz, DMSO-d$_6$): δ=7.34 (s, 1H), 6.77 (s, 1H), 6.67 (d, J=15.2 Hz, 1H), 6.20-6.19 (m, 1H), 4.39 (bs, 1H), 3.46 (q, J=9.6 Hz, 1H), 3.29-3.24 (m, 2H), 2.76 (t, J=7.2 Hz, 4H), 2.70 (t, J=7.2 Hz, 4H), 2.09-2.04 (m, 1H), 1.93 (t, J=7.2 Hz, 4H), 1.87 (t, J=8.4 Hz, 4H), 1.73-1.69 (m, 1H), 1.19 (d, J=6.4 Hz, 6H); MS (ESI): m/z (%)=482.13 (65%) (M+H)$^+$, 504.10 (100%) (M+Na)$^+$;

Example-13

(R,E)-2-(1-((3-fluorophenyl)sulfonyl)pyrrolidin-2-yl)-N-((1,2,3,5,6,7-hexahydro-s-indacen-4-yl)carbamoyl)ethenesulfonamide

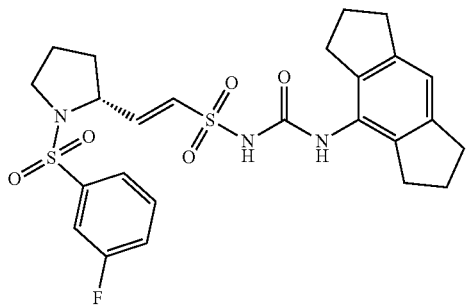 [SMILES: O=C(Nc1c2c(cc3c1CCC3)CCC2)NS(=O)(=O)/C=C/[C@H]1CCCN1S(=O)(=O)c1cccc(F)c1]

$^1$H NMR (400 MHz, DMSO-d$_6$): δ=10.46 (s, 1H), 8.07 (s, 1H), 7.71-7.70 (m, 3H), 7.62-7.58 (m, 1H), 6.95 (s, 1H), 6.90 (d, J=14.8 Hz, 1H), 6.74 (dd, J$_1$=5.6 Hz, J$_2$=15.2 Hz 1H), 4.49 (t, J=5.6 Hz, 1H), 3.42-3.38 (m, 1H), 3.18-3.14 (m, 1H), 2.80 (t, J=7.6 Hz, 4H), 2.69 (t, J=7.2 Hz, 4H), 1.96 (quin, J=7.2 Hz, 4H), 1.76-1.60 (m, 3H), 1.55-1.52 (m, 1H); MS (ESI): m/z (%)=534.18 (100%) (M+H)$^+$;

Example-14

(R,E)-N-((1,2,3,5,6,7-hexahydro-s-indacen-4-yl)carbamoyl)-2-(1-(pyrazine-2-carbonyl)pyrrolidin-2-yl)ethenesulfonamide

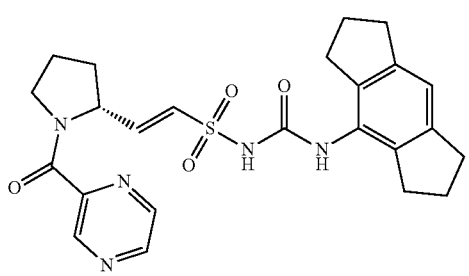 [SMILES: O=C(Nc1c2c(cc3c1CCC3)CCC2)NS(=O)(=O)/C=C/[C@H]1CCCN1C(=O)c1cnccn1]

$^1$H NMR (400 MHz, DMSO-d$_6$): δ=10.46 (s, 1H), 8.95-8.88 (m, 1H), 8.78-8.65 (m, 1H), 8.70-8.57 (m, 1H), 8.04 (s, 1H), 6.93 (s, 1H), 6.76 (d, J=15.6 Hz, 1H), 6.95 (d, J=15.2 Hz, 1H), 4.93-4.90 (m, 1H), 3.84-3.81 (m, 1H), 3.66-3.59 (m, 1H), 2.82 (t, J=8.0 Hz, 4H), 2.66 (t, J=7.6 Hz, 4H), 2.16-1.97 (m, 1H), 1.95-1.78 (m, 7H); MS (ESI): m/z (%)=482.16 (100%) (M+H)$^+$.

Example-15

(R,E)-2-(2-(N-((1,2,3,5,6,7-hexahydro-s-indacen-4-yl)carbamoyl)sulfamoyl)vinyl)pyrrolidine-1-carboxamide

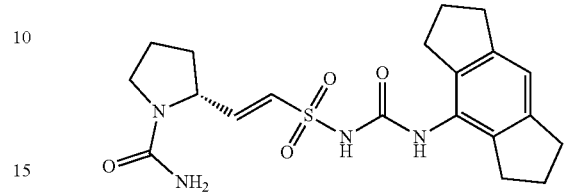

$^1$H NMR (400 MHz, DMSO-d$_6$): δ=7.95 (s, 1H), 6.91 (s, 1H, 6.58-6.52 (m, 2H), 5.77 (s, 2H), 4.51-4.48 (m, 1H), 3.25-3.21 (m, 1H), 2.80 (t, J=7.2 Hz, 4H), 2.68 (t, J=6.8 Hz, 4H), 2.00-1.91 (m, 6H), 1.81-1.69 (m, 3H); MS (ESI): m/z (%)=419.16 (100%) (M+H)$^+$.

Example-16

(R,E)-2-(1-(cyclopropanecarbonyl)pyrrolidin-2-yl)-N-((1,2,3,5,6,7-hexahydro-s-indacen-4-yl)carbamoyl)ethene-1-sulfonamide

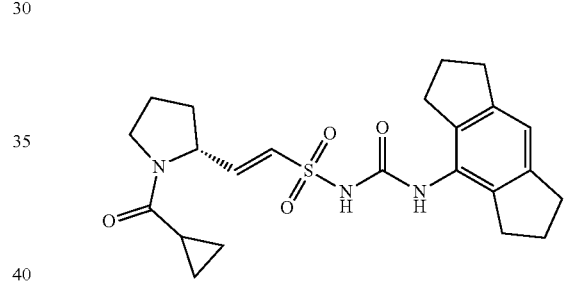

$^1$H NMR (400 MHz, DMSO-d$_6$): δ=10.45 (s, 1H), 8.11 (d, J=14.4 Hz, 1H), 6.96 (s, 1H), 6.87-6.52 (m, 2H), 4.97-4.65 (m, 1H), 3.76-3.61 (m, 1H), 3.41-3.32 (m, 1H), 2.81 (t, J=7.2 Hz, 4H), 2.67 (q, J=6.0 Hz, 4H), 2.17-2.16 (m, 1H), 2.02-1.95 (m, 5H), 1.88-1.74 (m, 3H), 1.76-0.69 (m, 2H), 0.66-0.59 (m, 2H); MS (ESI): m/z (%)=444.15 (100%) (M+H)$^+$.

Example-17

(R,E)-N-((1,2,3,5,6,7-hexahydro-s-indacen-4-yl)carbamoyl)-2-(1-(2,2,2-trifluoroacetyl)pyrrolidin-2-yl)ethene-1-sulfonamide

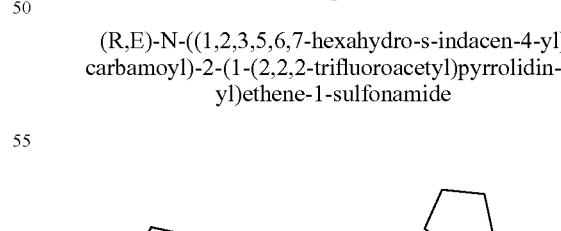

$^1$H NMR (400 MHz, DMSO-d$_6$): δ=10.45 (s, 1H), 8.03 (s, 1H), 6.94 (s, 1H), 6.76-6.67 (m, 2H), 4.80 (bs, 1H), 3.75 (bs,

1H), 3.67-3.54 (m, 1H), 2.80 (t, J=7.6 Hz, 4H), 2.67 (t, J=6.4 Hz, 4H), 2.15-2.5 (m, 1H), 2.00-1.91 (m, 6H), 1.81-1.76 (m, 1H); MS (ESI): m/z (%)=472.14 (100%) (M−H)⁺.

Example-18

(R,E)-N-((1,2,3,5,6,7-hexahydro-s-indacen-4-yl)carbamoyl)-2-(1-(2-(methylthio)ethyl)pyrrolidin-2-yl)ethene-1-sulfonamide

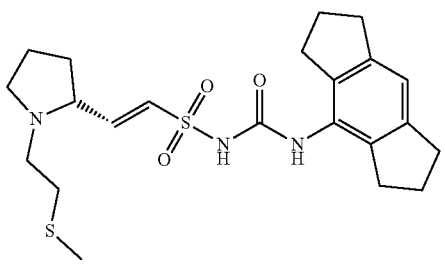

¹H NMR (400 MHz, DMSO-d₆): δ=10.38 (s, 1H), 8.06 (s, 1H), 6.95 (s, 1H), 6.91 (d, J=14.8 Hz, 1H), 6.68 (d, J=15.2 Hz, 1H), 3.21-3.12 (m, 2H), 2.81 (t, J=7.2 Hz, 5H), 2.68 (t, J=7.2 Hz, 5H), 2.46-2.40 (m, 1H), 2.33-2.24 (m, 1H), 2.09-1.91 (m, 9H), 1.74-1.70 (m, 2H), 1.54-1.49 (m, 1H); MS (ESI): m/z (%)=450.14 (100%) (M+H)⁺.

Example-19

(R,E)-N-((1,2,3,5,6,7-hexahydro-s-indacen-4-yl)carbamoyl)-2-(1-(2,2,2-trifluoroethyl)pyrrolidin-2-yl)ethene-1-sulfonamide ¹H NMR (400 MHz, DMSO-d₆): δ=7.91 (s, 1H), 6.88 (s, 1H), 6.76 (d, J=15.2 Hz, 1H), 6.41 (dd, J₁=7.2 Hz, J₂, 14.8, 1H), 3.34-3.21 (m, 1H), 3.16-3.09 (m, 2H), 2.78 (t, J=7.2 Hz, 4H), 2.67 (t, J=7.2 Hz, 4H), 2.59-2.54 (m, 1H), 2.02-1.91 (m, 6H), 1.80-1.75 (m, 2H), 1.57-1.48 (m, 1H); MS (ESI): m/z (%)=458.15 (100%) (M+H)⁺.

Example-20

(R,E)-N-((1,2,3,5,6,7-hexahydro-s-indacen-4-yl)carbamoyl)-2-(1-isobutylpyrrolidin-2-yl)ethene-1-sulfonamide

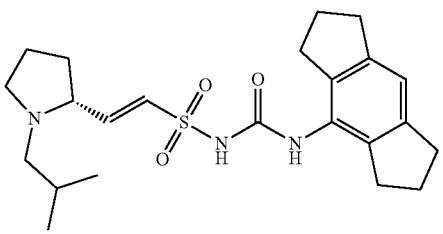 [SMILES: CC(C)CN1CCC[C@@H]1/C=C/S(=O)(=O)NC(=O)Nc1c2c(cc3c1CCC3)CCC2]

¹H NMR (400 MHz, DMSO-d₆): δ=10.4 (brs, 1H), 8.00 (s, 1H), 6.92 (s, 1H), 6.80 (d, J=15.2 Hz, 1H), 6.56 (dd, J=15.2 Hz, J=6.8 Hz, 1H), 3.12-3.00 (m, 3H), 2.80 (t, J=7.2 Hz, 4H), 2.68 (t, J=7.2 Hz, 4H), 2.25-2.14 (m, 2H), 2.10-2.04 (m, 2H), 1.99-1.91 (m, 4H), 1.76-1.65 (m, 2H), 1.55-1.48 (m, 1H), 0.85 (t, J=6.8 Hz, 3H), 0.79 (d, J=6.4 Hz, 3H); MS (ESI): m/z (%)=432.21 (100%) (M+H)⁺.

Example-21

(R,E)-2-(1-(ethylsulfonyl)pyrrolidin-2-yl)-N-((1,2,3,5,6,7-hexahydro-s-indacen-4-yl)carbamoyl)ethene-1-sulfonamide

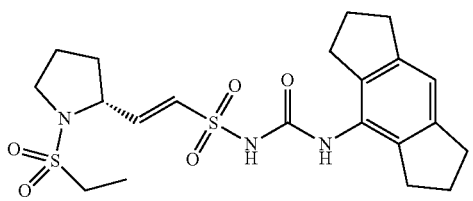 [SMILES: CCS(=O)(=O)N1CCC[C@@H]1/C=C/S(=O)(=O)NC(=O)Nc1c2c(cc3c1CCC3)CCC2]

¹H NMR (400 MHz, DMSO-d₆): δ=10.39 (brs, 1H), 8.01 (s, 1H), 7.38 (s, 1H), 6.77 (d, J=15.2 Hz, 1H), 6.68 (dd, J=15.2 Hz, J=5.2 Hz, 1H), 4.63-4.39 (m, 1H), 3.38-3.33 (m, 2H), 3.09-2.97 (m, 2H), 2.80 (t, J=7.2 Hz, 4H), 2.68 (t, J=7.2 Hz, 4H), 2.15-2.04 (m, 1H), 2.00-1.91 (m, 4H), 1.88-1.77 (m, 3H), 1.19 (t, J=7.2 Hz, 3H); MS (ESI): n/z (%)=468.12 (100%) (M+H)⁺.

Example-22

(R,E)-N-((1,2,3,5,6,7-hexahydro-s-indacen-4-yl)carbamoyl)-2-(1-isopropylpyrrolidin-2-yl)ethene-1-sulfonamide

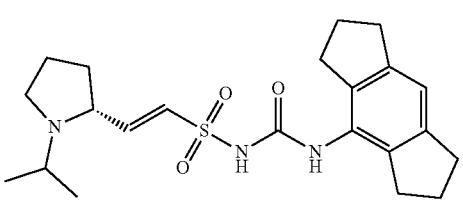 [SMILES: CC(C)N1CCC[C@@H]1/C=C/S(=O)(=O)NC(=O)Nc1c2c(cc3c1CCC3)CCC2]

¹H NMR (400 MHz, DMSO-d₆): δ=10.23 (brs, 1H), 7.96 (s, 1H), 6.92 (s, 1H), 6.89 (d, J=15.2 Hz, 1H), 6.61 (d, J=15.2 Hz, J=7.2 Hz, 1H), 2.98-2.85 (m, 2H), 2.80 (t, J=7.2 Hz, 4H), 2.67 (t, J=7.2 Hz, 4H), 2.51-2.50 (m, 1H), 2.02-1.91 (m, 6H), 1.75-1.73 (m, 2H), 1.61-1.56 (m, 1H), 1.04 (d, J=6.4 Hz, 3H), 0.99 (d, J=6.4 Hz, 3H); MS (ESI): m/z (%)=418.21 (100%) (M+H)⁺, 416.18 (100%) (M−1).

Example-23

(R,E)-N-((1,2,3,5,6,7-hexahydro-s-indacen-4-yl)carbamoyl)-2-(1-(3-(methylsulfonyl)propyl)pyrrolidin-2-yl)ethenesulfonamide

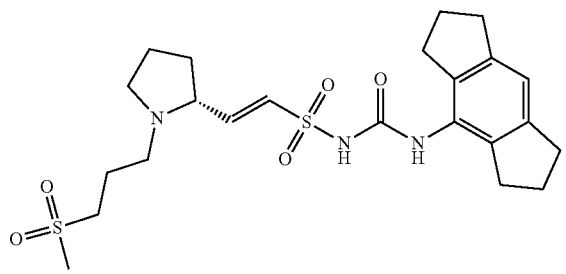 [SMILES: CS(=O)(=O)CCCN1CCC[C@@H]1/C=C/S(=O)(=O)NC(=O)Nc1c2c(cc3c1CCC3)CCC2]

¹H NMR (400 MHz, DMSO-d₆): δ=10.37 (brs, 1H), 8.08 (s, 1H), 6.95 (s, 1H), 6.82 (d, J=14.8 Hz, 1H), 6.61 (d, J=14.8 Hz, J=7.2 Hz, 1H), 3.13-3.06 (m, 3H), 2.98-2.91 (m, 1H), 2.86 (s, 3H), 2.67 (t, J=7.2 Hz, 4H), 2.81 (t, J=7.2 Hz, 4H), 2.33-2.28 (m, 1H), 2.27-2.20 (m, 1H), 2.03-1.91 (m, 6H), 1.83-1.72 (m, 4H), 1.57-1.50 (m, 1H); MS (ESI): m/z (%)=496.16 (100%) (M+H)⁺, 494.15 (100%) (M−1).

Example-24

(R,E)-2-(1-benzoylpyrrolidin-2-yl)-N-((1,2,3,5,6,7-hexahydro-s-indacen-4-yl)carbamoyl)ethenesulfonamide

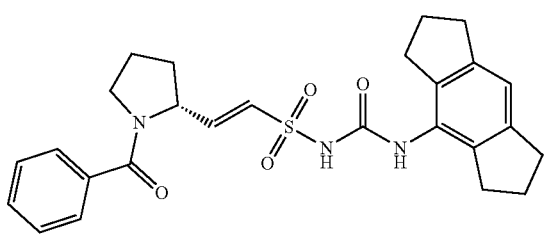 [SMILES: O=C(Nc1c2c(cc3c1CCC3)CCC2)NS(=O)(=O)/C=C/[C@H]1CCCN1C(=O)c1ccccc1]

¹H NMR (400 MHz, DMSO-d₆): δ=10.41 (brs, 1H), 8.03 (s, 1H), 7.54-7.30 (m, 5H), 6.93 (s, 1H), 6.80-6.50 (m, 2H), 4.85-4.49 (m, 1H), 3.62-3.36 (m, 2H), 2.78 (t, J=6.8 Hz, 4H), 2.66 (t, J=6.8 Hz, 4H), 2.19-2.08 (m, 1H), 1.94-1.90 (m, 4H), 1.82-1.76 (m, 3H); MS (ESI): m/z (%)=480.17 (100%) (M+H)⁺, 478.15 (100%) (M−1).

Example-25

(R,E)-N-((2-(1-benzoylpyrrolidin-2-yl)vinyl)sulfonyl)-N-((1,2,3,5,6,7-hexahydro-s-indacen-4-yl)carbamoyl)benzamide

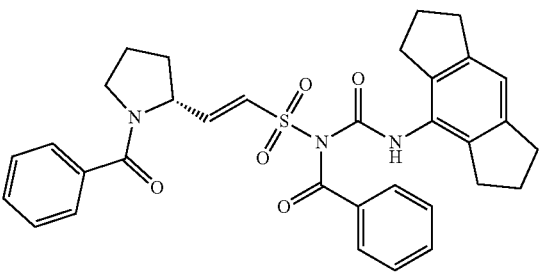 [SMILES: O=C(c1ccccc1)N1CCC[C@@H]1/C=C/S(=O)(=O)N(C(=O)Nc1c2c(cc3c1CCC3)CCC2)C(=O)c1ccccc1]

¹H NMR (400 MHz, DMSO-d₆): δ=7.61-7.52 (m, 2H), 7.47-7.32 (m, 8H), 7.22-7.09 (m, 1H), 6.97 (s, 1H), 6.56 (d, J=14.4 Hz, 1H), 6.31 (d, J=14.4 Hz, 1H), 4.76-4.37 (m, 1H), 3.78-3.42 (m, 1H), 2.84-2.67 (m, 8H), 2.10-2.05 (m, 1H), 1.95-1.91 (m, 4H), 1.84-1.76 (m, 3H), 1.68-1.64 (m, 1H); MS (ESI): m/z (%)=584.19 (100%) (M+H)⁺, 606.17 (50%) (M+Na), 582.17 (10%) (M−1).

Example-26

(R,E)-N-((1,2,3,5,6,7-hexahydro-s-indacen-4-yl)carbamoyl)-2-(pyrrolidin-2-yl)ethenesulfonamide

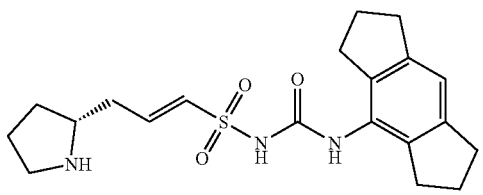 [SMILES: O=C(Nc1c2c(cc3c1CCC3)CCC2)NS(=O)(=O)/C=C/C[C@H]1CCCN1]

¹H NMR (400 MHz, DMSO-d₆): δ=7.54 (s, 1H), 6.81 (s, 1H), 6.70 (d, J=15.2 Hz, 1H), 6.33-6.26 (m, 1H), 3.53-3.46 (m, 2H), 3.15-3.00 (m, 3H), 2.77 (t, J=7.2 Hz, 4H), 2.70 (t, J=7.2 Hz, 4H), 2.03-1.81 (m, 7H), 1.62-1.43 (m, 1H); MS (ESI): m/z (%)=390.16 (100%) (M+H)⁺, 388.14 (100%) (M−1).

Example-27

(R,E)-N-((1,2,3,5,6,7-hexahydro-s-indacen-4-yl)carbamoyl)-2-(1-(thiophene-3-carbonyl)pyrrolidin-2-yl)ethenesulfonamide

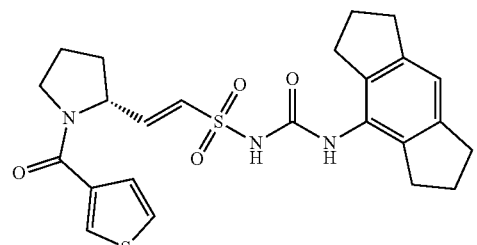

¹H NMR (400 MHz, DMSO-d₆): δ=10.36 (brs, 1H), 8.01 (s, 1H), 7.58-7.48 (m, 1H), 7.36-7.22 (m, 1H), 6.93 (s, 1H), 6.81-6.56 (m, 2H), 4.83-4.74 (m, 1H), 3.78-3.67 (m, 1H), 3.66-3.52 (m, 1H), 2.79 (t, J=7.2 Hz, 4H), 2.66 (t, J=6.8 Hz, 4H), 2.15-1.76 (m, 8H); MS (ESI): m/z (%)=486.13 (100%) (M+H)⁺, 484.11 (100%) (M−1).

Example-28

(R,E)-N-((1,2,3,5,6,7-hexahydro-s-indacen-4-yl)carbamoyl)-2-(pyrrolidin-2-yl)ethene-1-sulfonamide methane sulfonate

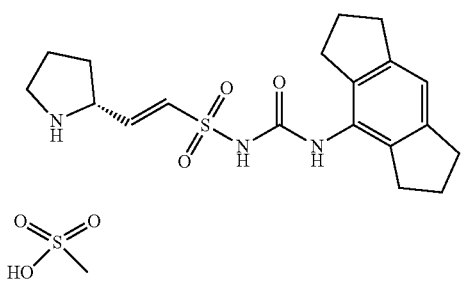

Procedure: To solution of (R,E)-N-((1,2,3,5,6,7-hexahydro-s-indacen-4-yl)carbamoyl)-2-(pyrrolidin-2-yl)ethene-1-sulfonamide (0.105 g, 0.28 mmol) in EtOH (2.0 mL) was added Methanesulfonic acid (27 mg, 0.280 mmol) at r.t. The reaction was refluxed for 1 h then cooled to r.t. precipitate was formed, then filtered through Buchner funnel, dried in vacuo to give product.

¹H NMR (400 MHz, DMSO-d₆): δ=10.59 (brs, 1H), 9.05 (brs, 2H), 8.27 (s, 1H), 7.13 (d, J=15.2 Hz, 1H), 6.97 (s, 1H), 6.90-6.85 (m, 1H), 4.32-4.30 (m, 1H), 3.32-3.12 (m, 2H), 3.99-3.78 (m, 4H), 3.75-3.66 (m, 4H), 2.37 (s, 1H), 2.28-2.12 (m, 1H), 2.10-1.88 (m, 6H), 1.27-1.22 (m, 1H); MS (ESI): m/z (%)=376.10 (100%) (M+H)⁺.

Example-29

(R,E)-N-((1,2,3,5,6,7-hexahydro-s-indacen-4-yl)carbamoyl)-2-(pyrrolidin-2-yl)ethene-1-sulfonamide maleate

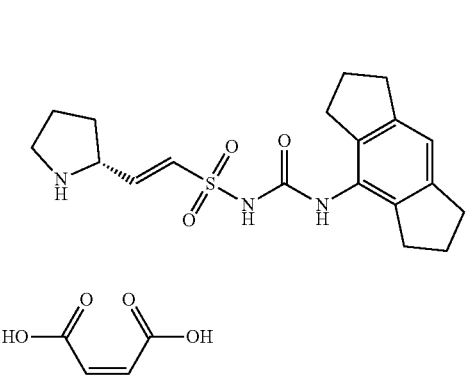 [SMILES: O=C(Nc1c2c(cc3c1CCC3)CCC2)NS(=O)(=O)/C=C/[C@H]1CCCN1 ; O=C(O)/C=C\C(=O)O]

Procedure:—To solution of (R,E)-N-((1,2,3,5,6,7-hexahydro-s-indacen-4-yl)carbamoyl)-2-(pyrrolidin-2-yl)ethene-1-sulfonamide (0.2 g, 0.533 mmol) in EtOH (4.0 mL) was added Maleic acid (0.124 g, 1.07 mmol) at r.t. The reaction was refluxed for 30 min. then cooled to r.t. precipitate was formed, then filtered through Buchner funnel, dried in vacuo to give product.

¹H NMR (400 MHz, DMSO-d₆): δ=9.06 (brs, 1H), 8.15 (s, 1H), 7.12 (d, J=15.6 Hz, 1H), 6.96 (s, 1H), 6.87-6.82 (m, 1H), 6.03 (s, 2H), 4.29-4.03 (m, 4H), 3.57-3.23 (m, 2H), 2.98-2.83 (m, 4H), 2.85-2.69 (m, 4H), 2.26-2.10 (m, 1H), 2.09-1.83 (m, 6H), 1.82-1.63 (m, 1H); MS (ESI): m/z (%)=376.15 (100%) (M+H)⁺.

Example-30

(R,Z)—N-((1,2,3,5,6,7-hexahydro-s-indacen-4-yl)carbamoyl)-2-(pyrrolidin-2-yl)ethene-1-sulfonamide

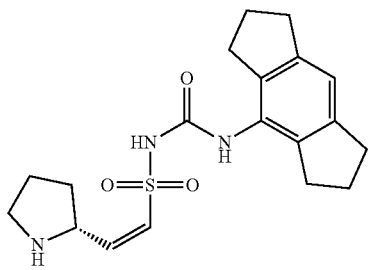 [SMILES: O=C(Nc1c2c(cc3c1CCC3)CCC2)NS(=O)(=O)/C=C\[C@H]1CCCN1]

¹H NMR (400 MHz, DMSO-d₆): δ=9.70 (brs, 1H), 7.94 (s, 1H), 6.83 (s, 1H), 6.36 (dd, J=11.6 Hz, J=1.6 Hz, 1H), 5.82 (dd, J=11.2 Hz, J=6.0 Hz, 1H), 4.95-4.94 (m, 1H), 3.17-3.03 (m, 1H), 2.99-2.89 (m, 1H), 2.79-2.63 (m, 9H), 2.03-1.76 (m, 8H); MS (ESI): m/z (%)=376.16 (60%) (M+H)⁺.

Example-31

(S,E)-N-((1,2,3,5,6,7-hexahydro-s-indacen-4-yl)carbamoyl)-3-(pyrrolidin-2-yl)prop-1-ene-1-sulfonamide

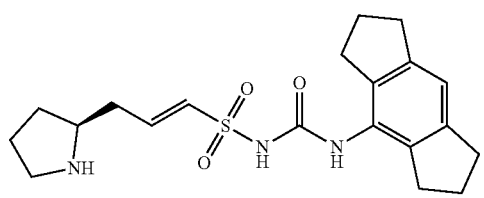 [SMILES: O=C(Nc1c2c(cc3c1CCC3)CCC2)NS(=O)(=O)/C=C/C[C@@H]1CCCN1]

Procedure:—To solution of corresponding N-Boc derivatives (0.20 g, 0.408 mmol) in DCM (2.5 mL) added TFA (0.315 mL, 4.08 mmol) at 0° C. The reaction was warmed to r.t. & stirred further for 3 h. The reaction mixture was concentrated in vacuo & purified by prep. HPLC to give product.

¹H NMR (400 MHz, DMSO-d₆): δ=7.54 (s, 1H), 6.80 (s, 1H), 6.69 (d, J=15.2 Hz, 1H), 6.29-6.25 (m, 1H), 3.52-3.44 (m, 2H), 3.17-3.02 (m, 3H), 2.77 (t, J=7.2 Hz, 4H), 2.70 (t, J=7.2 Hz, 4H), 2.01-1.76 (m, 8H), 1.53-1.50 (m, 1H); MS (ESI): m/z (%)=390.16 (100%) (M+H)⁺.

Example-32

(R,E)-2-(1-(cyclohexylsulfonyl)pyrrolidin-2-yl)-N-((1,2,3,5,6,7-hexahydro-s-indacen-4-yl)carbamoyl)ethene-1-sulfonamide

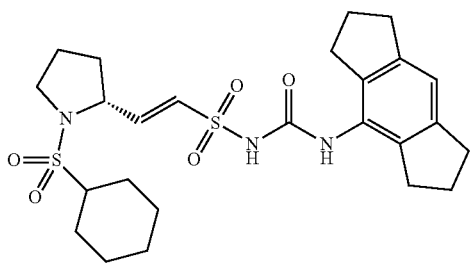 [SMILES: O=C(Nc1c2c(cc3c1CCC3)CCC2)NS(=O)(=O)/C=C/[C@H]1CCCN1S(=O)(=O)C1CCCCC1]

$^1$H NMR (400 MHz, DMSO-d$_6$): δ=10.4 (brs, 1H), 8.04 (s, 1H), 6.94 (s, 1H), 6.78 (d, J=15.2 Hz, 1H), 6.69 (dd, J=15.2 Hz, J=6.0 Hz, 1H), 4.57-4.53 (m, 1H), 3.45-3.39 (m, 1H), 3.31-3.27 (m, 1H), 3.14-3.08 (m, 1H), 2.80 (t, J=7.2 Hz, 4H), 2.68 (t, J=7.2 Hz, 4H), 2.17-2.09 (m, 1H), 2.00-1.91 (m, 5H), 1.88-1.60 (m, 5H), 1.55-1.52 (m, 1H), 1.40-1.00 (m, 6H); MS (ESI): m/z (%)=522.20 (100%) (M+H)$^+$, 544.25 (100%) (M+Na), 520.15 (100%) (M−1).

Example-33

(R,Z)—N-((1,2,3,5,6,7-hexahydro-s-indacen-4-yl)carbamoyl)-2-(1-methylpyrrolidin-2-yl)ethene-1-sulfonamide

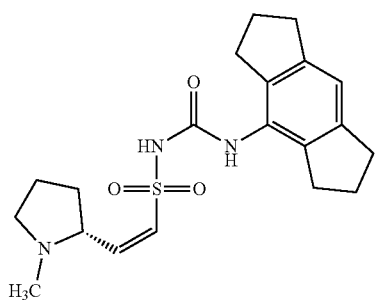 [SMILES: CN1CCC[C@@H]1/C=C\S(=O)(=O)NC(=O)Nc1c2c(cc3c1CCC3)CCC2]

$^1$H NMR (400 MHz, DMSO-d$_6$): δ=7.85 (s, 1H), 6.84 (s, 1H), 6.52 (dd, J=11.2 Hz, J=1.2 Hz, 1H), 5.84 (dd, J=11.2 Hz, J=8.0 Hz, 1H), 4.54-4.53 (m, 1H), 3.24-3.18 (m, 2H), 2.77 (t, J=7.2 Hz, 4H), 2.70 (t, J=7.2 Hz, 4H), 2.56 (s, 3H), 2.33-2.18 (m, 1H), 1.99-1.91 (m, 8H), 1.85-1.70 (m, 1H); MS (ESI): m/z (%)=390.20 (100%) (M+H)$^+$, 388 (100%) (M−1).

Example-34

(R,E)-2-(1-(cyclohexylmethyl)pyrrolidin-2-yl)-N-((1,2,3,5,6,7-hexahydro-s-indacen-4-yl)carbamoyl)ethene-1-sulfonamide $^1$H NMR (400 MHz, DMSO-d$_6$): δ=10.38 (brs, 1H), 8.06 (s, 1H), 6.94 (s, 1H), 6.82 (d, J=14.8 Hz, 1H), 6.62 (dd, J=15.2 Hz, J=6.8 Hz, 1H), 3.00-3.17 (m, 2H), 2.80 (t, J=7.2 Hz, 4H), 2.68 (t, J=7.2 Hz, 4H), 2.40-2.28 (m, 1H), 2.26-2.13 (m, 1H), 2.12-1.90 (m, 6H), 1.89-1.82 (m, 1H), 1.81-1.67 (m, 2H), 1.66-1.47 (m, 5H), 1.45-1.30 (m, 1H), 1.28-0.92 (m, 3H), 0.78-0.69 (m, 2H); MS (ESI): m/z (%)=472.29 (100%) (M+H)$^+$.

Example-35

(R,E)-2-(1-cyclohexylpyrrolidin-2-yl)-N-((1,2,3,5,6,7-hexahydro-s-indacen-4-yl)carbamoyl)ethene-1-sulfonamide

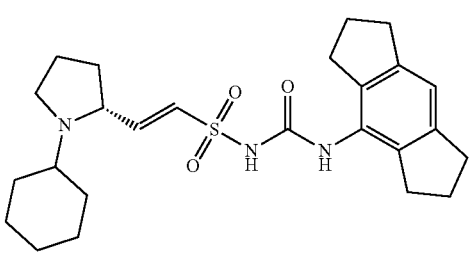 [SMILES: O=C(Nc1c2c(cc3c1CCC3)CCC2)NS(=O)(=O)/C=C/[C@H]1CCCN1C1CCCCC1]

$^1$H NMR (400 MHz, DMSO-d$_6$): δ=10.38 (brs, 1H), 8.01 (s, 1H), 6.92 (s, 1H), 6.85 (d, J=15.2 Hz, 1H), 6.65 (dd, J=14.4 Hz, J=6.4 Hz, 1H), 3.90-3.62 (m, 1H), 3.09-2.96 (m, 1H), 2.80 (t, J=7.2 Hz, 4H), 2.70-2.67 (m, 5H), 1.99-1.91 (m, 6H), 1.83-1.63 (m, 7H), 1.58-1.50 (m, 1H), 1.27-1.02 (m, 5H); MS (ESI): m/z (%)=458.29 (100%) (M+H)$^+$.

Example-36

(R,E)-N-((1,2,3,5,6,7-hexahydro-s-indacen-4-yl)carbamoyl)-2-(1-(1-methylpiperidin-4-yl)pyrrolidin-2-yl)ethene-1-sulfonamide

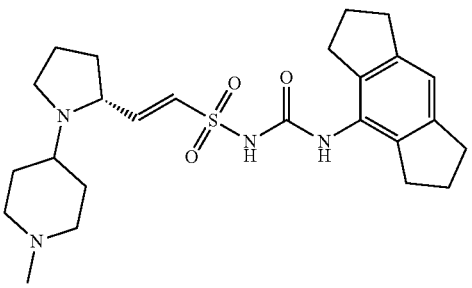 [SMILES: CN1CCC(N2CCC[C@@H]2/C=C/S(=O)(=O)NC(=O)Nc2c3c(cc4c2CCC4)CCC3)CC1]

¹H NMR (400 MHz, DMSO-d₆): δ=7.46 (s, 1H), 7.29 (s, 1H), 6.77 (s, 1H), 6.64 (d, J=15.2 Hz, 1H), 6.11 (dd, J=15.2 Hz, J=8.0 Hz, 1H), 3.35-3.30 (m, 1H), 2.84-2.80 (m, 1H), 2.76 (t, J=7.2 Hz, 4H), 2.72-2.68 (m, 5H), 2.34-2.29 (m, 1H), 2.09 (s, 3H), 1.95-1.88 (m, 4H), 1.85-1.77 (m, 4H), 1.76-1.60 (m, 4H), 1.50-1.35 (m, 3H); MS (ESI): m/z (%)=473.32 (100%) (M+H)⁺.

Example-37

(R,Z)—N-((1,2,3,5,6,7-hexahydro-s-indacen-4-yl)carbamoyl)-2-(1-isopropylpyrrolidin-2-yl)ethene-1-sulfonamide

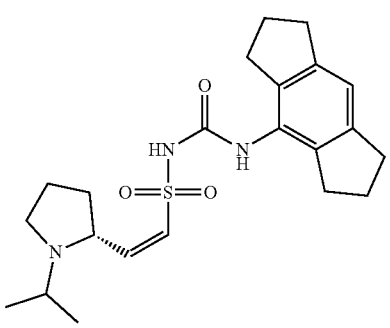 [SMILES: CC(C)N1CCC[C@@H]1/C=C\S(=O)(=O)NC(=O)Nc1c2c(cc3c1CCC3)CCC2]

¹H NMR (400 MHz, DMSO-d₆): δ=10.14 (brs, 1H), 7.73 (s, 1H), 6.85 (s, 1H), 6.59 (d, J=11.2 Hz, 1H), 6.04-5.99 (m, 1H), 4.91-4.89 (m, 1H), 3.48-3.45 (m, 1H), 3.26-3.20 (m, 1H), 3.17-3.01 (m, 1H), 2.78 (t, J=7.2 Hz, 4H), 2.69 (t, J=7.2 Hz, 4H), 2.25-2.18 (m, 1H), 1.97-1.85 (m, 6H), 1.75-1.66 (m, 1H), 1.22 (d, J=6.8 Hz, 3H), 1.17 (t, J=6.4 Hz, 3H); MS (ESI): m/z (%)=418.23 (100%) (M+H)⁺, 416.21 (100%) (M−1).

Example-38

(R,E)-N-((1,2,3,5,6,7-hexahydro-s-indacen-4-yl)carbamoyl)-2-(1-(tetrahydro-2H-pyran-4-yl)pyrrolidin-2-yl)ethene-1-sulfonamide

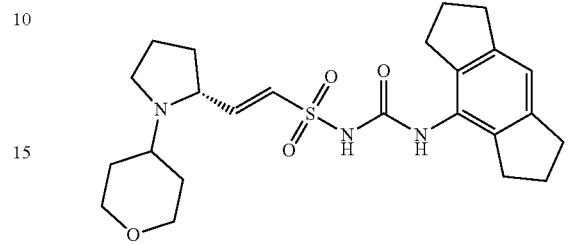

¹H NMR (400 MHz, DMSO-d₆): δ=10.30 (brs, 1H), 8.05 (s, 1H), 6.95 (s, 1H), 6.85 (d, J=15.2 Hz, 1H), 6.70 (dd, J=14.8 Hz, J=6.4 Hz, 1H), 3.83-3.73 (m, 2H), 3.69-3.59 (m, 1H), 3.23-3.15 (m, 2H), 3.03-2.91 (m, 1H), 2.80 (t, J=7.2 Hz, 4H), 2.67 (t, J=7.2 Hz, 4H), 2.58-2.53 (m, 2H), 2.00-1.91 (m, 5H), 1.71-1.62 (m, 3H), 1.58-1.52 (m, 2H), 1.42-1.33 (m, 2H); MS (ESI): m/z (%)=460.30 (100%) (M+H)⁺.

Example-39

(R,E)-N-((1,2,3,5,6,7-hexahydro-s-indacen-4-yl)carbamoyl)-2-(1-(oxetan-3-yl)pyrrolidin-2-yl)ethene-1-sulfonamide

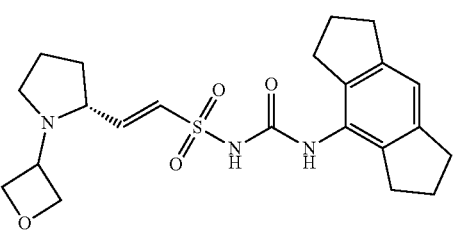

¹H NMR (400 MHz, DMSO-d₆): δ=10.41 (brs, 1H), 8.10 (s, 1H), 6.96 (s, 1H), 6.83 (d, J=14.8 Hz, 1H), 6.61 (dd, J=15.2 Hz, J=8.0 Hz, 1H), 4.51-4.44 (m, 2H), 4.43-4.38 (m, 2H), 3.81-3.74 (m, 1H), 3.23-3.17 (m, 1H), 3.00-2.95 (m, 1H), 2.81 (t, J=7.2 Hz, 4H), 2.68 (t, J=7.2 Hz, 4H), 2.41-2.33 (m, 1H), 2.01-1.91 (m, 5H), 1.78-1.71 (m, 2H), 1.62-1.55 (m, 1H); MS (ESI): m/z (%)=432.22 (100%) (M+H)⁺.

Example-40

(R,E)-N-((1,2,3,5,6,7-hexahydro-s-indacen-4-yl)carbamoyl)-2-(1-(tetrahydro-2H-thiopyran-4-yl)pyrrolidin-2-yl)ethene-1-sulfonamide

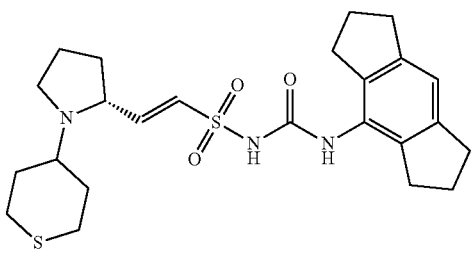 [SMILES: O=C(Nc1c2c(cc3c1CCC3)CCC2)NS(=O)(=O)/C=C/[C@H]1CCCN1C1CCOCC1]

$^1$H NMR (400 MHz, DMSO-d$_6$): δ=10.32 (brs, 1H), 8.06 (s, 1H), 6.95 (s, 1H), 6.84 (d, J=14.8 Hz, 1H), 6.64 (dd, J=14.8 Hz, J=6.4 Hz, 1H), 3.71-3.58 (m, 1H), 2.98-2.87 (m, 1H), 2.81 (t, J=7.2 Hz, 4H), 2.68 (t, J=7.2 Hz, 4H), 2.63-2.58 (m, 2H), 2.54-2.51 (m, 2H), 2.48-2.38 (m, 2H), 2.13-2.01 (m, 1H), 1.99-1.89 (m, 6H), 1.76-1.62 (m, 2H), 1.58-1.45 (m, 3H); MS (ESI): m/z (%)=476.24 (100%) (M+H)$^+$.

Example-41

(R,E)-N-((1,2,3,5,6,7-hexahydro-s-indacen-4-yl)carbamoyl)-2-(1-(thiazol-2-ylmethyl)pyrrolidin-2-yl)ethene-1-sulfonamide

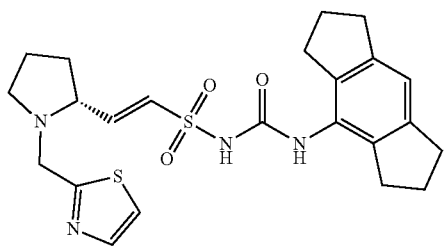 [SMILES: O=C(Nc1c2c(cc3c1CCC3)CCC2)NS(=O)(=O)/C=C/[C@H]1CCCN1Cc1nccs1]

$^1$H NMR (400 MHz, DMSO-d$_6$): δ=10.33 (brs, 1H), 8.08 (s, 1H), 7.71 (d, J=3.2 Hz, 1H), 6.41 (d, J=3.2 Hz, 1H), 6.92-6.86 (m, 2H), 6.70 (dd, J=15.2 Hz, J=6.8 Hz, 1H), 4.04 (d, J=14.8 Hz, 1H), 3.78 (d, J=14.8 Hz, 1H), 3.44-3.39 (m, 1H), 3.07-3.02 (m, 1H), 2.77 (t, J=6.8 Hz, 4H), 2.61 (t, J=6.8 Hz, 4H), 2.43-2.33 (m, 1H), 2.08-1.97 (m, 1H), 1.96-1.87 (m, 4H), 1.80-1.74 (m, 2H), 1.63-1.57 (m, 1H); MS (ESI): m/z (%)=473.19 (100%) (M+H)$^+$

Example-42

(E)-N-((1,2,3,5,6,7-hexahydro-s-indacen-4-yl)carbamoyl)-2-(piperidin-4-yl)ethenesulfonamide

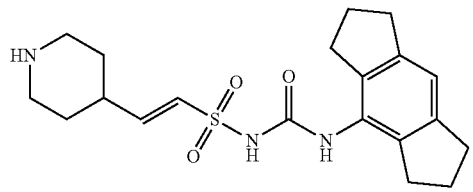 [SMILES: O=C(Nc1c2c(cc3c1CCC3)CCC2)NS(=O)(=O)/C=C/C1CCNCC1]

$^1$H NMR (400 MHz, DMSO-d$_6$): δ=10.55 (s, 1H), 8.78 (s, 1H), 8.26 (s, 2H), 6.95 (s, 1H), 6.79-6.70 (m, 2H), 3.29 (d, J=11.2 Hz, 2H), 2.80 (t, J=6.8 Hz, 4H), 2.66 (t, J=6.4 Hz, 4H), 1.95 (t, J=6.8 Hz, 4H), 1.90 (d, J=13.2 Hz, 2H); MS (ESI): m/z (%)=390.20 (100%) (M+H)$^+$.

Example-43

(E)-N-((1,2,3,5,6,7-hexahydro-s-indacen-4-yl)carbamoyl)-2-(1-methylpiperidin-4-yl)ethenesulfonamide

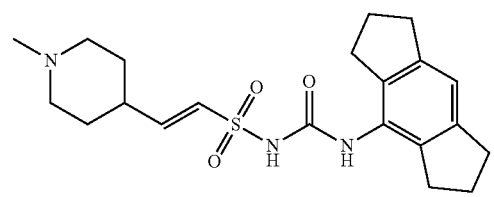 [SMILES: CN1CCC(/C=C/S(=O)(=O)NC(=O)Nc2c3c(cc4c2CCC4)CCC3)CC1]

$^1$H NMR (400 MHz, DMSO-d$_6$): δ=7.80 (s, 1H), 6.86 (s, 1H), 6.64 (s, 1H), 6.60 (d, J=16.4 Hz, 1H), 6.48 (dd, J$_1$=6.0 Hz, J$_2$=15.2 Hz 1H), 3.03-2.99 (m, 3H), 2.78 (t, J=7.6 Hz, 4H), 2.68 (t, J=7.6 Hz, 4H), 2.38 (s, 3H), 2.36-2.24 (m, 2H), 1.94 (t, J=7.2 Hz, 4H), 1.77-1.74 (m, 2H), 1.47-1.37 (m, 2H); MS (ESI): m/z (%)=404.20 (100%) (M+H)$^+$.

Example-44

(E)-N-((1,2,3,5,6,7-hexahydro-s-indacen-4-yl)carbamoyl)-2-(1-(methylsulfonyl)piperidin-4-yl)ethenesulfonamide

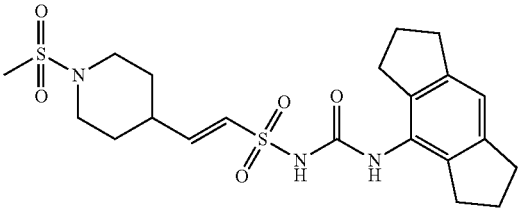 [SMILES: CS(=O)(=O)N1CCC(/C=C/S(=O)(=O)NC(=O)Nc2c3c(cc4c2CCC4)CCC3)CC1]

$^1$H NMR (400 MHz, DMSO-d$_6$): δ=10.37 (bs, 1H), 8.11 (s, 1H), 6.96 (s, 1H), 6.78-6.7 (m, 2H), 3.57 (d, J=12.0 Hz, 2H), 2.85 (s, 3H), 2.81 (t, J=7.2 Hz, 4H), 2.75-2.67 (m, 6H), 1.97 (t, J=7.2 Hz, 4H), 1.82 (d, J=11.6 Hz, 2H), 1.45-1.37 (m, 2H); MS (ESI): m/z (%)=468.12 (100%) (M+H)$^+$.

Example-45

(E)-2-(1-acetylpiperidin-4-yl)-N-((1,2,3,5,6,7-hexahydro-s-indacen-4-yl)carbamoyl)ethene-sulfonamide

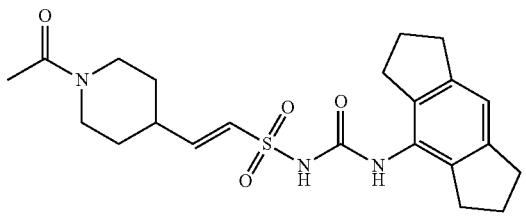 [SMILES: CC(=O)N1CCC(/C=C/S(=O)(=O)NC(=O)Nc2c3c(cc4c2CCC4)CCC3)CC1]

$^1$H NMR (400 MHz, DMSO-d$_6$): δ=10.38 (bs, 1H), 8.04 (s, 1H), 6.94 (s, 1H), 6.64 (dd, J$_1$=5.6 Hz, J$_2$=15.6 Hz, 1H), 6.68 (d, J=15.6 Hz, 1H), 4.33 (d, J=13.3 Hz, 1H), 3.81 (d, J=14.4 Hz, 1H), 3.06 (t, J=12.0 Hz, 1H), 2.80 (t, J=7.2 Hz, 4H), 2.67 (t, J=7.2 Hz, 4H), 2.63-2.56 (m, 2H), 2.00-1.91 (m, 7H), 1.72 (t, J=15.6 Hz, 2H), 1.35-1.24 (m, 1H), 1.21-1.11 (m, 1H); MS (ESI): m/z (%)=432.17 (100%) (M+H)$^+$.

Example-46 tert-butyl(E)-4-(2-(N-((1,2,3,5,6,7-hexahydro-s-indacen-4-yl)carbamoyl)sulfamoyl)vinyl)-piperidine-1-carboxylate

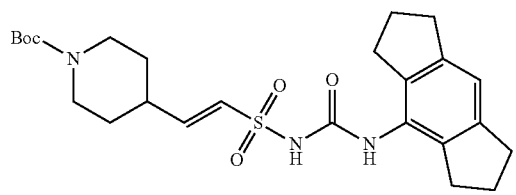 [SMILES: CC(C)(C)OC(=O)N1CCC(/C=C/S(=O)(=O)NC(=O)Nc2c3c(cc4c2CCC4)CCC3)CC1]

$^1$H NMR (400 MHz, DMSO-d$_6$): δ=10.37 (bs, 1H), 8.05 (s, 1H), 6.96 (s, 1H), 6.8 (dd, J$_1$=6.0 Hz, J$_2$=15.2 Hz, 1H), 6.69 (d, J=15.6 Hz, 1H), 3.93 (d, J=11.6 Hz, 2H), 2.81 (t, J=7.2 Hz, 6H), 2.66 (t, J=6.8 Hz, 4H), 1.97 (t, J=7.2 Hz, 4H), 1.71 (d, J=11.6 Hz, 2H), 1.39 (s, 9H), 1.23-1.17 (m, 3H); MS (ESI): m/z (%)=488.18 (100%) (M−H)$^+$.

Example-47

(E)-2-(1-ethylpiperidin-4-yl)-N-((1,2,3,5,6,7-hexahydro-s-indacen-4-yl)carbamoyl)ethene-1-sulfonamide

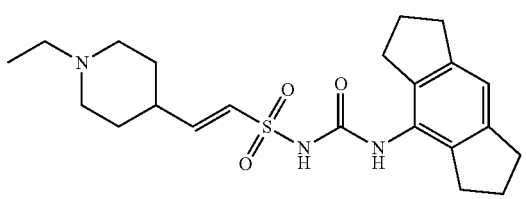 [SMILES: CCN1CCC(/C=C/S(=O)(=O)NC(=O)Nc2c3c(cc4c2CCC4)CCC3)CC1]

$^1$H NMR (400 MHz, DMSO-d$_6$): δ=7.87 (s, 1H), 6.94 (s, 1H), 6.65 (d, J=15.6 Hz, 1H), 6.52 (dd, J$_1$=6.0 Hz, J$_2$=15.2 Hz, 1H), 3.16 (d, J=11.6 Hz, 3H), 2.79 (t, J=7.2 Hz, 4H), 2.73-2.67 (m, 6H), 1.98-1.91 (m, 5H), 1.82-1.75 (m, 3H), 1.52-1.44 (m, 2H), 1.10 (t, J=7.2 Hz, 3H), MS (ESI): m/z (%)=418.18 (100%) (M+H)$^+$, 416.17 (100%) (M−1)$^-$.

Example-48

(R,E)-2-(1-ethylpyrrolidin-3-yl)-N-((1,2,3,5,6,7-hexahydro-s-indacen-4-yl)carbamoyl)-ethenesulfonamide

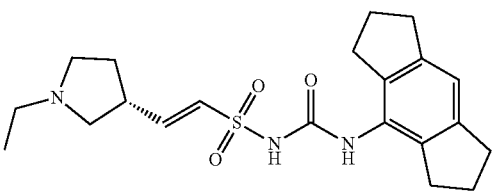 [SMILES: CCN1CC[C@H](/C=C/S(=O)(=O)NC(=O)Nc2c3c(cc4c2CCC4)CCC3)C1]

$^1$H NMR (400 MHz, DMSO-d$_6$): δ=7.95 (s, 1H), 6.43 (s, 1H), 6.60 (d, J=14.4 Hz, 1H), 6.55-6.45 (m, 1H), 3.18 (d, J=4.8 Hz, 2H), 3.05-2.95 (m, 4H), 0.2.79 (t, J=7.2 Hz, 4H), 2.73-2.67 (m, 5H), 1.95 (t, J=7.2 Hz, 4H), 1.55 (t, J=7.2 Hz, 3H), 1.09 (t, J=7.2 Hz, 2H); MS (ESI): m/z (%)=404.18 (100%) (M+H)$^+$.

Example-49

(R,E)-1,1-diethyl-3-(2-(N-((1,2,3,5,6,7-hexahydro-s-indacen-4-yl)carbamoyl)sulfamoyl)-vinyl)pyrrolidin-1-ium bromide

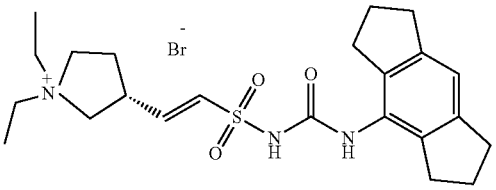

$^1$H NMR (400 MHz, DMSO-d$_6$): δ=7.27 (s, 1H), 6.77 (s, 1H), 6.73 (s, 1H), 6.27 (dd, J;=6.8 Hz, J$_2$=15.6 Hz, 1H), 5.59 (bs, 1H), 4.12 (s, 1H), 3.78-3.72 (m, 2H), 3.62 (t, J=7.6 Hz, 1H), 3.54 (t, J=8.0 Hz, 1H), 3.41-3.36 (m, 2H), 3.30-3.24 (m, 2H), 2.76-2.69 (m, 8H), 2.33-2.25 (m, 1H), 1.93-2.90 (m, 4H), 1.20 (t, J=6.8 Hz, 6H); MS (ESI): m/z (%)=432.20 (100%) (M)$^+$.

Example-50

(E)-N-((1,2,3,5,6,7-hexahydro-s-indacen-4-yl)carbamoyl)-2-(pyrrolidin-3-yl)ethene-sulfonamide

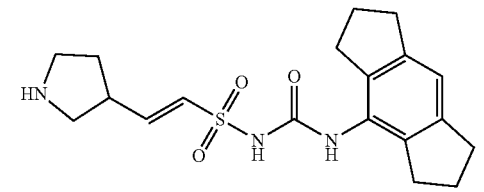 [SMILES: O=C(Nc1c2c(cc3c1CCC3)CCC2)NS(=O)(=O)/C=C/C1CCNC1]

¹H NMR (400 MHz, DMSO-d₆): δ=7.41 (s, 1H), 6.78 (s, 1H), 6.64 (d, J=15.6 Hz, 1H), 6.23 (dd, J₁=7.6 Hz, J₂=15.2 Hz, 1H), 3.18-3.14 (m, 1H), 2.99-2.95 (m, 1H), 2.76 (t, J=7.6 Hz, 4H), 2.70 (t, J=7.2 Hz, 4H), 2.00-1.97 (m, 2H), 1.95 (t, J=7.6 Hz, 4H), 1.90-1.88 (m, 2H), 1.76-1.54 (m, 1H); MS (ESI): m/z (%)=376.15 (100%) (M+H)⁺.

Example-51

(R,E)-N-((1,2,3,5,6,7-hexahydro-s-indacen-4-yl)carbamoyl)-2-(2-methylpyrrolidin-2-yl)ethene-1-sulfonamide

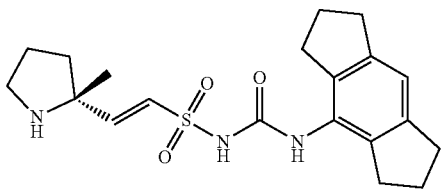 [SMILES: C[C@]1(/C=C/S(=O)(=O)NC(=O)Nc2c3c(cc4c2CCC4)CCC3)CCCN1]

¹H NMR (400 MHz, DMSO-d₆): δ=7.56 (s, 1H), 6.91 (d, J=15.6 Hz, 1H), 6.82 (s, 1H), 6.52 (d, J=15.2 Hz, 1H), 3.23-3.19 (m, 2H), 3.14-3.07 (m, 1H), 2.77 (t, J=7.6 Hz, 4H), 2.69 (t, J=7.2 Hz, 4H), 1.96-1.87 (m, 8H), 1.79-1.74 (m, 1H), 1.34 (s, 3H); MS (ESI): m/z (%)=390.14 (100%) (M+H)⁺.

Example-52 tert-butyl(R,E)-2-(2-(N-((1,2,3,5,6,7-hexahydro-s-indacen-4-yl)carbamoyl)sulfamoyl)vinyl)-2-methylpyrrolidine-1-carboxylate

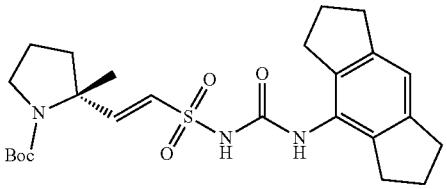 [SMILES: CC(C)(C)OC(=O)N1CCC[C@]1(C)/C=C/S(=O)(=O)NC(=O)Nc1c2c(cc3c1CCC3)CCC2]

¹H NMR (400 MHz, DMSO-d₆): δ=10.41 (s, 1H), 8.05 (s, 1H), 6.95 (s, 1H), 6.87 (d, J=16.0 Hz, 1H), 6.56 (d, J=15.6 Hz, 1H), 3.38-3.32 (m, 2H), 2.82 (t, J=7.6 Hz, 4H), 2.75 (t, J=7.2 Hz, 4H), 1.95 (t, J=7.2 Hz, 5H), 1.86-1.69 (m, 3H), 1.48-1.41 (m, 3H), 1.34 (s, 9H); MS (ESI): m/z (%)=488.16 (100%) (M−H)⁺.

Example-53

(R,E)-2-(1-acetyl-2-methylpyrrolidin-2-yl)-N-((1,2,3,5,6,7-hexahydro-s-indacen-4-yl)carbamoyl)ethene-1-sulfonamide

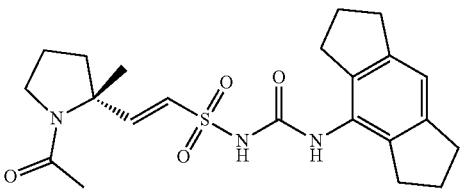 [SMILES: CC(=O)N1CCC[C@]1(C)/C=C/S(=O)(=O)NC(=O)Nc1c2c(cc3c1CCC3)CCC2]

¹H NMR (400 MHz, DMSO-d₆): δ=10.40 (s, 1H), 8.06 (s, 1H), 6.96 (s, 1H), 6.91 (d, J=15.6 Hz, 1H), 6.58 (d, J=15.2 Hz, 1H), 3.57-3.50 (m, 2H), 2.81 (t, J=7.2 Hz, 4H), 2.68 (t, J=7.2 Hz, 4H), 2.01-1.88 (m, 8H), 1.82-1.74 (m, 3H), 1.52 (s, 3H); MS (ESI): m/z (%)=432.09 (100%) (M+H)⁺.

Example-54

(R,E)-1,1-diethyl-2-(2-(N-((1,2,3,5,6,7-hexahydro-s-indacen-4-yl)carbamoyl)sulfamoyl)-vinyl)-2-methylpyrrolidin-1-ium bromide

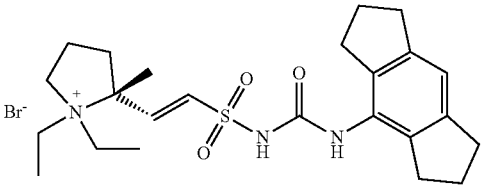

¹H NMR (400 MHz, DMSO-d₆): δ=6.88 (s, 1H), 6.65 (d, J=15.6 Hz, 1H), 6.21-6.15 (m, 1H), 2.84-2.75 (m, 6H), 2.68-2.58 (m, 3H), 2.35-2.29 (m, 2H), 1.96-1.91 (m, 7H), 1.76-1.59 (m, 4H), 0.97 (t, J=7.2 Hz, 6H), 0.88 (s, 3H); MS (ESI): m/z (%)=446.19 (100%) (M+H)⁺.

Example-55

(R,E)-N-((1,2,3,5,6,7-hexahydro-s-indacen-4-yl)carbamoyl)-2-(2-methyl-1-(methylsulfonyl)-pyrrolidin-2-yl)ethene-1-sulfonamide

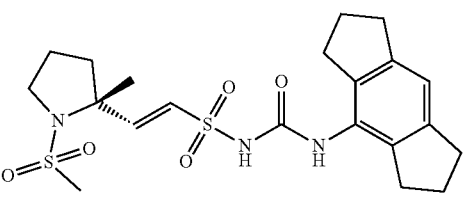

¹H NMR (400 MHz, DMSO-d₆): δ=10.43 (bs, 1H), 8.09 (s, 1H), 6.96 (s, 1H), 6.90 (d, J=15.2 Hz, 1H), 6.72 (d, J=15.2 Hz, 1H), 3.44 (t, J=6.0 Hz, 2H), 2.95 (s, 3H), 2.81 (t, J=7.2 Hz, 4H), 2.68 (t, J=7.2 Hz, 4H), 2.07-1.83 (m, 7H), 1.79-1.74 (m, 1H), 1.24 (s, 3H), MS (ESI): m/z (%)=468.11 (100%) (M+H)⁺.

Example-56

(R,E)-2-(1,2-dimethylpyrrolidin-2-yl)-N-((1,2,3,5,6,7-hexahydro-s-indacen-4-yl)carbamoyl)ethene-1-sulfonamide

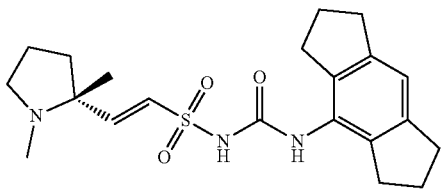 [SMILES: CN1CCC[C@]1(C)/C=C/S(=O)(=O)NC(=O)Nc1c2c(cc3c1CCC3)CCC2]

$^1$H NMR (400 MHz, DMSO-d$_6$): δ=8.04 (s, 1H), 6.93 (s, 1H), 6.74 (d, J=15.6 Hz, 1H), 6.65 (d, J=15.2 Hz, 1H), 2.93-2.86 (m, 1H), 2.80 (t, J=7.2 Hz, 4H), 2.67 (t, J=7.2 Hz, 4H), 2.19 (s, 3H), 1.99-1.91 (m, 5H), 1.80-1.69 (m, 4H), 1.13 (s, 3H), MS (ESI): m/z (%)=404.16 (100%) (M+H)$^+$.

Alternatively, Example 56 was also be prepared as per the procedure described for synthesis of Intermediate-7b (Example 111) using Intermediate 9 and (R)-1,2-dimethylpyrrolidine-2-carbaldehyde, together with conventional techniques known to those skilled in the art of organic synthesis.

Example-57

(R,E)-2-(1-ethyl-2-methylpyrrolidin-2-yl)-N-((1,2,3,5,6,7-hexahydro-s-indacen-4-yl)carbamoyl)ethene-1-sulfonamide

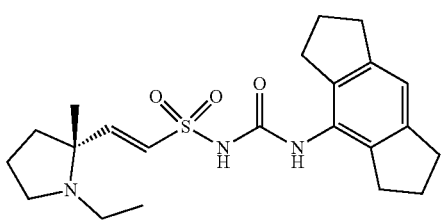 [SMILES: CCN1CCC[C@]1(C)/C=C/S(=O)(=O)NC(=O)Nc1c2c(cc3c1CCC3)CCC2]

$^1$H NMR (400 MHz, DMSO-d$_6$): δ=8.82 (bs, 1H), 6.96 (s, 1H), 6.92 (d, J=9.6 Hz, 1H), 6.41 (m, 1H), 3.60-3.51 (m, 2H), 3.22-3.17 (m, 2H), 2.80-2.73 (m, 5H), 2.61 (t, J=7.2 Hz, 4H), 1.97-1.93 (m, 6H), 1.84-1.80 (m, 1H), 1.53 (s, 3H), 0.90 (t, J=6.4 Hz, 3H); MS (ESI): m/z (%)=418.18 (100%) (M+H)$^+$;

Example-58

(R,E)-2-(1-(cyclopropylmethyl)-2-methylpyrrolidin-2-yl)-N-((1,2,3,5,6,7-hexahydro-s-indacen-4-yl)carbamoyl)ethene-1-sulfonamide

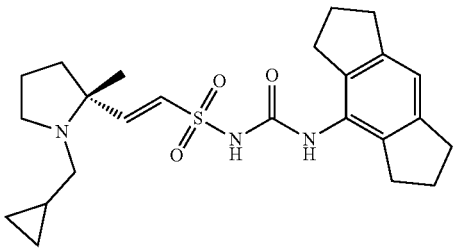 [SMILES: C[C@]1(/C=C/S(=O)(=O)NC(=O)Nc2c3c(cc4c2CCC4)CCC3)CCCN1CC1CC1]

$^1$H NMR (400 MHz, DMSO-d$_6$): δ=10.39 (s, 1H), 8.06 (s, 1H), 6.94 (s, 1H), 6.75 (d, J=15.6 Hz, 1H), 6.69 (d, J=15.6 Hz, 1H), 3.18-3.13 (m, 1H), 2.80 (t, J=7.2 Hz, 5H), 2.67 (t, J=7.2 Hz, 4H), 2.33-2.11 (m, 2H), 1.94 (t, J=7.2 Hz, 4H), 1.80-1.71 (m, 4H), 1.12 (s, 3H), 0.86-0.79 (m, 1H), 0.42 (quin, J=8.8 Hz, 2H), 0.05-0.04 (m, 2H); MS (ESI): m/z (%)=444.17 (100%) (M+H)$^+$.

Example-59

(S,E)-N-((1,2,3,5,6,7-hexahydro-s-indacen-4-yl)carbamoyl)-2-(pyrrolidin-2-yl)ethene-sulfonamide

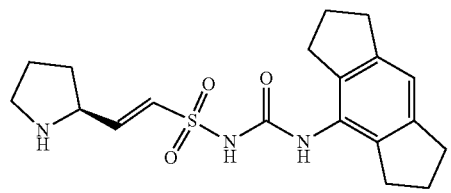 [SMILES: O=C(Nc1c2c(cc3c1CCC3)CCC2)NS(=O)(=O)/C=C/[C@@H]1CCCN1]

$^1$H NMR (400 MHz, DMSO): δ=8.75 (bs, 1H), 7.50 (s, 1H), 6.95 (d, J=15.6 Hz, 1H), 6.80 (s, 1H), 6.39-6.33 (m, 1H), 4.08-4.02 (m, 1H), 3.16-4.11 (m, 2H), 2.77 (t, J=7.2 Hz, 4H), 2.71 (t, J=7.2 Hz, 4H), 2.12-2.08 (m, 1H), 1.96-1.85 (m, 6H), 1.68-1.62 (m, 1H); MS (ESI): m/z (%)=376.16 (100%) (M+H)$^+$.

Example-60

(S,E)-N-((1,2,3,5,6,7-hexahydro-s-indacen-4-yl)carbamoyl)-2-(1-methylpyrrolidin-2-yl)ethenesulfonamide

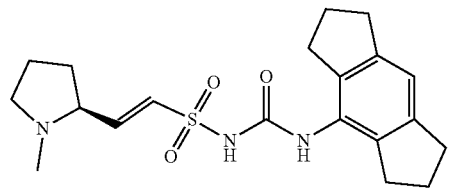 [SMILES: CN1CCC[C@H]1/C=C/S(=O)(=O)NC(=O)Nc1c2c(cc3c1CCC3)CCC2]

¹H NMR (400 MHz, DMSO): δ=8.00 (s, 1H), 6.93 (s, 1H), 6.85 (d, J=15.2 Hz, 1H), 6.58-6.52 (m, 1H), 3.12-3.04 (m, 2H), 2.80 (t, J=7.2 Hz, 4H), 2.67 (t, J=7.2 Hz, 4H), 2.36-2.31 (m, 1H), 2.27 (s, 3H), 2.08-1.91 (m, 5H), 1.80-1.72 (m, 2H), 1.70-1.50 (m, 1H); MS (ESI): m/z (%)=390.17 (100%) (M+H)⁺.

Example-61

(S,E)-tert-butyl2-(2-(N-((1,2,3,5,6,7-hexahydro-s-indacen-4-yl)carbamoyl)sulfamoyl)vinyl)pyrrolidine-1-carboxylate

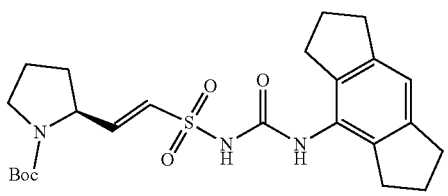 [SMILES: CC(C)(C)OC(=O)N1CCC[C@H]1/C=C/S(=O)(=O)NC(=O)Nc1c2c(cc3c1CCC3)CCC2]

¹H NMR (400 MHz, DMSO): δ=10.42 (bs, 1H), 8.09 (s, 1H), 6.96 (s, 1H), 6.71-6.67 (m, 1H), 6.61-6.57 (m, 1H), 4.45-4.38 (m, 1H), 3.29-3.25 (m, 2H), 2.81 (t, J=7.2 Hz, 4H), 2.67 (t, J=7.2 Hz, 4H), 2.09-1.93 (m, 5H), 1.78-1.71 (m, 3H), 1.33 (s, 9H); MS (ESI): m/z (%)=498.18 (80%) (M+Na)⁺.

Example-62

(S,E)-2-(1-(cyclopropylmethyl)pyrrolidin-2-yl)-N-((1,2,3,5,6,7-hexahydro-s-indacen-4-yl)carbamoyl)ethenesulfonamide

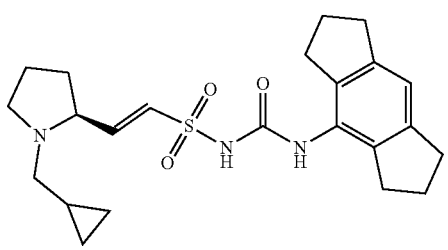 [SMILES: O=C(Nc1c2c(cc3c1CCC3)CCC2)NS(=O)(=O)/C=C/[C@@H]1CCCN1CC1CC1]

¹H NMR (400 MHz, DMSO-d₆): δ=10.32 (bs, 1H), 8.02 (bs, 1H), 6.93 (s, 1H), 6.86 (d, J=14.8 Hz, 1H), 6.64-6.50 (m, 1H), 3.50-3.20 (m, 3H), 2.80 (t, J=7.2 Hz, 4H), 2.67 (t, J=7.2 Hz, 4H), 2.61-2.56 (m, 1H), 2.15-1.91 (m, 6H), 1.85-1.78 (m, 2H), 1.62-1.53 (m, 1H), 0.86-0.80 (m, 1H), 0.50-0.30 (m, 2H), 0.15-0.14 (m, 2H); MS (ESI): m/z (%)=430.19 (100%) (M+H)⁺.

Example-63

(S,E)-N-((1,2,3,5,6,7-hexahydro-s-indacen-4-yl)carbamoyl)-2-(1-(pyridin-3-ylsulfonyl)-pyrrolidin-2-yl)ethenesulfonamide

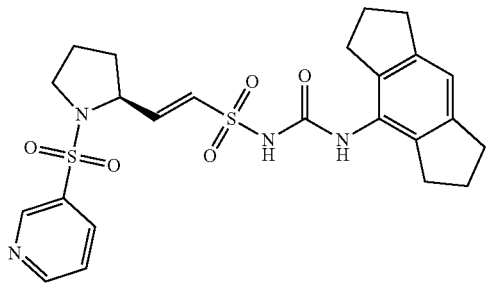 [SMILES: O=C(Nc1c2c(cc3c1CCC3)CCC2)NS(=O)(=O)/C=C/[C@@H]1CCCN1S(=O)(=O)c1cccnc1]

¹H NMR (400 MHz, DMSO-d₆): δ=10.40 (bs, 1H), 9.02 (d, J=2.0 Hz, 1H), 8.90-8.88 (m, 1H), 8.29-8.26 (m, 1H), 8.04 (s, 1H), 7.68-7.65 (m, 1H), 6.94-6.87 (m, 2H), 6.72-6.67 (m, 1H), 4.52-4.49 (m, 1H), 3.44-3.42 (m, 1H), 3.21-3.15 (m, 1H), 2.80 (t, J=7.2 Hz, 4H), 2.69 (t, J=7.2 Hz, 4H), 1.99-1.91 (m, 4H), 1.76-1.65 (m, 4H); MS (ESI): m/z (%)=517.11 (100%) (M+H)⁺.

Example-64

(S,E)-N-((2,6-diisopropylphenyl)carbamoyl)-2-(pyrrolidin-2-yl)ethenesulfonamide

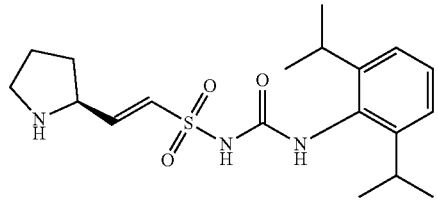 [SMILES: CC(C)c1cccc(C(C)C)c1NC(=O)NS(=O)(=O)/C=C/[C@@H]1CCCN1]

¹H NMR (400 MHz, DMSO): δ=9.50 (bs, 1H), 7.48 (bs, 1H), 7.17-7.05 (m, 3H), 6.99-6.88 (m, 1H), 6.43 (bs, 1H), 4.15-3.90 (m, 1H), 3.20-3.00 (m, 4H), 2.15-2.00 (m, 1H), 1.99-1.80 (m, 3H), 1.79-1.60 (m, 1H), 1.20-1.00 (m, 12H); MS (ESI): m/z (%)=380.16 (100%) (M+H)⁺.

Example-65

(S,E)-N-((2,6-diisopropylphenyl)carbamoyl)-2-(1-ethylpyrrolidin-2-yl)ethenesulfonamide

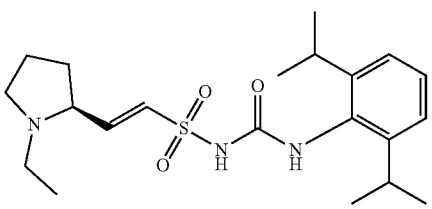 [SMILES: CCN1CCC[C@H]1/C=C/S(=O)(=O)NC(=O)Nc1c(C(C)C)cccc1C(C)C]

¹H NMR (400 MHz, DMSO-d₆): δ=10.60 (bs, 1H), 7.86 (s, 1H), 7.27-7.23 (m, 1H), 7.15-7.13 (m, 2H), 6.84 (d, J=15.2 Hz, 1H), 6.66-6.61 (m, 1H), 3.32-3.02 (m, 4H), 2.75-2.60 (m, 1H), 2.41-2.25 (m, 2H), 2.05-1.96 (m, 1H), 1.90-1.70 (m, 2H), 1.65-1.45 (m, 1H), 1.12-1.11 (m, 12H), 1.01 (t, J=7.2 Hz, 3H); MS (ESI): m/z (%)=408.19 (100%) (M+H)⁺.

Example-66

(S,E)-N-((2,6-diisopropylphenyl)carbamoyl)-2-(1-(methylsulfonyl)pyrrolidin-2-yl)ethene-sulfonamide

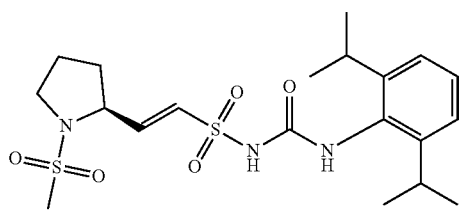 [SMILES: CC(C)c1cccc(C(C)C)c1NC(=O)NS(=O)(=O)/C=C/[C@@H]1CCCN1S(C)(=O)=O]

¹H NMR (400 MHz, DMSO-d₆): δ=7.81 (s, 1H), 7.25-7.21 (m, 1H), 7.13-7.11 (m, 2H), 6.75-6.64 (m, 2H), 4.46 (s, 1H), 3.29-3.24 (m, 1H), 3.10-3.03 (m, 2H), 2.93 (s, 3H), 2.09-2.04 (m, 1H), 1.89-1.83 (m, 1H), 1.77-1.73 (m, 3H), 1.12-1.11 (m, 12H); MS (ESI): m/z (%)=458.15 (100%) (M+H)⁺.

Example-67

(S,E)-N-((2,6-diisopropylphenyl)carbamoyl)-2-(1-methylpyrrolidin-2-yl)ethenesulfonamide

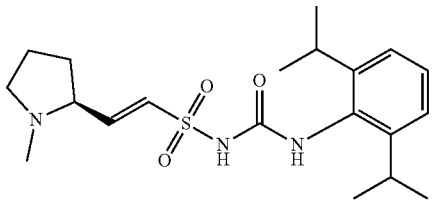 [SMILES: CC(C)c1cccc(C(C)C)c1NC(=O)NS(=O)(=O)/C=C/[C@@H]1CCCN1C]

¹H NMR (400 MHz, DMSO-d₆): δ=7.69 (s, 1H), 7.22-7.18 (m, 1H), 7.11-7.09 (m, 2H), 6.75 (d, J=15.2 Hz, 1H), 6.55-6.30 (m, 1H), 3.12-2.99 (m, 3H), 2.79-2.76 (m, 1H), 2.23-2.18 (m, 4H), 2.00-1.95 (m, 1H), 1.76-1.68 (m, 2H), 1.54-1.49 (m, 1H), 1.11-1.09 (m, 12H); MS (ESI): m/z (%)=394.19 (100%) (M+H)⁺.

Example-68

(S,E)-2-(1-acetylpyrrolidin-2-yl)-N-((2,6-diisopropylphenyl)carbamoyl)ethenesulfonamide

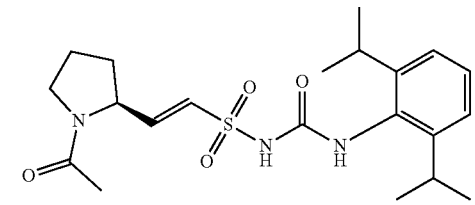 [SMILES: CC(=O)N1CCC[C@H]1/C=C/S(=O)(=O)NC(=O)Nc1c(C(C)C)cccc1C(C)C]

¹H NMR (400 MHz, DMSO-d₆): δ=10.55 (bs, 1H), 7.89-7.86 (m, 1H), 7.28-7.23 (m, 1H), 7.15-7.13 (m, 2H), 6.76-6.69 (m, 1H), 6.63-6.53 (m, 1H), 4.68-4.61 (m, 1H), 3.52-3.39 (m, 1H), 3.08-3.02 (m, 2H), 1.97 (s, 3H), 1.93-1.70 (m, 5H), 1.13-1.11 (m, 12H); MS (ESI): m/z (%)=422.18 (100%) (M+H)⁺.

Example-69

(S,E)-2-(1-acetylpyrrolidin-2-yl)-N-((1,2,3,5,6,7-hexahydro-s-indacen-4-yl)carbamoyl)-ethenesulfonamide

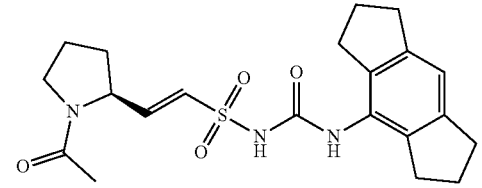 [SMILES: CC(=O)N1CCC[C@H]1/C=C/S(=O)(=O)NC(=O)Nc1c2c(cc3c1CCC3)CCC2]

¹H NMR (400 MHz, DMSO-d₆): δ=10.30 (bs, 1H), 8.11-8.05 (m, 1H), 6.95 (s, 1H), 6.78-6.56 (m, 2H), 4.72-4.62 (m, 1H), 3.57-3.35 (m, 2H), 2.81 (t, J=7.2 Hz, 4H), 2.67 (q, J=7.2 Hz, 4H), 1.99-1.95 (m, 6H), 1.85 (s, 3H), 1.84-1.71 (m, 2H); MS (ESI): m/z (%)=418.16 (100%) (M+H)⁺.

Example-70

(S,E)-N-((1,2,3,5,6,7-hexahydro-s-indacen-4-yl)carbamoyl)-2-(1-(tetrahydro-2H-pyran-4-carbonyl)pyrrolidin-2-yl)ethenesulfonamide

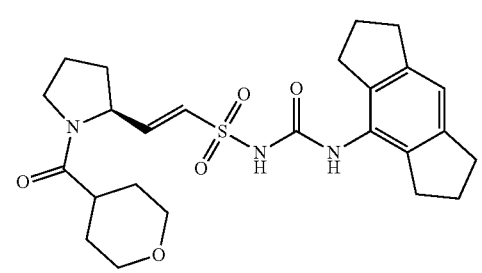 [SMILES: O=C(Nc1c2c(cc3c1CCC3)CCC2)NS(=O)(=O)/C=C/[C@@H]1CCCN1C(=O)C1CCOCC1]

¹H NMR (400 MHz, DMSO-d₆): δ=10.40 (bs, 1H), 8.03 (s, 1H), 6.94-6.93 (m, 1H), 6.74-6.49 (m, 2H), 6.64-6.50 (m,

1H), 4.84-4.65 (m, 1H), 3.87-3.78 (m, 2H), 3.64-3.52 (m, 1H), 3.50-3.25 (m, 2H), 2.81 (t, J=7.6 Hz, 4H), 2.73-2.67 (m, 5H), 2.01-1.89 (m, 5H), 1.82-1.72 (m, 3H), 1.61-1.49 (m, 4H); MS (ESI): m/z (%)=488.21 (100%) (M+H)+.

Example-71

(E)-N-((1,2,3,5,6,7-hexahydro-s-indacen-4-yl)carbamoyl)-2-(tetrahydro-2H-pyran-4-yl)ethenesulfonamide

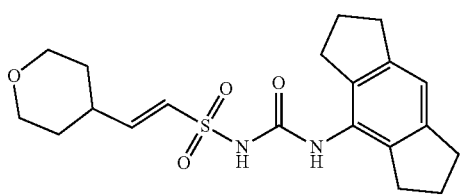 [SMILES: O=C(Nc1c2c(cc3c1CCC3)CCC2)NS(=O)(=O)/C=C/C1CCOCC1]

¹H NMR (400 MHz, DMSO-d₆): δ=10.33 (bs, 1H), 8.07 (s, 1H), 6.96 (s, 1H), 6.80-6.74 (m, 1H), 6.69-6.65 (m, 1H), 3.87-3.83 (m, 2H), 3.37-3.34 (m, 3H), 2.81 (t, J=7.6 Hz, 4H), 2.67 (t, J=7.6 Hz, 4H), 2.08-1.94 (m, 4H), 1.65-1.62 (m, 2H), 1.55-1.30 (m, 2H); MS (ESI): m/z (%)=391.15 (100%) (M+H)+.

Example-72

(S,E)-N-((1,2,3,5,6,7-hexahydro-s-indacen-4-yl)carbamoyl)-2-(1-nicotinoylpyrrolidin-2-yl)ethenesulfonamide

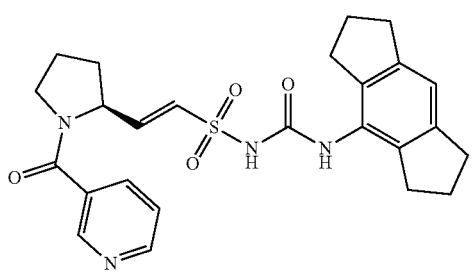 [SMILES: O=C(Nc1c2c(cc3c1CCC3)CCC2)NS(=O)(=O)/C=C/[C@@H]1CCCN1C(=O)c1cccnc1]

¹H NMR (400 MHz, DMSO-d₆): δ=10.35 (bs, 1H), 8.76-8.59 (m, 2H), 8.05 (s, 1H), 6.72 (d, J=8 Hz, 0.72H), 7.77 (d, J=8 Hz, 0.23H), 7.48-7.40 (m, 1H), 6.94 (s, 1H), 6.84 (s, 1H), 6.57-6.55 (m, 1H), 4.86-4.50 (m, 1H), 3.65-3.59 (m, 1H), 3.41-3.37 (m, 1H), 2.78 (t, J=7.6 Hz, 4H), 2.65 (t, J=7.6 Hz, 4H), 2.20-2.13 (m, 1H), 1.96-1.84 (m, 7H); MS (ESI): m/z (%)=481.18 (100%) (M+H)+.

Example-73

(E)-N-((1,2,3,5,6,7-hexahydro-s-indacen-4-yl)carbamoyl)-2-(tetrahydrofuran-2-yl)ethene-1-sulfonamide

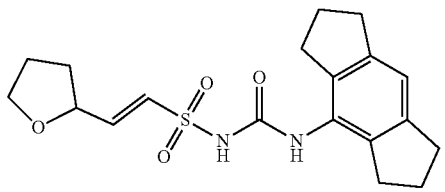 [SMILES: O=C(Nc1c2c(cc3c1CCC3)CCC2)NS(=O)(=O)/C=C/C1CCCO1]

¹H NMR (400 MHz, DMSO-d₆): δ=10.40 (bs, 1H), 8.11 (s, 1H), 6.96 (s, 1H), 6.81 (dd, J=4.0 Hz, J=14.8 Hz, 1H), 6.74 (dd, J=1.2 Hz, J=15.2 Hz, 1H), 4.57-4.53 (m, 1H), 3.86-3.81 (m, 1H), 3.76-3.70 (m, 1H), 2.81 (t, J=7.2 Hz, 4H), 2.67 (t, J=7.2 Hz, 4H), 2.16-2.07 (m, 1H), 2.01-1.94 (m, 4H), 1.90-1.79 (m, 2H), 1.67-1.62 (m, 1H); MS (ESI): m/z (%)=377.15 (100%) (M+H)+.

Example-74

(S,E)-N-((1,2,3,5,6,7-hexahydro-s-indacen-4-yl)carbamoyl)-2-(1-(thiophen-2-ylmethyl)-pyrrolidin-2-yl)ethene-1-sulfonamide

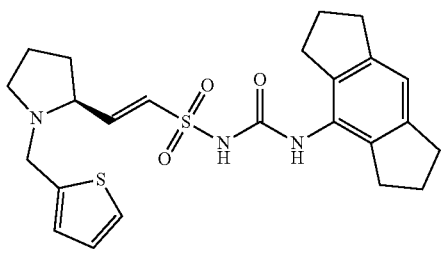 [SMILES: O=C(Nc1c2c(cc3c1CCC3)CCC2)NS(=O)(=O)/C=C/[C@@H]1CCCN1Cc1cccs1]

¹H NMR (400 MHz, DMSO-ds): δ=10.40 (bs, 1H), 8.10 (s, 1H), 7.43-7.39 (m, 1H), 7.01-6.86 (m, 4H), 6.71-6.63 (m, 1H), 3.93 (d, J=14 Hz, 1H), 3.58 (d, J=14 Hz, 1H), 3.28-3.24 (m, 1H), 2.97-2.92 (m, 1H), 2.77 (t, J=7.2 Hz, 4H), 2.63 (t, J=7.2 Hz, 4H), 2.33-2.04 (m, 1H), 2.04-1.88 (m, 5H), 1.75-1.68 (m, 2H), 1.59-1.54 (m, 1H); MS (ESI): m/z (%)=472.12 (100%) (M+H)+.

Example-75 tert-butyl(S,E)-2-(2-(N-((4-fluoro-2,6-diisopropylphenyl)carbamoyl)sulfamoyl)vinyl)-pyrrolidine-1-carboxylate

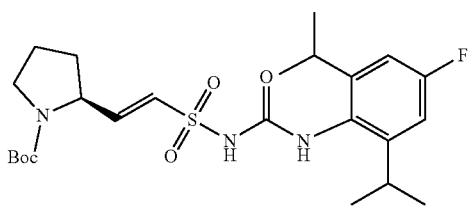 [SMILES: CC(C)c1cc(F)cc(C(C)C)c1NC(=O)NS(=O)(=O)/C=C/[C@@H]1CCCN1C(=O)OC(C)(C)C]

¹H NMR (400 MHz, DMSO): δ=10.06 (bs, 1H), 7.93 (s, 1H), 6.97-6.95 (m, 2H), 6.72-6.55 (m, 2H), 4.46-4.02 (m, 1H), 3.30-3.26 (m, 2H), 3.02-2.99 (m, 2H), 2.22-1.99 (m, 1H), 1.78-1.68 (m, 3H), 1.45 (s, 9H), 1.11 (d, J=6.8 Hz, 12H); MS (ESI): m/z (%)=398.29 (100%) (M–100)⁺; 520.36 (15%) (M+Na)⁺; 496.32 (100%) (M–H)⁺.

Example-76

(S,E)-N-((4-fluoro-2,6-diisopropylphenyl)carbamoyl)-2-(pyrrolidin-2-yl)ethene-1-sulfonamide

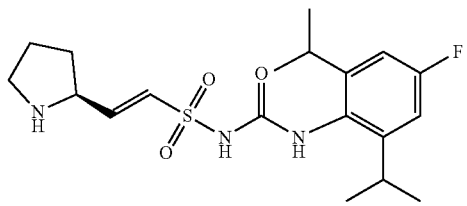 [SMILES: CC(C)c1cc(F)cc(C(C)C)c1NC(=O)NS(=O)(=O)/C=C/[C@@H]1CCCN1]

¹H NMR (400 MHz, DMSO): δ=9.40 (bs, 1H), 7.39 (bs, 1H), 7.02-6.76 (m, 3H), 6.39-6.22 (m, 1H), 4.05-4.04 (m, 1H), 3.17-3.13 (m, 4H), 2.06-1.56 (m, 5H), 1.10-1.09 (m, 12H); MS (ESI): m/z (%)=398.26 (100%) (M–H)⁺.

Example-77

(S,E)-N-((4-fluoro-2,6-diisopropylphenyl)carbamoyl)-2-(1-methylpyrrolidin-2-yl)ethene-1-sulfonamide

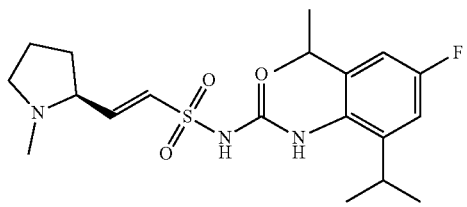 [SMILES: CC(C)c1cc(F)cc(C(C)C)c1NC(=O)NS(=O)(=O)/C=C/[C@@H]1CCCN1C]

¹H NMR (400 MHz, DMSO-d₆): δ=10.90 (bs, 1H), 7.84 (bs, 1H), 6.94 (d, J=9.6 Hz, 2H), 6.90 (d, J=15.2 Hz, 1H), 6.58-6.53 (m, 1H), 3.08-2.95 (m, 4H), 2.33-2.27 (m, 1H), 2.23 (s, 3H), 2.07-1.97 (m, 1H), 1.78-1.73 (m, 2H), 1.59-1.50 (m, 1H), 6.75 (d, J=6.8 Hz, 12H); MS (ESI): m/z (%)=412.26 (100%) (M+H)⁺.

Example-78

(R,E)-N-((1,2,3,5,6,7-hexahydro-s-indacen-4-yl)carbamoyl)-2-(1-isobutyl-2-methyl-pyrrolidin-2-yl)ethene-1-sulfonamide

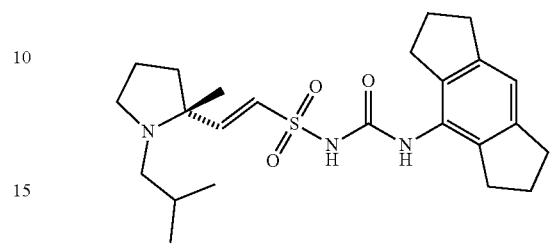

¹H NMR (400 MHz, DMSO-d₆): δ=8.03 (bs, 1H), 6.89 (s, 1H), 6.88 (d, J=15.6 Hz, 1H), 6.54 (d, J=15.6 Hz, 1H), 2.81-2.77 (m, 6H), 2.70-2.57 (m, 5H), 2.13-2.00 (m, 2H), 1.98-1.91 (m, 4H), 1.75-1.53 (m, 5H), 1.06 (s, 3H), 0.90-0.79 (m, 6H); MS (ESI): m/z (%)=446.26 (100%) (M+H)⁺.

Example-79

(R,E)-N-((1,2,3,5,6,7-hexahydro-s-indacen-4-yl)carbamoyl)-2-(2-methyl-1-propylpyrrolidin-2-yl)ethene-1-sulfonamide

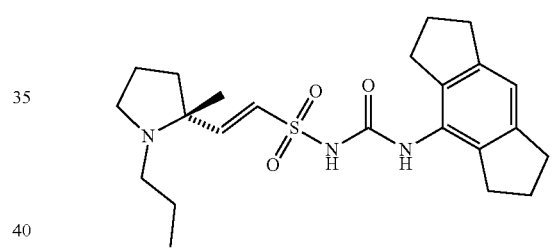

¹H NMR (400 MHz, DMSO-d₆): δ=7.99 (bs, 1H), 6.90 (s, 1H), 6.67 (d, J=15.6 Hz, 1H), 6.57 (d, J=16.0 Hz, 1H), 2.93-2.87 (m, 1H), 2.79 (t, J=7.2 Hz, 4H), 2.70-2.66 (m, 5H), 2.33-2.29 (m, 2H), 1.99-1.91 (m, 4H), 1.85-1.66 (m, 4H), 1.45-1.33 (m, 2H), 1.09 (s, 3H), 0.80 (t, J=7.6 Hz, 3H); MS (ESI): m/z (%)=432.25 (100%) (M+H)⁺.

Example-80

(S,E)-N-((1,2,3,5,6,7-hexahydro-s-indacen-4-yl)carbamoyl)-2-(1-(thiazol-2-yl)pyrrolidin-2-yl)ethene-1-sulfonamide

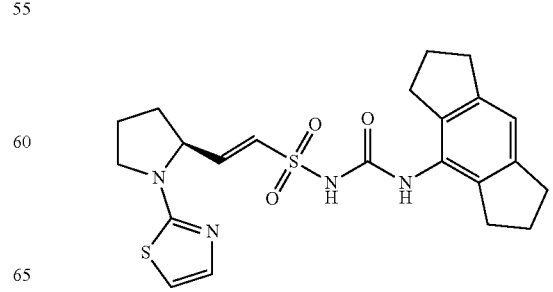

¹H NMR (400 MHz, DMSO-d₆): δ=10.4 (bs, 1H), 8.09 (s, 1H), 7.14 (d, J=3.6 Hz, 1H), 6.96 (s, 1H), 6.84-6.79 (m, 1H), 6.75 (d, J=3.6 Hz, 1H), 6.72-6.66 (m, 1H), 4.59-4.58 (m, 1H), 3.58-3.53 (m, 1H), 3.41-3.34 (m, 1H), 2.81 (t, J=7.2 Hz, 4H), 2.64 (t, J=7.2 Hz, 4H), 2.30-2.18 (m, 1H), 2.04-1.87 (m, 7H); MS (ESI): m/z (%)=459.17 (100%) (M+H)⁺.

Example-81

(E)-N-((1,2,3,5,6,7-hexahydro-s-indacen-4-yl)carbamoyl)-2-(piperidin-3-yl)ethene-sulfonamide

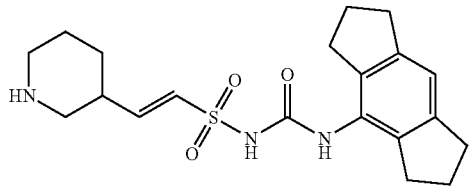 [SMILES: O=C(Nc1c2c(cc3c1CCC3)CCC2)NS(=O)(=O)/C=C/C1CCCNC1]

¹H NMR (400 MHz, DMSO-d₆): δ=10.04 (brs, 1H), 7.57 (s, 1H), 6.81 (s, 1H), 6.67 (d, J=15.2 Hz, 1H), 6.24 (dd, J=15.2 Hz, J=6.0 Hz, 1H), 3.23-3.12 (m, 2H), 2.77 (t, J=7.2 Hz, 4H), 2.70 (t, J=7.2 Hz, 4H), 2.51-2.49 (m, 2H), 1.97-1.89 (m, 5H), 1.79-1.76 (m, 2H), 1.63-1.59 (m, 1H), 1.37-1.29 (m, 1H); MS (ESI): m/z (%)=390.15 (100%) (M+H)⁺.

Example-82

(E)-2-(1-ethylpiperidin-3-yl)-N-((1,2,3,5,6,7-hexahydro-s-indacen-4-yl)carbamoyl)ethene-sulfonamide

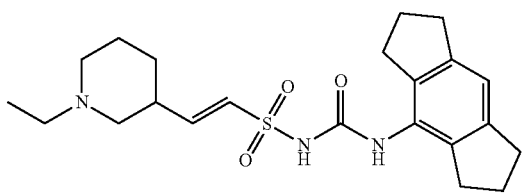 [SMILES: CCN1CCCC(/C=C/S(=O)(=O)NC(=O)Nc2c3c(cc4c2CCC4)CCC3)C1]

¹H NMR (400 MHz, DMSO-d₆): δ=7.82 (s, 1H), 6.94 (s, 1H), 6.70 (d, J=15.2 Hz, 1H), 6.53 (dd, J=15.2 Hz, J=6.0 Hz, 1H), 2.98-2.89 (m, 2H), 2.79 (t, J=7.2 Hz, 4H), 2.68 (t, J=7.2 Hz, 4H), 2.57-2.54 (m, 2H), 2.21-2.09 (m, 2H), 1.99-1.91 (m, 4H), 1.72-1.69 (m, 2H), 1.58-1.50 (m, 1H), 1.24-1.32 (m, 2H), 1.05 (t, J=7.2 Hz, 3H); MS (ESI): m/z (%)=418.18 (100%) (M+H)⁺.

Example-83

(E)-tert-butyl3-(2-(N-((1,2,3,5,6,7-hexahydro-s-indacen-4-yl)carbamoyl)sulfamoyl)vinyl)-piperidine-1-carboxylate

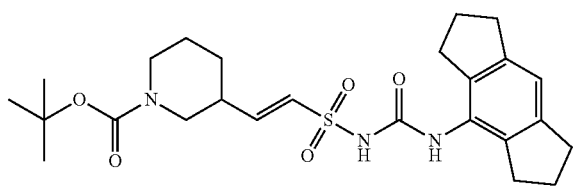 [SMILES: CC(C)(C)OC(=O)N1CCCC(/C=C/S(=O)(=O)NC(=O)Nc2c3c(cc4c2CCC4)CCC3)C1]

¹H NMR (400 MHz, DMSO-d₆): δ=10.4 (brs, 1H), 7.93 (s, 1H), 6.93 (s, 1H), 6.74 (d, J=15.2 Hz, 1H), 6.61 (dd, J=15.2 Hz, J=6.8 Hz, 1H), 3.75-3.64 (m, 2H), 2.93-2.88 (m, 2H), 2.80 (t, J=7.2 Hz, 4H), 2.68 (t, J=7.2 Hz, 4H), 2.38-2.33 (m, 1H), 2.00-1.93 (m, 4H), 1.80-1.70 (m, 1H), 1.59-1.55 (m, 1H), 1.39 (s, 9H), 1.36-1.34 (m, 1H), 0.91-0.81 (m, 1H); MS (ESI): m/z (%)=390.16 (100%) [(M−100)+H]⁺, 488.17 (100%) (M−1).

Example-84

(E)-N-((1,2,3,5,6,7-hexahydro-s-indacen-4-yl)carbamoyl)-2-(1-(methylsulfonyl)piperidin-3-yl)ethene-sulfonamide

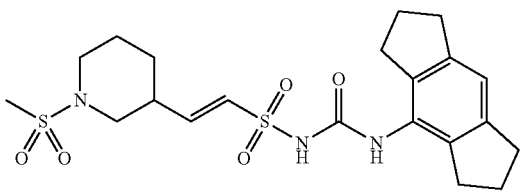 [SMILES: CS(=O)(=O)N1CCCC(/C=C/S(=O)(=O)NC(=O)Nc2c3c(cc4c2CCC4)CCC3)C1]

¹H NMR (400 MHz, DMSO-d₆): δ=10.4 (brs, 1H), 7.98 (s, 1H), 6.93 (s, 1H), 6.79 (d, J=15.2 Hz, 1H), 6.66 (dd, J=15.2 Hz, J=6.4 Hz, 1H), 3.47-3.39 (m, 2H), 2.87 (s, 3H), 2.80 (t, J=7.6 Hz, 4H), 2.68 (t, J=7.6 Hz, 4H), 2.60-2.46 (m, 3H), 2.00-1.91 (m, 4H), 1.80-1.72 (m, 2H), 1.57-1.49 (m, 1H), 1.35-1.24 (m, 1H); MS (ESI): m/z (%)=468.14 (100%) (M+H)⁺, 490.40 (50%) (M+Na), 466.11 (100%) (M−1).

Example-85

(E)-2-(1-acetylpiperidin-3-yl)-N-((1,2,3,5,6,7-hexahydro-s-indacen-4-yl)carbamoyl)ethene-sulfonamide

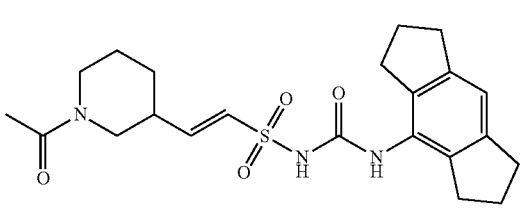 [SMILES: CC(=O)N1CCCC(/C=C/S(=O)(=O)NC(=O)Nc2c3c(cc4c2CCC4)CCC3)C1]

¹H NMR (400 MHz, DMSO-d₆): δ=8.00 (s, 1H), 6.94 (s, 1H), 6.80-6.65 (m, 2H), 4.16-4.10 (m, 1H), 3.77-3.63 (m, 1H), 3.09-2.93 (m, 1H), 2.80 (t, J=7.2 Hz, 4H), 2.75-2.64 (m, 5H), 2.39-2.26 (m, 1H), 2.00-1.91 (m, 7H), 1.90-1.77 (m, 1H), 1.74-1.57 (m, 1H), 1.54-1.28 (m, 2H); MS (ESI): m/z (%)=468.14 (100%) (M+H)⁺, 490.40 (50%) (M+Na), 466.11 (100%) (M−1).

Example-86 tert-butyl(E)-2-(2-(N-((1,2,3,5,6,7-hexahydro-s-indacen-4-yl)carbamoyl)sulfamoyl)vinyl)-azetidine-1-carboxylate

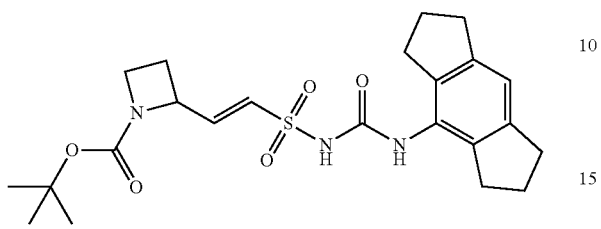

Example 86 was prepared as per the procedure described for synthesis of Intermediate-3a using Intermediate-11.

$^1$H NMR (400 MHz, DMSO-d$_6$): δ=10.57 (brs, 1H), 7.83 (s, 1H), 6.89 (s, 1H), 6.73 (d, J=15.2 Hz, 1H), 6.66 (dd, J=15.2 Hz, J=4.4 Hz, 1H), 4.73-4.84 (m, 1H), 3.80-3.70 (m, 2H), 2.79 (t, J=7.2 Hz, 4H), 2.69 (t, J=7.2 Hz, 4H), 2.46-2.33 (m, 1H), 2.04-1.97 (m, 5H), 1.35 (s, 9H); MS (ESI): m/z (%)=484.84 (90%) (M+H)$^+$, 460.23 (100%) (M−1).

Example-87

(E)-N-((1,2,3,5,6,7-hexahydro-s-indacen-4-yl)carbamoyl)-2-(1-methylazetidin-2-yl)ethene-1-sulfonamide

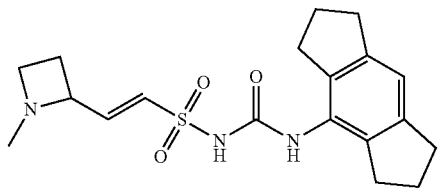 [SMILES: CN1CCC1/C=C/S(=O)(=O)NC(=O)Nc1c2c(cc3c1CCC3)CCC2]

$^1$H NMR (400 MHz, DMSO-d$_6$): δ=10.45 (brs, 1H), 7.98 (s, 1H), 6.92 (s, 1H), 6.84 (d, J=14.8 Hz, 1H), 6.72 (dd, J=15.2 Hz, J=5.2 Hz 1H), 3.95-3.82 (m, 1H), 3.44-3.36 (m, 2H), 3.09-2.95 (m, 1H), 2.80 (t, J=7.2 Hz, 4H), 2.68 (t, J=6.8 Hz, 4H), 2.30 (s, 3H), 2.26-2.20 (m, 1H), 2.03-1.89 (m, 4H); MS (ESI): m/z (%)=376.19 (100%) (M+H)$^+$, 374.16 (100%) (M−1).

Example-88

(E)-2-(azetidin-2-yl)-N-((1,2,3,5,6,7-hexahydro-s-indacen-4-yl)carbamoyl)ethene-1-sulfonamide

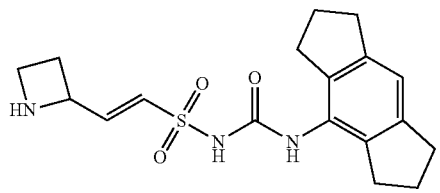 [SMILES: O=C(Nc1c2c(cc3c1CCC3)CCC2)NS(=O)(=O)/C=C/C1CCN1]

$^1$H NMR (400 MHz, DMSO-d$_6$): δ=7.51 (s, 1H), 6.94 (d, J=15.2 Hz, 1H), 6.80 (s, 1H), 6.55 (dd, J=15.2 Hz, J=7.2 Hz, 1H), 5.01-4.95 (m, 1H), 3.89-3.82 (m, 1H), 3.72-3.62 (m, 1H), 2.77 (t, J=7.2 Hz, 4H), 2.70 (t, J=6.8 Hz, 4H), 2.50-2.33 (m, 1H), 1.96-1.88 (m, 5H); MS (ESI): m/z (%)=362.24 (100%) (M+H)$^+$.

Example-89

(R,E)-N-((1,2,3,5,6,7-hexahydro-s-indacen-4-yl)carbamoyl)-2-(1-(tetrahydro-2H-pyran-4-yl)pyrrolidin-2-yl)ethene-1-sulfonamide

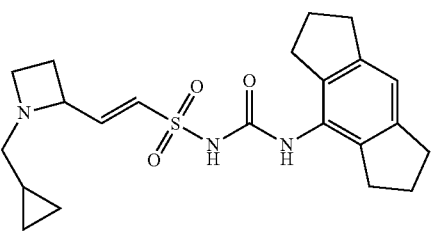 [SMILES: O=C(Nc1c2c(cc3c1CCC3)CCC2)NS(=O)(=O)/C=C/C1CCN1CC1CC1]

$^1$H NMR (400 MHz, DMSO-d$_6$): δ=10.36 (brs, 1H), 7.99 (s, 1H), 6.94-6.90 (m, 2H), 6.77 (dd, J=14.8 Hz, J=5.2 Hz, 1H), 3.99-3.86 (m, 1H), 3.46-3.39 (m, 2H), 3.13-2.96 (m, 1H), 2.80 (t, J=7.2 Hz, 4H), 2.66 (t, J=7.2 Hz, 4H), 2.51-2.33 (m, 1H), 2.30-2.16 (m, 1H), 1.99-1.92 (m, 5H), 0.82-0.61 (m, 1H), 0.50-0.30 (m, 2H), 0.22-0.08 (m, 2H); MS (ESI): m/z (%)=416.29 (100%) (M+H)$^+$.

Example-90

(S,E)-2-(1-((5-chlorothiophen-2-yl)sulfonyl)pyrrolidin-2-yl)-N-((1,2,3,5,6,7-hexahydro-s-indacen-4-yl)carbamoyl)ethenesulfonamide

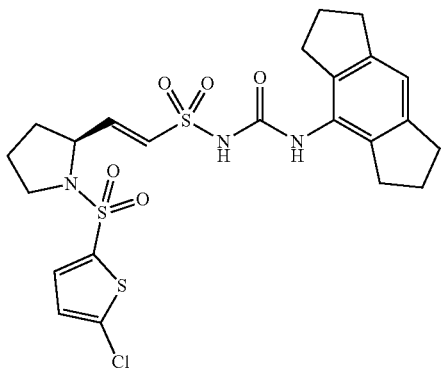 [SMILES: O=C(Nc1c2c(cc3c1CCC3)CCC2)NS(=O)(=O)/C=C/[C@@H]1CCCN1S(=O)(=O)c1ccc(Cl)s1]

$^1$H NMR (400 MHz, DMSO-d$_6$): δ=8.01 (s, 1H), 7.68 (t, J=1.2 Hz, 1H), 7.36 (d, J=4.0 Hz, 1H), 6.90 (s, 1H), 6.85 (s, 1H), 6.82 (s, 1H), 4.40 (d, J=5.2 Hz, 1H), 3.43 (t, J=6.8 Hz, 1H), 3.32 (s, 1H), 3.20 (d, J=7.6 Hz, 1H), 2.80 (t, J=7.2 Hz, 4H), 2.69 (t, J=8.8 Hz, 4H), 1.95 (m, 4H), 1.74 (m, 3H), 1.64 (s, 1H); MS (ESI): m/z (%)=556 (100%) (M+1).

Example-91

(S,E)-2-(1-(benzylsulfonyl)pyrrolidin-2-yl)-N-((1,2,3,5,6,7-hexahydro-s-indacen-4-yl)carbamoyl)ethenesulfonamide

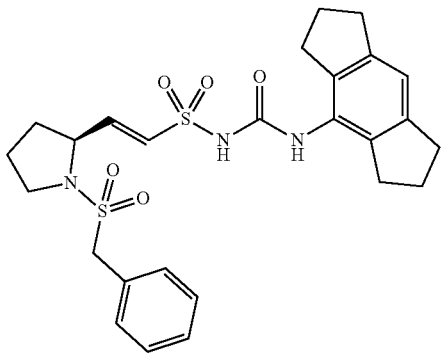 [SMILES: O=C(Nc1c2c(cc3c1CCC3)CCC2)NS(=O)(=O)/C=C/[C@@H]1CCCN1S(=O)(=O)Cc1ccccc1]

$^1$H NMR (400 MHz, DMSO-d$_6$): δ=7.86 (s, 1H), 7.42 (m, 2H), 7.34 (t, J=4.0 Hz, 3H), 6.87 (s, 1H), 6.71 (s, 1H), 6.45 (m, 1H), 4.46 (s, 2H), 4.37 (d, J=8.0 Hz, 1H), 3.22 (s, 1H), 2.78 (t, J=7.6 Hz, 4H), 2.66 (t, J=7.2 Hz, 4H), 1.99 (m, 1H), 1.95 (m, 4H), 1.74 (m, 3H); MS (ESI): m/z (%)=530 (100%) (M+1).

Example-92

(S,E)-N-((1,2,3,5,6,7-hexahydro-s-indacen-4-yl)carbamoyl)-2-(1-((4-methoxyphenyl)sulfonyl) pyrrolidin-2-yl)ethenesulfonamide

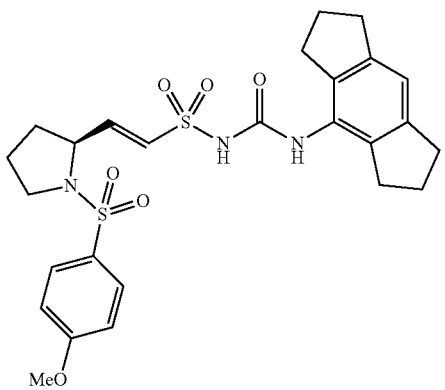 [SMILES: COc1ccc(S(=O)(=O)N2CCC[C@H]2/C=C/S(=O)(=O)NC(=O)Nc2c3c(cc4c2CCC4)CCC3)cc1]

$^1$H NMR (400 MHz, DMSO-d$_6$): δ=7.93 (s, 1H), 7.79 (d, J=2.8 Hz, 2H), 7.12 (d, J=2.0 Hz, 2H), 6.90 (s, 1H), 6.85 (s, 1H), 6.66 (s, 1H), 6.60 (d, J=5.6 Hz, 1H), 6.57 (d, J=4.4 Hz, 1H), 4.4 (m, 1H), 3.84 (s, 3H), 3.22 (m, 1H), 2.78 (t, J=7.2 Hz, 4H), 2.70 (t, J=7.2 Hz, 4H), 1.99 (m, 4H), 1.68 (m, 3H), 1.60 (m, 1H); MS (ESI): m/z (%)=546 (100%) (M+1).

Example-93

(S,E)-N-((1,2,3,5,6,7-hexahydro-s-indacen-4-yl)carbamoyl)-2-(1-((4-fluorophenyl)sulfonyl) pyrrolidin-2-yl)ethenesulfonamide

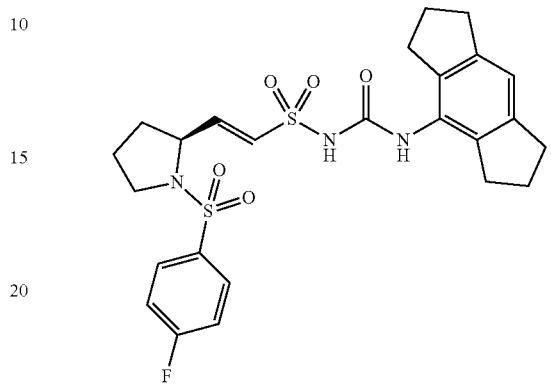

$^1$H NMR (400 MHz, DMSO-d$_6$): δ=8.02 (s, 1H), 7.94 (d, J=2.0 Hz, 2H), 7.47 (d, J=3.6 Hz, 2H), 6.90 (s, 1H), 6.87 (s, 1H), 6.68 (d, J=9.6 Hz, 1H), 4.41 (m, 1H), 3.36 (m, 1H), 2.78 (t, J=7.2 Hz, 4H), 2.69 (t, J=7.2 Hz, 4H), 1.99 (m, 4H), 1.68 (m, 3H), 1.60 (m, 1H); MS (ESI): m/z (%)=534 (100%) (M+1).

Example-94

(S,E)-2-(1-((2-cyanophenyl)sulfonyl)pyrrolidin-2-yl)-N-((1,2,3,5,6,7-hexahydro-s-indacen-4-yl)carbamoyl)ethenesulfonamide

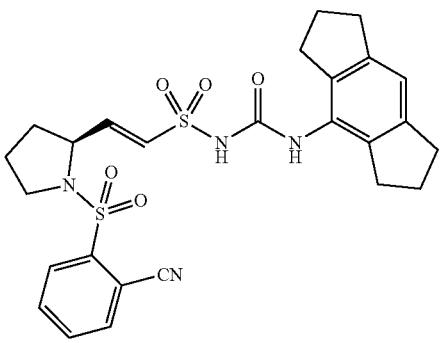 [SMILES: N#Cc1ccccc1S(=O)(=O)N1CCC[C@H]1/C=C/S(=O)(=O)NC(=O)Nc1c2c(cc3c1CCC3)CCC2]

$^1$H NMR (400 MHz, DMSO-d$_6$): δ=8.11 (d, J=1.2 Hz, 2H), 7.90 (d, J=1.2 Hz, 2H), 7.83 (s, 1H), 6.82 (s, 1H), 6.70 (d, J=14.8 Hz, 1H), 6.30 (s, 1H), 4.51 (s, 1H), 3.32 (s, 2H), 2.77 (t, J=7.2 Hz, 4H), 2.70 (t, J=7.2 Hz, 4H), 1.92 (m, 4H), 1.80 (m, 2H), 1.74 (m, 2H); MS (ESI): m/z (%)=541.14 (100%) (M+1).

Example-95

(S,E)-2-(1-(cyclohexylsulfonyl)pyrrolidin-2-yl)-N-((1,2,3,5,6,7-hexahydro-s-indacen-4-yl)carbamoyl)ethenesulfonamide

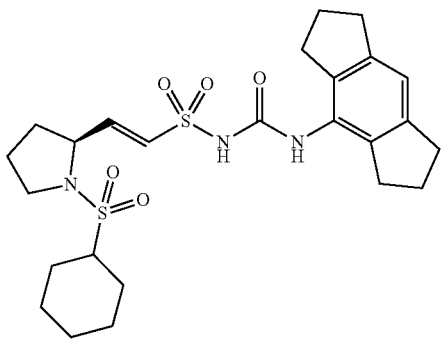 [SMILES: O=C(Nc1c2c(cc3c1CCC3)CCC2)NS(=O)(=O)/C=C/[C@@H]1CCCN1S(=O)(=O)C1CCCCC1]

$^1$H NMR (400 MHz, DMSO-d$_6$): δ=7.78 (s, 1H), 6.85 (s, 1H), 6.70 (d, J=14.8 Hz, 1H), 6.41 (s, 1H), 4.46 (s, 1H), 3.42 (m, 1H), 3.08 (s, 1H), 2.78 (t, J=7.6 Hz, 4H), 2.70 (t, J=7.2 Hz, 4H), 2.09 (d, J=4.8 Hz, 1H) 1.94 (m, 7H), 1.83 (m, 3H), 1.72 (m, 1H), 1.52 (s, 1H), 1.32 (m, 3H), 1.24 (s, 2H), 1.08 (s, 1H); MS (ESI): m/z (%)=522.19 (100%) (M+1).

Example-96

(S,E)-2-(1-(4-fluorobenzyl)pyrrolidin-2-yl)-N-((1,2,3,5,6,7-hexahydro-s-indacen-4-yl)carbamoyl)ethenesulfonamide

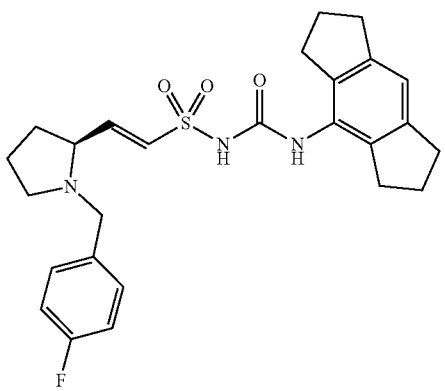 [SMILES: O=C(Nc1c2c(cc3c1CCC3)CCC2)NS(=O)(=O)/C=C/[C@@H]1CCCN1Cc1ccc(F)cc1]

$^1$H NMR (400 MHz, DMSO-d$_6$): δ=8.03 (s, 1H), 7.28 (t, J=6.0 Hz, 2H), 7.06 (t, J=8.8 Hz, 2H), 6.89 (s, 1H), 6.86 (s, 1H), 6.62 (m, 1H), 3.81 (d, J=13.2 Hz, 2H), 3.16 (m, 2H), 2.68 (t, J=5.6 Hz, 4H), 2.62 (t, J=7.2 Hz, 4H), 2.16 (m, 1H), 1.90 (m, 1H), 1.85 (m, 4H), 1.70 (m, 2H), 1.55 (m, 1H); MS (ESI): m/z (%)=484.19 (100%) (M+1).

Example-97

(S,E)-2-(1-((4-cyanophenyl)sulfonyl)pyrrolidin-2-yl)-N-((1,2,3,5,6,7-hexahydro-s-indacen-4-yl)carbamoyl)ethene-1-sulfonamide

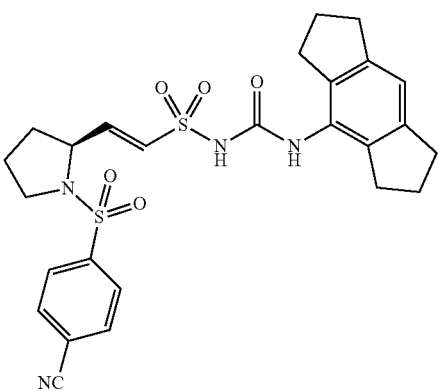 [SMILES: N#Cc1ccc(S(=O)(=O)N2CCC[C@H]2/C=C/S(=O)(=O)NC(=O)Nc2c3c(cc4c2CCC4)CCC3)cc1]

$^1$H NMR (400 MHz, DMSO-d$_6$): δ=8.06 (d, J=8.4 Hz, 2H), 8.01 (t, J=8.6 Hz, 2H), 7.86 (s, 1H), 6.87 (s, 1H), 6.80 (d, J=14.8 Hz, 1H), 6.42 (d, J=9.6 Hz, 1H), 4.44 (t, J=5.6 Hz, 1H), 3.36 (m, 2H), 3.18 (m, 1H), 2.78 (t, J=7.2 Hz, 4H), 2.70 (t, J=7.2 Hz, 4H), 1.92 (m, 4H), 1.67 (m, 3H), 1.56 (m, 1H); MS (ESI): m/z (%)=541.15 (100%) (M+1).

Example-98

(S,E)-2-(1-(4-cyanobenzyl)pyrrolidin-2-yl)-N-((1,2,3,5,6,7-hexahydro-s-indacen-4-yl)carbamoyl)ethene-1-sulfonamide

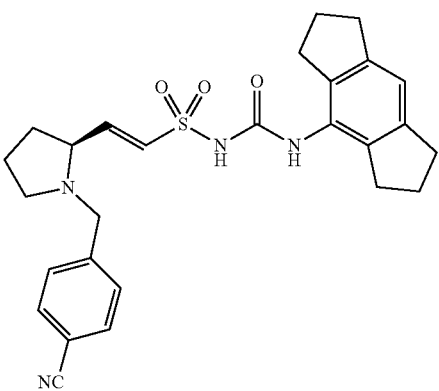 [SMILES: N#Cc1ccc(CN2CCC[C@H]2/C=C/S(=O)(=O)NC(=O)Nc2c3c(cc4c2CCC4)CCC3)cc1]

$^1$H NMR (400 MHz, DMSO-d$_6$): δ=8.01 (s, 1H), 7.89 (d, J=8.4 Hz, 2H), 7.51 (d, J=8.4 Hz, 2H), 6.97 (d, J=6.0 Hz, 1H), 6.91 (s, 1H), 6.65 (m, 1H), 3.86 (d, J=13.6 Hz, 2H), 3.25 (m, 1H), 2.79 (m, 5H), 2.61 (m, 4H), 2.22 (m, 1H), 2.12 (m, 1H), 1.98 (m, 4H), 1.72 (m, 2H), 1.76 (m, 1H); MS (ESI): m/z (%)=491.15 (100%) (M+1).

Example-99

(S,E)-N-((1,2,3,6,7,8-hexahydro-as-indacen-4-yl)carbamoyl)-2-(pyrrolidin-2-yl)ethene-1-sulfonamide

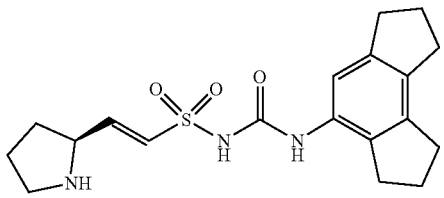 [SMILES: O=C(Nc1cc2c(c3c1CCC3)CCC2)NS(=O)(=O)/C=C/[C@@H]1CCCN1]

$^1$H NMR (400 MHz, DMSO-d$_6$): δ=8.90 (s, 1H), 7.59 (s, 1H), 7.26 (s, 1H), 6.98 (d, J1=0.8 Hz, 1H), 6.98 (t, J2=1.2 Hz, 1H), 6.38 (m, 1H), 4.08 (m, 1H), 3.22 (m, 2H), 2.70 (m, 8H), 2.15 (m, 1H), 1.98 (m, 6H), 1.71 (m, 1H), 1.56 (m, 1H); MS (ESI): m/z (%)=372.87 (100%) (M−1).

Example-100

(E)-N-((1,2,3,5,6,7-hexahydro-s-indacen-4-yl)carbamoyl)-2-(piperidin-2-yl)ethene-1-sulfonamide

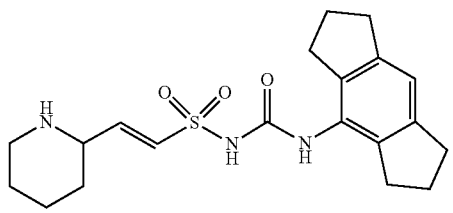 [SMILES: O=C(Nc1c2c(cc3c1CCC3)CCC2)NS(=O)(=O)/C=C/C1CCCCN1]

$^1$H NMR (400 MHz, DMSO-d$_6$): 0=7.41 (s, 1H), 6.86 (d, J=15.6 Hz, 1H), 6.79 (s, 1H), 6.28 (d, J=6.0 Hz, 1H), 3.61 (s, 2H), 3.14 (d, J=12.8 Hz, 1H), 2.81 (t, J=7.2 Hz, 4H), 2.70 (t, J=7.2 Hz, 4H), 1.98 (m, 5H), 1.81 (m, 2H), 1.69 (m, 1H), 1.48 (m, 3H); MS (ESI): m/z (%)=390.13 (100%) (M+1).

Example-101

(E)-N-((1,2,3,5,6,7-hexahydro-s-indacen-4-yl)carbamoyl)-2-(1-methylpiperidin-2-yl)ethene-1-sulfonamide

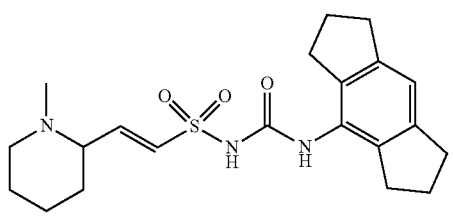 [SMILES: CN1CCCCC1/C=C/S(=O)(=O)NC(=O)Nc1c2c(cc3c1CCC3)CCC2]

$^1$H NMR (400 MHz, DMSO-d$_6$): δ=7.92 (s, 1H), 6.89 (s, 1H), 6.80 (d, J=14.8 Hz, 1H), 6.42 (d, J=8.4 Hz, 1H), 2.92 (t, J=5.2 Hz, 2H), 2.82 (t, J=7.2 Hz, 4H), 2.72 (t, J=7.2 Hz, 4H), 2.27 (m, 4H), 1.92 (m, 5H), 1.62 (m, 3H), 1.44 (s, 2H); MS (ESI): m/z (%)=404.15 (100%) (M+1).

Example-102

(E)-N-((1,2,3,6,7,8-hexahydro-as-indacen-4-yl)carbamoyl)-2-(1-methylpyrrolidin-2-yl)ethene-1-sulfonamide

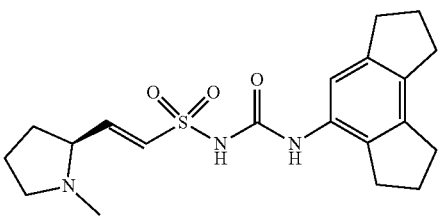 [SMILES: CN1CCC[C@H]1/C=C/S(=O)(=O)NC(=O)Nc1cc2c(c3c1CCC3)CCC2]

1H NMR (400 MHz, DMSO-d6): δ=7.83 (s, 1H), 7.44 (s, 1H), 6.88 (d, J=14.8 Hz, 1H), 6.53 (d, J=8.0 Hz, 1H), 3.13 (s, 3H), 2.82 (t, J=7.2 Hz, 4H), 2.72 (t, J=7.2 Hz, 4H), 2.39 (s, 2H), 2.33 (d, J=2.0 Hz, 3H), 2.11 (m, 5H), 1.81 (m, 2H), 1.78 (m, 1H); MS (ESI): m/z (%)=390.14 (100%) (M+1).

Example-103

(E)-N-((1,2,3,6,7,8-hexahydro-as-indacen-4-yl)carbamoyl)-2-(1-(methylsulfonyl)pyrrolidin-2-yl)ethene-1-sulfonamide

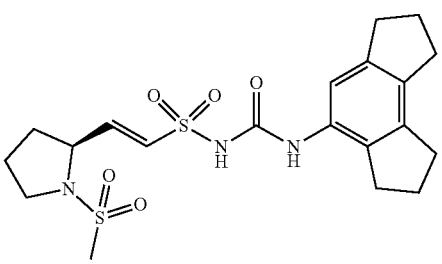 [SMILES: CS(=O)(=O)N1CCC[C@H]1/C=C/S(=O)(=O)NC(=O)Nc1cc2c(c3c1CCC3)CCC2]

$^1$H NMR (400 MHz, DMSO-d$_6$): δ=7.87 (s, 1H), 7.45 (s, 1H), 6.77 (d, J=14.8 Hz, 1H), 6.68 (d, J=4.8 Hz, 1H), 4.48 (t, J=4.0 Hz, 1H), 2.99 (s, 3H), 2.82 (t, J=7.2 Hz, 4H), 2.72 (t, J=7.2 Hz, 4H), 2.11 (m, 5H), 1.81 (m, 3H); MS (ESI): m/z (%)=454.09 (100%) (M+1).

Example-104

((E)-N-((1,2,3,5,6,7-hexahydro-s-indacen-4-yl)carbamoyl)-3-(piperidin-2-yl)prop-1-ene-1-sulfonamide

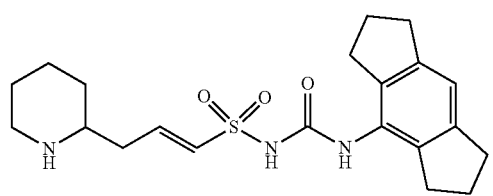 [SMILES: O=C(Nc1c2c(cc3c1CCC3)CCC2)NS(=O)(=O)/C=C/CC1CCCCN1]

$^1$H NMR (400 MHz, DMSO-d$_6$): δ=7.44 (s, 1H), 6.79 (s, 1H), 6.47 (d, J=15.2 Hz, 1H), 6.20 (m, 1H), 2.85 (t, J=7.2 Hz, 5H), 2.70 (t, J=7.2 Hz, 4H), 2.33 (t, J=1.6 Hz, 2H), 1.98

(m, 6H), 1.73 (m, 3H), 1.61 (s, 1H), 1.38 (m, 2H). 1.24 (s, 1H); MS (ESI): m/z (%)=404.20 (100%) (M+1).

Example-105

(S,E)-N-((1,2,3,5,6,7-hexahydro-s-indacen-4-yl)carbamoyl)-2-(2-methylpyrrolidin-2-yl)ethene-1-sulfonamide

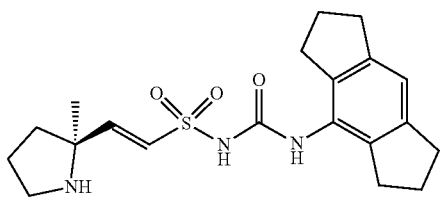 [SMILES: C[C@@]1(/C=C/S(=O)(=O)NC(=O)Nc2c3c(cc4c2CCC4)CCC3)CCCN1]

$^1$H NMR (400 MHz, DMSO-d$_6$): δ=7.52 (s, 1H), 6.88 (d, J=15.6 Hz, 1H), 6.81 (s, 1H), 6.46 (d, J=15.6 Hz, 1H), 3.21 (m, 2H), 3.12 (m, 1H), 2.75 (t, J=7.2 Hz, 4H), 2.69 (t, J=7.2 Hz, 4H), 1.98 (m, 7H), 1.78 (s, 2H), 1.38 (s, 3H); MS (ESI): m/z (%)=390.24 (100%)(M+1).

Example-106

(S,E)-2-(1,2-dimethylpyrrolidin-2-yl)-N-((1,2,3,5,6,7-hexahydro-s-indacen-4-yl)carbamoyl)ethene-1-sulfonamide

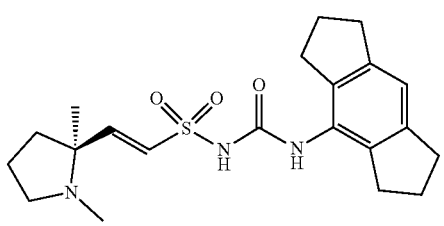 [SMILES: CN1CCC[C@@]1(C)/C=C/S(=O)(=O)NC(=O)Nc1c2c(cc3c1CCC3)CCC2]

1H NMR (400 MHz, DMSO-d6): δ=8.04 (s, 1H), 6.93 (s, 1H), 6.73 (d, J=15.2 Hz, 1H), 6.65 (d, J=15.2 Hz, 1H), 2.80 (t, J=7.2 Hz, 4H), 2.68 (t, J=7.2 Hz, 4H), 2.20 (s, 3H), 1.96 (m, 4H), 1.72 (m, 4H), 1.13 (s, 3H); MS (ESI): m/z (%)=404.25 (100%) (M+1).

Alternatively, Example 106 was also be prepared as per the procedure described for synthesis of Intermediate-7b (Example 111) using Intermediate 9 and (S)-1,2-dimethylpyrrolidine-2-carbaldehyde, together with conventional techniques known to those skilled in the art of organic synthesis.

Example-107

(E)-N-((1,2,3,5,6,7-hexahydro-s-indacen-4-yl)carbamoyl)-2-(indolin-2-yl)ethene-1-sulfonamide

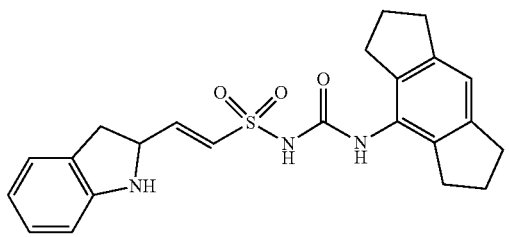 [SMILES: O=C(Nc1c2c(cc3c1CCC3)CCC2)NS(=O)(=O)/C=C/C1Cc2ccccc2N1]

$^1$H NMR (400 MHz, DMSO-d$_6$): δ=7.89 (s, 1H), 7.04 (d, J=3.2 Hz, 1H), 6.99 (d, J=6.8 Hz, 1H), 6.93 (d, J=8.0 Hz, 1H), 6.82 (d, J=8.0 Hz, 1H), 6.62 (d, J=13.8 Hz, 1H), 6.51 (d, J=7.6 Hz, 2H), 5.95 (s, 1H), 4.4 (t, J=7.2 Hz, 4H), 2.67 (t, J=7.2 Hz, 4H), 1.95 (m, 1H); MS (ESI): m/z (%)=424.20 (100%) (M+1).

Example-108 tert-butyl(E)-2-(2-(N-((1,2,3,5,6,7-hexahydro-s-indacen-4-yl)carbamoyl)sulfamoyl)vinyl)indoline-1-carboxylate

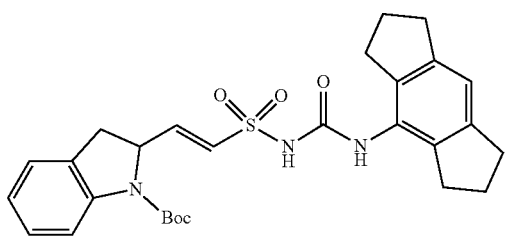 [SMILES: CC(C)(C)OC(=O)N1c2ccccc2CC1/C=C/S(=O)(=O)NC(=O)Nc1c2c(cc3c1CCC3)CCC2]

$^1$H NMR (400 MHz, DMSO-d$_6$): δ=8.11 (s, 1H), 7.71 (s, 1H), 7.20 (d, J=8.8 Hz, 1H), 7.17 (s, 1H), 6.99 (d, J1=0.8 Hz, 1H), 6.97 (d, J2=0.8 Hz, 1H), 6.95 (s, 1H), 6.78 (d, J=6.0 Hz, 1H), 6.66 (d, J=15.6 Hz, 1H), 5.10 (m, 1H), 5.12 (m, 1H), 3.50 (m, 1H), 2.80 (t, J=7.2 Hz, 5H), 2.62 (t, J=7.2 Hz, 4H), 1.96 (m, 5H), 1.45 (s, 10H); MS (ESI): m/z (%)=522.20 (100%) (M−1).

Example-109

((S,E)-2-(1-(cyclopropylmethyl)-2-methylpyrrolidin-2-yl)-N-((1,2,3,5,6,7-hexahydro-s-indacen-4-yl)carbamoyl)ethene-1-sulfonamide

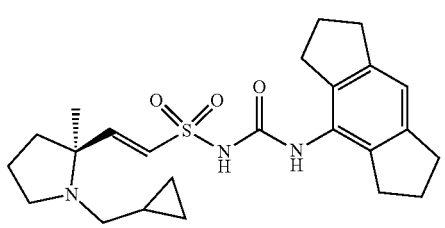 [SMILES: C[C@@]1(/C=C/S(=O)(=O)NC(=O)Nc2c3c(cc4c2CCC4)CCC3)CCCN1CC1CC1]

¹H NMR (400 MHz, DMSO-d6): δ=7.42 (s, 1H), 6.78 (s, 1H), 6.57 (d, J=15.6 Hz, 1H), 6.21 (d, J=15.2 Hz, 1H), 2.93 (t, J=6.4 Hz, 1H), 2.76 (t, J=7.2 Hz, 4H), 2.69 (t, J=7.2 Hz, 4H), 2.33 (t, J=1.62 Hz, 1H), 2.27 (t, J=6.8 Hz, 1H), 2.01 (m, 1H), 1.93 (m, 4H), 1.76 (d, J=5.62 Hz, 1H), 1.68 (d, J=8.0 Hz, 1H), 1.60 (d, J=4.4 Hz, 1H), 1.0 (s, 2H), 0.38 (t, J=7.6 Hz, 2H); MS (ESI): m/z (%)=444.26 (100%) (M+1).

Example-110

(S,E)-2-(1-(cyclopropylsulfonyl)pyrrolidin-2-yl)-N-((1,2,3,5,6,7-hexahydro-s-indacen-4-yl)carbamoyl) ethene-1-sulfonamide

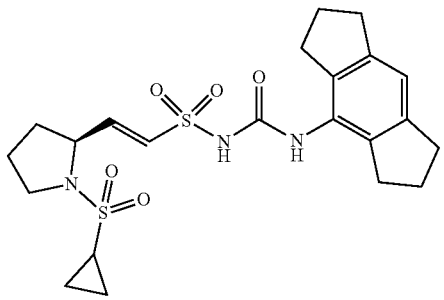 [SMILES: O=C(Nc1c2c(cc3c1CCC3)CCC2)NS(=O)(=O)/C=C/[C@@H]1CCCN1S(=O)(=O)C1CC1]

¹H NMR (400 MHz, DMSO-d6): δ=8.05 (s, 1H), 6.94 (s, 1H), 6.81 (d, J=0.8 Hz, 1H), 6.77 (d, J=1.2 Hz, 1H), 6.68 (d, J=15.2 Hz, 1H), 4.57 (m, 1H), 3.43 (m, 1H), 2.80 (t, J=7.2 Hz, 1H), 2.68 (t, J=7.2 Hz, 4H), 1.99 (m, 5H), 1.81 (m, 2H), 0.95 (d, J=6.4 Hz, 4H); MS (ESI): m/z (%)=480.20 (100%) (M+1).

Example-111 tert-butyl(S,E)-2-(2-(N-((1,2,3,5,6,7-hexahydro-s-indacen-4-yl)carbamoyl)sulfamoyl)vinyl)-2-methylpyrrolidine-1-carboxylate

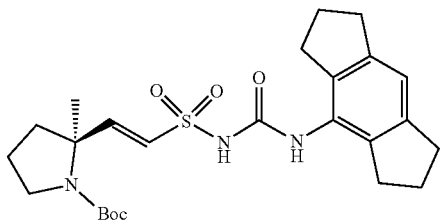 [SMILES: CC(C)(C)OC(=O)N1CCC[C@@]1(C)/C=C/S(=O)(=O)NC(=O)Nc1c2c(cc3c1CCC3)CCC2]

¹H NMR (400 MHz, DMSO-d₆): δ=7.97 (s, 1H), 6.91 (s, 1H), 6.72 (d, J=15.2 Hz, 1H), 6.54 (d, J=7.68 Hz, 1H), 2.80 (t, J=7.2 Hz, 4H), 2.68 (t, J=7.2 Hz, 5H), 1.97 (m, 4H), 1.89 (s, 3H), 1.80 (m, 4H), 1.48 (s, 2H0, 1.44 (s, 2H), 1.38 (s, 10H); MS (ESI): m/z (%)=488.24 (100%) (M-1).

Example-112 tert-butyl(R,E)-2-(2-(N-((2,6-diisopropylphenyl) carbamoyl)sulfamoyl)vinyl)-2-methylpyrrolidine-1-carboxylate

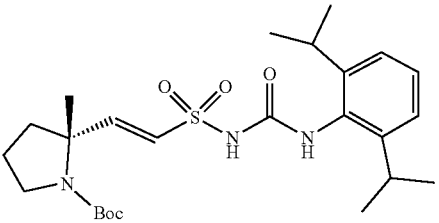 [SMILES: CC(C)c1cccc(C(C)C)c1NC(=O)NS(=O)(=O)/C=C/[C@@]1(C)CCCN1C(=O)OC(C)(C)C]

¹H NMR (400 MHz, DMSO-d₆): δ=10.55 (s, 1H), 7.89 (d, J=16.0 Hz, 1H), 7.27 (t, J=7.6 Hz, 1H), 7.16 (d, J=7.6 Hz, 2H), 6.89-6.79 (m, 1H), 6.56-6.49 (m, 1H), 3.39-3.35 (m, 2H), 3.05-3.00 (m, 2H), 1.93-1.90 (m, 1H), 1.83-1.77 (m, 2H), 1.69-1.64 (m, 1H), 1.44 (s, 3H), 1.37 (s, 9H), 1.13 (d, J=6.8 Hz, 12H); MS (ESI): m/z (%)=492.24 (100%) (M−1)⁻.

Example-113

(R,E)-N-((2,6-diisopropylphenyl)carbamoyl)-2-(2-methylpyrrolidin-2-yl)ethene-1-sulfonamide 2,2,2-trifluoroacetate

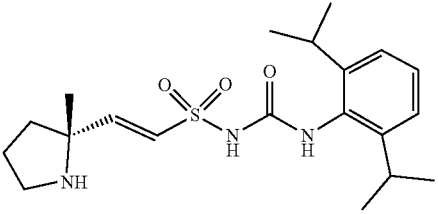 [SMILES: CC(C)c1cccc(C(C)C)c1NC(=O)NS(=O)(=O)/C=C/[C@@]1(C)CCCN1]

¹H NMR (400 MHz, DMSO-d₆): δ=11.10 (bs, 1H), 9.08 (bs, 2H), 8.24 (s, 1H), 7.27 (t, J=7.6 Hz, 1H), 7.16 (d, J=7.6 Hz, 2H), 7.11 (d, J=15.6 Hz, 1H), 7.05 (d, J=15.2 Hz, 1H), 3.33-3.29 (m, 2H), 3.07-3.00 (m, 2H), 2.13-1.83 (m, 4H), 1.46 (s, 3H), 1.12 (d, J=6.8 Hz, 12H); MS (ESI): m/z (%)=392.22 (100%) (M-TFA)⁺;

Example-114

(R,E)-N-((2,6-diisopropylphenyl)carbamoyl)-2-(1,2-dimethylpyrrolidin-2-yl)ethene-1-sulfonamide

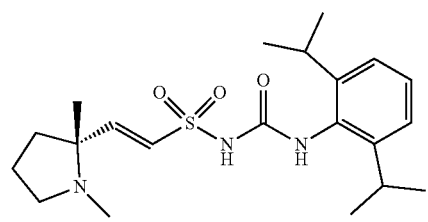 [SMILES: CC(C)c1cccc(C(C)C)c1NC(=O)NS(=O)(=O)/C=C/[C@@]1(C)CCCN1C]

¹H NMR (400 MHz, DMSO-d₆): δ=10.45 (bs, 1H), 7.83 (s, 1H), 7.25 (t, J=7.6 Hz, 1H), 7.15 (d, J=8.0 Hz, 2H), 6.73 (d, J=15.2 Hz, 1H), 6.68 (d, J=15.6 Hz, 1H), 3.33-3.22 (m, 2H), 2.83-2.80 (m, 1H), 2.73-2.67 (m, 1H), 2.15 (s, 3H), 1.80-1.69 (m, 4H), 1.18-1.10 (m, 15H); MS (ESI): m/z (%)=408.23 (100%) (M+H)⁺.

Example-115

(S,E)-2-(1-ethyl-2-methylpyrrolidin-2-yl)-N-((1,2,3,5,6,7-hexahydro-s-indacen-4-yl)carbamoyl)ethene-1-sulfonamide

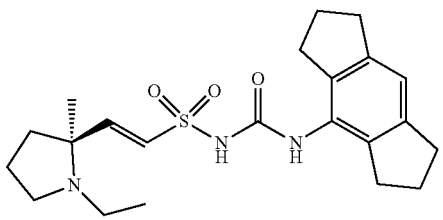 [SMILES: CCN1CCC[C@@]1(C)/C=C/S(=O)(=O)NC(=O)Nc1c2c(cc3c1CCC3)CCC2]

¹H NMR (400 MHz, DMSO-d₆): δ=10.45 (bs, 1H), 8.05 (bs, 1H), 6.93 (s, 1H), 6.74 (d, J=15.2 Hz, 1H), 6.68 (d, J=15.6 Hz, 1H), 2.96-2.89 (m, 2H), 2.80 (t, J=7.2 Hz, 4H), 2.67 (t, J=7.6 Hz, 6H), 1.96 (quin, J=7.2 Hz, 4H), 1.79-1.72 (m, 4H), 1.14 (s, 3H), 1.02 (t, J=6.4 Hz, 3H); MS (ESI): m/z (%)=418.16 (100%) (M+H)⁺.

Example-116

Bissodium (R,E)-((2-(1,2-dimethylpyrrolidin-2-yl)vinyl)sulfonyl((1,2,3,5,6,7-hexahydro-s-indacen-4-yl)carbamoyl)amide

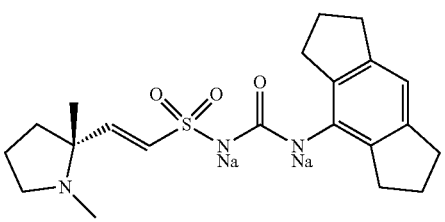

¹H NMR (400 MHz, DMSO-d₆): δ=6.76 (s, 1H), 6.56 (d, J=15.6 Hz, 1H), 6.20 (d, J=15.6 Hz, 1H), 2.75 (t, J=7.6 Hz, 5H), 2.69 (t, J=7.2 Hz, 4H), 2.64-2.59 (m, 1H), 2.08 (s, 3H), 1.90 (quin, J=7.2 Hz, 4H), 1.74-1.68 (m, 3H), 1.62-1.61 (m, 1H), 1.01 (s, 3H); MS (ESI): m/z (%)=404.17 (100%) (M−2Na)⁺.

Example-117

Sodium(R,E)-((2-(1,2-dimethylpyrrolidin-2-yl)vinyl)sulfonyl)((1,2,3,5,6,7-hexahydro-s-indacen-4-yl)carbamoyl)amide

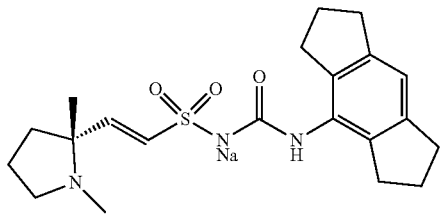

¹H NMR (400 MHz, DMSO-d₆): δ=7.36 (s, 1H), 6.77 (s, 1H), 6.57 (d, J=15.6 Hz, 1H), 6.19 (d, J=15.6 Hz, 1H), 2.76 (t, J=7.2 Hz, 5H), 2.69 (t, J=7.2 Hz, 4H), 2.64-2.59 (m, 1H), 2.08 (s, 3H), 1.91 (quin, J=7.6 Hz, 4H), 1.74-1.68 (m, 3H), 1.62-1.60 (m, 1H), 1.01 (s, 3H); MS (ESI): m/z (%)=404.17 (100%) (M−Na)⁺.

Example-118 tert-butyl(S,E)-2-(2-(N-((2,6-diisopropylphenyl)carbamoyl)sulfamoyl)vinyl)-2-methylpyrrolidine-1-carboxylate

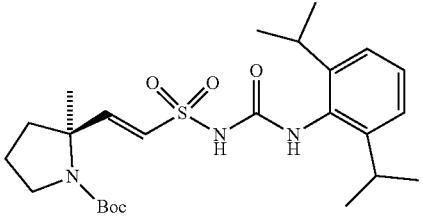 [SMILES: CC(C)c1cccc(C(C)C)c1NC(=O)NS(=O)(=O)/C=C/[C@]1(C)CCCN1C(=O)OC(C)(C)C]

¹H NMR (400 MHz, DMSO-d₆): δ=10.55 (s, 1H), 7.89 (s, 1H), 7.27 (t, J=7.6 Hz, 1H), 7.16 (d, J=7.6 Hz, 2H), 6.84 (d, J=15.6 Hz, 1H), 6.56 (d, J=15.6 Hz, 1H), 3.37 (t, J=6.4 Hz, 2H), 3.03 (t, J=6.4 Hz, 2H), 1.91-1.90 (m, 1H), 1.83-1.77 (m, 2H), 1.69-1.64 (m, 1H), 1.44 (s, 3H), 1.37 (s, 9H), 1.13 (d, J=6.8 Hz, 12H); MS (ESI): m/z (%)=494.31 (10%) (M+1)⁺.

Example-119

(S,E)-N-((2,6-diisopropylphenyl)carbamoyl)-2-(2-methylpyrrolidin-2-yl)ethene-1-sulfonamide 2,2,2-trifluoroacetate

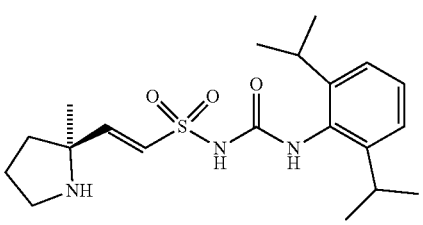 [SMILES: CC(C)c1cccc(C(C)C)c1NC(=O)NS(=O)(=O)/C=C/[C@]1(C)CCCN1]

¹H NMR (400 MHz, DMSO-d₆): δ=11.10 (bs, 1H), 9.10 (bs, 2H), 8.28 (s, 1H), 7.27 (t, J=7.6 Hz, 1H), 7.16 (d, J=7.6 Hz, 2H), 7.12 (d, J=15.6 Hz, 1H), 7.00 (d, J=15.2 Hz, 1H), 3.35-3.30 (m, 1H), 3.24-3.20 (m, 1H), 3.07-3.00 (m, 2H), 2.10-1.98 (m, 2H), 1.93-1.85 (m, 2H), 1.46 (s, 3H), 1.12 (d, J=6.8 Hz, 12H); MS (ESI): m/z (%)=394.27 (100%) (M-TFA)⁺.

Example-120

(S,E)-N-((2,6-diisopropylphenyl)carbamoyl)-2-(1,2-dimethylpyrrolidin-2-yl)ethene-1-sulfonamide

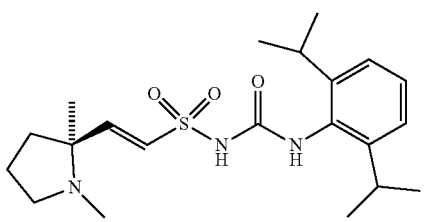 [SMILES: CC(C)c1cccc(C(C)C)c1NC(=O)NS(=O)(=O)/C=C/[C@]1(C)CCCN1C]

¹H NMR (400 MHz, DMSO-d₆): δ=10.10 (bs, 1H), 7.92 (s, 1H), 7.25 (t, J=7.6 Hz, 1H), 7.13 (d, J=7.6 Hz, 2H), 6.68 (d, J=14.8 Hz, 1H), 6.61 (d, J=15.6 Hz, 1H), 3.07-3.02 (m, 2H), 2.85-2.83 (m, 1H), 2.69-2.67 (m, 1H), 2.14 (s, 3H), 1.82-1.66 (m, 4H), 1.12-1.07 (m, 15H); MS (ESI): m/z (%)=408.23 (100%) (M+H)⁺.

Example-121

(R,E)-N-((1,2,3,5,6,7-hexahydro-s-indacen-4-yl)carbamoyl)-2-(2-methyl-1-(oxetan-3-yl)pyrrolidin-2-yl)ethene-1-sulfonamide

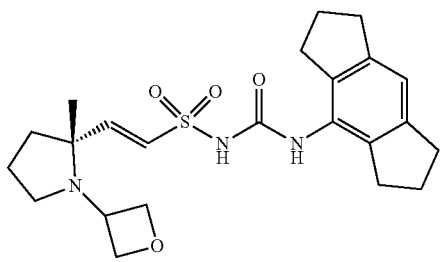 [SMILES: C[C@]1(/C=C/S(=O)(=O)NC(=O)Nc2c3c(cc4c2CCC4)CCC3)CCCN1C1COC1]

¹H NMR (400 MHz, DMSO-d₆): δ=10.39 (bs, 1H), 8.14 (s, 1H), 6.95 (s, 1H), 6.71-6.59 (m, 2H), 4.65 (t, J=6.4 Hz, 1H), 4.55 (t, J=6.8 Hz, 1H), 4.45-4.39 (m, 2H), 4.05-3.98 (m, 1H), 3.13-3.07 (m, 1H), 3.02-2.99 (m, 1H), 2.81 (t, J=7.2 Hz, 4H), 2.69 (t, J=7.2 Hz, 4H), 2.01-1.63 (m, 8H), 1.03 (s, 3H); MS (ESI): m/z (%)=446.24 (100%) (M+H)⁺.

Example-122 tert-butyl (S,E)-2-(2-(N-((4-fluoro-2,6-diisopropylphenyl)carbamoyl)sulfamoyl)vinyl)-2-methylpyrrolidine-1-carboxylate

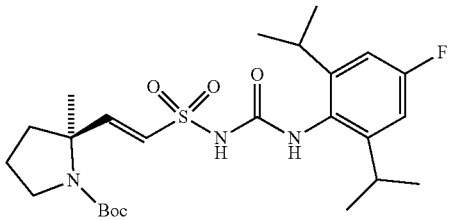 [SMILES: CC(C)c1cc(F)cc(C(C)C)c1NC(=O)NS(=O)(=O)/C=C/[C@]1(C)CCCN1C(=O)OC(C)(C)C]

¹H NMR (400 MHz, DMSO-ds): δ=10.61 (bs, 1H), 7.89-7.85 (m, 1H), 6.97 (d, J=10 Hz, 2H), 6.90-6.79 (m, 1H), 6.55-6.49 (m, 1H), 3.38-3.35 (m, 2H), 3.03-3.01 (m, 2H), 1.92-1.64 (m, 3H), 1.47-1.43 (m, 3H), 1.36 (s, 9H), 1.11 (d, J=7.2 Hz, 12H); MS (ESI): m/z (%)=512.30 (8%) (M+H)⁺, 534.29 (8%) (M+Na)⁺.

Example-123

(S,E)-N-((4-fluoro-2,6-diisopropylphenyl)carbamoyl)-2-(2-methylpyrrolidin-2-yl)ethene-1-sulfonamide 2,2,2-trifluoroacetate

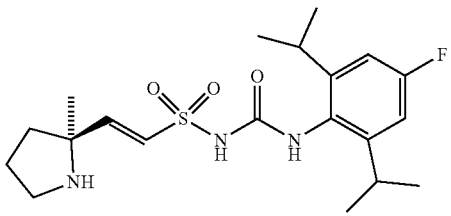 [SMILES: CC(C)c1cc(F)cc(C(C)C)c1NC(=O)NS(=O)(=O)/C=C/[C@]1(C)CCCN1]

¹H NMR (400 MHz, DMSO-d₆): δ=11.11 (bs, 1H), 9.08 (bs, 2H), 8.25 (s, 1H), 7.09 (d, J=15.6 Hz, 1H); 7.00-6.95 (m, 3H), 3.42-3.40 (m, 1H), 3.21-3.17 (m, 1H), 3.06-2.99 (m, 2H), 2.10-1.83 (m, 4H), 1.45 (s, 3H), 1.11 (d, J=5.6 Hz, 12H); MS (ESI): m/z (%)=412.23 (100%) (M+H)⁺;

Example-124

(S,E)-2-(1,2-dimethylpyrrolidin-2-yl)-N-((4-fluoro-2,6-diisopropylphenyl)carbamoyl)ethene-1-sulfonamide

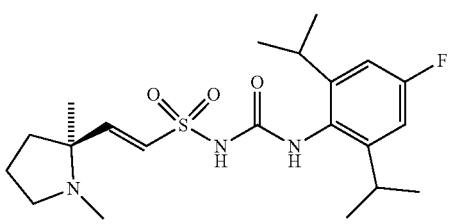 [SMILES: CC(C)c1cc(F)cc(C(C)C)c1NC(=O)NS(=O)(=O)/C=C/[C@]1(C)CCCN1C]

¹H NMR (400 MHz, DMSO-d₆): δ=7.87 (s, 1H), 6.93 (d, J=10 Hz, 2H); 6.66-6.92 (m, 2H), 3.10-3.04 (m, 2H), 2.83-2.67 (m, 2H), 2.15 (s, 3H), 1.76-1.69 (m, 4H), 1.11-1.09 (m, 15H); MS (ESI): m/z (%)=426.29 (100%) (M+H)⁺;

Example-125

(E)-2-(1-acetylazetidin-2-yl)-N-((1,2,3,5,6,7-hexahydro-s-indacen-4-yl)carbamoyl)ethene-1-sulfonamide

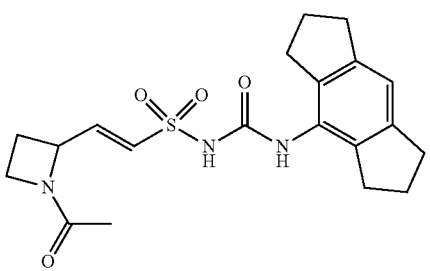 [SMILES: CC(=O)N1CCC1/C=C/S(=O)(=O)NC(=O)Nc1c2c(cc3c1CCC3)CCC2]

¹H NMR (400 MHz, DMSO-d₆): δ=10.40 (br s, 1H), 8.15-8.09 (m, 1H), 6.96-6.71 (m, 3H), 5.14-4.87 (m, 1H), 2.81 (t, J=7.2 Hz, 4H), 2.77-2.64 (m, 4H), 2.60-2.56 (m, 1H), 2.01-1.94 (m, 5H), 1.78 (s, 2H), 1.66 (s, 1H); MS (ESI): m/z (%)=404.11 (100%)(M+H)⁺.

Example-126 tert-butyl(R,E)-(2-(2-(2-(N-((1,2,3,5,6,7-hexahydro-s-indacen-4-yl)carbamoyl)sulfamoyl)vinyl)pyrrolidin-1-yl)ethyl)(methyl)carbamate

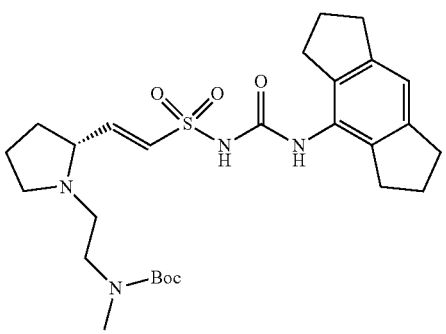 [SMILES: CN(CCN1CCC[C@@H]1/C=C/S(=O)(=O)NC(=O)Nc1c2c(cc3c1CCC3)CCC2)C(=O)OC(C)(C)C]

¹H NMR (400 MHz, DMSO-d₆): δ=10.38 (brs, 1H), 8.05 (s, 1H), 6.95 (s, 1H), 6.80 (d, J=14.4 Hz, 1H), 6.63 (dd, J=14.8 Hz J=6.8 Hz, 1H), 3.23-3.07 (m, 4H), 2.81 (t, J=7.2 Hz, 4H), 2.72-2.58 (m, 8H), 2.33-2.18 (m, 2H), 2.03-1.91 (m, 5H), 1.83-1.62 (m, 2H), 1.55-1.46 (m, 1H), 1.37 (s, 9H); MS (ESI): m/z (%)=533.21 (100%) (M+H)⁺.

Example-127

(S,E)-2-(1-allylpyrrolidin-2-yl)-N-((1,2,3,5,6,7-hexahydro-s-indacen-4-yl)carbamoyl)ethene-1-sulfonamide

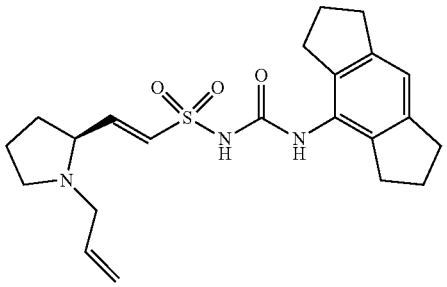 [SMILES: C=CCN1CCC[C@H]1/C=C/S(=O)(=O)NC(=O)Nc1c2c(cc3c1CCC3)CCC2]

¹H NMR (400 MHz, DMSO-d₆): δ=8.07 (s, 1H), 6.95 (s, 1H), 6.84 (d, J=15.2 Hz, 1H), 6.64 (dd, J=15.2 Hz, J=7.2 Hz, 1H), 5.85-5.80 (m, 1H), 5.19-5.14 (m, 1H), 5.09-5.07 (m, 1H), 3.28-3.27 (m, 1H), 3.21-3.15 (m, 1H), 3.05-3.01 (m, 1H), 2.86-2.78 (m, 4H), 2.73-2.64 (m, 4H), 2.60-2.56 (m, 1H), 2.30-2.23 (m, 1H), 2.07-1.97 (m, 5H), 1.80-1.70 (m, 2H), 1.59-1.50 (m, 1H); MS (ESI): m/z (%)=416.14 (100%) (M+H)⁺.

Example-128

(S,E)-2-(1-(1H-benzo[d]imidazole-6-carbonyl)pyrrolidin-2-yl)-N-((1,2,3,5,6,7-hexahydro-s-indacen-4-yl)carbamoyl)ethene-1-sulfonamide

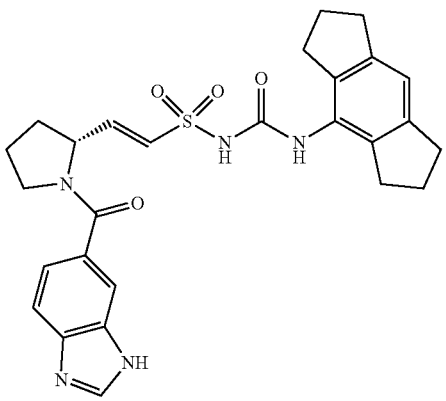 [SMILES: O=C(Nc1c2c(cc3c1CCC3)CCC2)NS(=O)(=O)/C=C/[C@H]1CCCN1C(=O)c1ccc2nc[nH]c2c1]

¹H NMR (400 MHz, DMSO-d₆): δ=12.65 (brs, 1H), 8.40 (s, 1H), 8.04 (s, 1H), 7.85-7.69 (m, 1H), 7.67-7.50 (m, 1H), 7.49-7.23 (m, 1H), 6.92 (s, 1H), 6.91-6.53 (m, 2H), 4.98-4.68 (m, 1H), 3.72-3.53 (m, 1H), 3.50-3.42 (m, 1H), 2.86-2.72 (m, 4H), 2.66 (t, J=6.8 Hz, 4H), 2.29-2.12 (m, 1H), 1.98-1.77 (m, 7H); MS (ESI): m/z (%)=520.24 (90%) (M+H)⁺.

Example-129

(S,E)-2-(1-(cyclopropylsulfonyl)-2-methylpyrrolidin-2-yl)-N-((1,2,3,5,6,7-hexahydro-s-indacen-4-yl)carbamoyl)ethene-1-sulfonamide

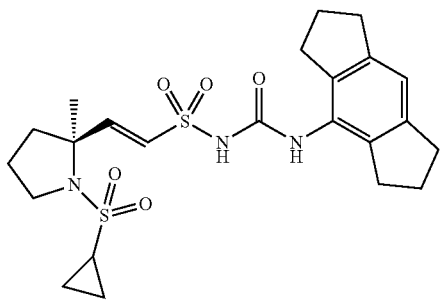 [SMILES: C[C@@]1(/C=C/S(=O)(=O)NC(=O)Nc2c3c(cc4c2CCC4)CCC3)CCCN1S(=O)(=O)C1CC1]

$^1$H NMR (400 MHz, DMSO-d$_6$): δ=8.01 (s, 1H), 6.94 (s, 1H), 6.86 (d, J=15.2 Hz, 1H), 6.71 (dd, J=14.8 Hz, J=6.4 Hz, 1H), 3.46 (t, J=6.8 Hz, 2H), 2.80 (t, J=7.2 Hz, 4H), 2.68 (t, J=7.2 Hz, 4H), 2.63-2.56 (m, 2H), 2.07-1.91 (m, 6H), 1.90-1.74 (m, 1H), 1.57 (s, 3H), 0.97-0.89 (m, 4H); MS (ESI): m/z (%)=494.22 (100%) (M+H)$^+$.

Example-130

(S,E)-N-((1,2,3,5,6,7-hexahydro-s-indacen-4-yl)carbamoyl)-2-(1-(4-methoxybenzyl)pyrrolidin-2-yl)ethene-1-sulfonamide

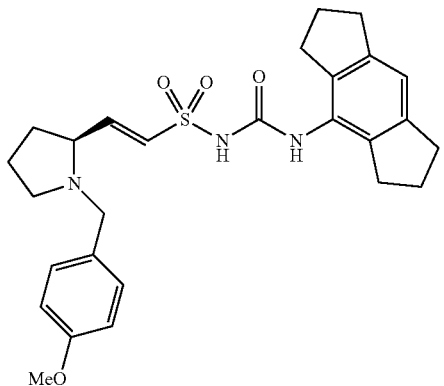 [SMILES: COc1ccc(CN2CCC[C@H]2/C=C/S(=O)(=O)NC(=O)Nc2c3c(cc4c2CCC4)CCC3)cc1]

$^1$H NMR (400 MHz, DMSO-d$_6$): δ=8.01 (s, 1H), 7.20 (d, J=8.4 Hz, 2H), 7.16 (d, J=8.4 Hz, 2H), 6.97 (d, J=6.0 Hz, 1H), 6.91 (s, 1H), 6.65 (m, 1H), 3.86 (d, J=13.6 Hz, 2H), 3.25 (m, 1H), 2.80 (t, J=7.2 Hz, 1H), 2.68 (t, J=7.2 Hz, 4H), 2.12 (m, 1H), 1.98 (m, 4H), 1.72 (m, 2H), 1.76 (m, 1H); MS (ESI): m/z (%)=496.33 (100%) (M+1).

Example-131 tert-butyl 5-((R)-2-((E)-2-(N-((1,2,3,5,6,7-hexahydro-s-indacen-4-yl)carbamoyl)sulfamoyl)vinyl)pyrrolidin-1-yl)hexahydrocyclopenta[c]pyrrole-2(1H)-carboxylate

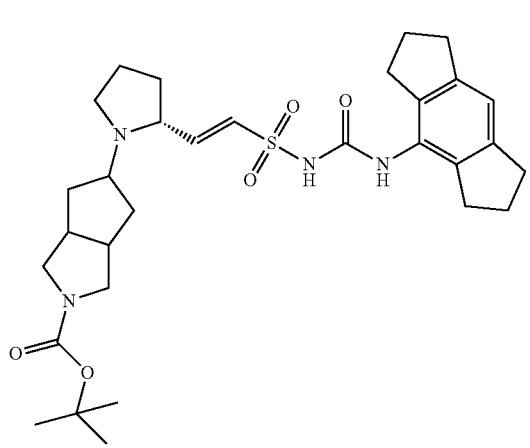 [SMILES: CC(C)(C)OC(=O)N1CC2CC(N3CCC[C@@H]3/C=C/S(=O)(=O)NC(=O)Nc3c4c(cc5c3CCC5)CCC4)CC2C1]

$^1$H NMR (400 MHz, DMSO-d$_6$): δ=10.34 (brs, 1H), 8.03 (s, 1H), 6.94 (s, 1H), 6.84 (d, J=14.8 Hz, 1H), 6.66 (dd, J=14.8 Hz, J=7.6 Hz, 1H), 3.48-3.35 (m, 1H), 3.14-3.07 (m, 2H), 3.99-2.88 (m, 2H), 2.81 (t, J=6.8 Hz, 4H), 2.69-2.66 (m, 5H), 2.47-2.39 (m, 3H), 2.01-1.91 (m, 7H), 1.81-1.69 (m, 2H), 1.66-1.50 (m, 2H), 1.38 (s, 9H), 1.31-1.08 (m, 2H); MS (ESI): m/z (%)=585.29 (100%) (M+H)$^+$.

Example-132

(E)-N-((1,2,3,5,6,7-hexahydro-s-indacen-4-yl)carbamoyl)-2-((2R)-1-(octahydrocyclo-penta[c]pyrrol-5-yl)pyrrolidin-2-yl)ethene-1-sulfonamide 2,2,2-trifluoroacetate

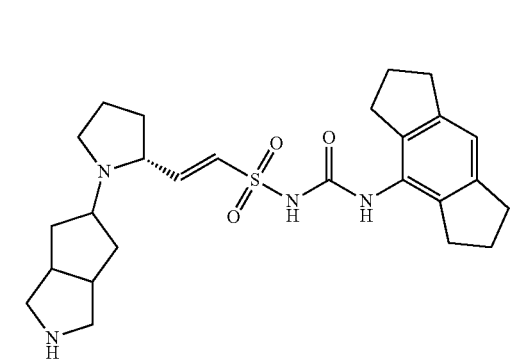 [SMILES: O=C(Nc1c2c(cc3c1CCC3)CCC2)NS(=O)(=O)/C=C/[C@H]1CCCN1C1CC2CNCC2C1]

$^1$H NMR (400 MHz, DMSO-d$_6$): δ=10.54 (brs, 1H), 9.08 (s, 1H), 8.57 (s, 2H), 7.24-7.22 (m, 1H), 6.97 (s, 1H), 6.91-6.81 (m, 1H), 4.50-4.28 (m, 1H), 3.63-3.45 (m, 2H), 3.39-3.16 (m, 2H), 3.17-2.93 (m, 2H), 2.82 (t, J=7.2 Hz, 4H), 2.77-2.64 (m, 5H), 2.38-2.09 (m, 3H), 2.01-1.91 (m, 6H), 1.90-1.78 (m, 1H), 1.62-1.39 (m, 2H), 1.05-1.03 (m, 2H); MS (ESI): m/z (%)=485.25 (100%) (M+H)$^+$.

Example-133

(E)-2-(1-(cyclopropylsulfonyl)azetidin-2-yl)-N-((1,2,3,5,6,7-hexahydro-s-indacen-4-yl)carbamoyl)ethene-1-sulfonamide

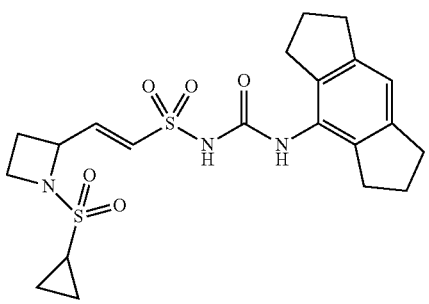 [SMILES: O=C(Nc1c2c(cc3c1CCC3)CCC2)NS(=O)(=O)/C=C/C1CCN1S(=O)(=O)C1CC1]

¹H NMR (400 MHz, DMSO-d₆): δ=10.54 (brs, 1H), 8.12 (s, 1H), 6.97-6.93 (m, 2H), 6.86 (dd, J=15.2 Hz, J=4.8 Hz, 1H), 5.08-5.02 (m, 1H), 4.05-3.99 (m, 1H), 3.66-3.61 (m, 1H), 2.81 (t, J=7.2 Hz, 4H), 2.78-2.73 (m, 1H), 2.68 (t, J=7.2 Hz, 4H), 2.46-2.43 (m, 1H), 2.15-2.10 (m, 1H), 2.01-1.94 (m, 4H), 1.05-0.98 (m, 2H), 0.94-0.90 (m, 2H); MS (ESI): m/z (%)=466.08 (100%) (M+H)⁺.

Example-134

(S,E)-N-((2,6-diisopropylphenyl)carbamoyl)-2-(1-(thiazol-2-yl)pyrrolidin-2-yl)ethene-1-sulfonamide

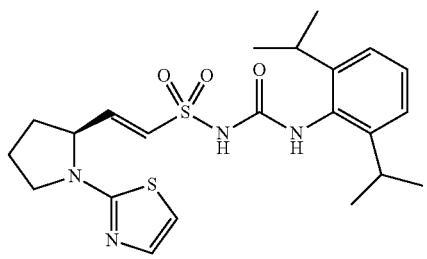 [SMILES: CC(C)c1cccc(C(C)C)c1NC(=O)NS(=O)(=O)/C=C/[C@@H]1CCCN1c1nccs1]

¹H NMR (400 MHz, DMSO-d₆): δ=10.59 (bs, 1H), 7.92 (s, 1H), 7.28-7.25 (m, 1H), 7.16-7.13 (m, 3H), 6.85-6.76 (m, 2H), 6.66 (d, J=15.2 Hz, 1H), 4.57-4.55 (m, 1H), 3.51-3.50 (m, 1H), 3.39-3.37 (m, 1H), 3.05-2.98 (m, 2H), 2.23-2.19 (m, 1H), 1.99-1.83 (m, 3H), 1.11 (d, J=6.8 Hz, 12H); MS (ESI): m/z (%)=463.16 (100%) (M+H)⁺.

Example-135 tert-butyl(S,E)-(2-(2-(2-(N-((1,2,3,5,6,7-hexahydro-s-indacen-4-yl)carbamoyl)sulfamoyl)vinyl)-2-methylpyrrolidin-1-yl)ethylxmethyl)carbamate

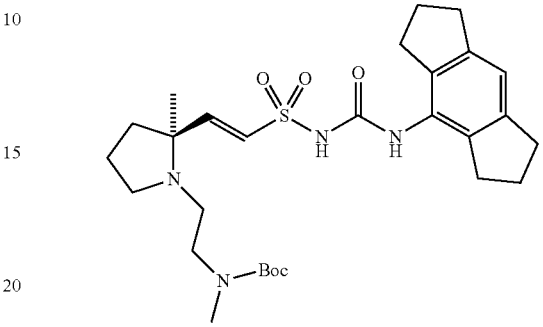

¹H NMR (400 MHz, DMSO-d₆): δ=10.37 (bs, 1H), 8.06 (s, 1H), 6.95 (s, 1H), 6.72 (d, J=15.6 Hz, 1H), 6.66 (d, J=15.6 Hz, 1H), 3.2-3.17 (m, 1H), 2.81 (t, J=6.8 Hz, 4H), 2.68-2.65 (m, 8H), 2.43-2.42 (m, 1H), 1.96 (quin, J=7.2 Hz, 4H), 1.75-1.65 (m, 4H), 1.41-1.37 (m, 12H), 1.1 (s, 3H); MS (ESI): m/z (%)=547.32 (100%) (M+H)⁺.

Example-136 potassium (R,E)-((2-(1,2-dimethylpyrrolidin-2-yl)vinyl)sulfonyl)((1,2,3,5,6,7-hexahydro-s-indacen-4-yl)carbamoyl)amide

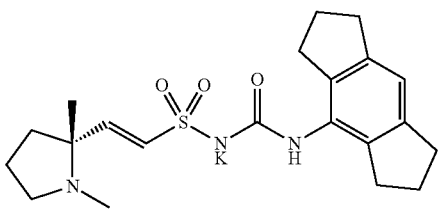

¹H NMR (400 MHz, DMSO-d₆): δ=7.33 (s, 1H), 6.77 (s, 1H), 6.58 (d, J=15.6 Hz, 1H), 6.18 (d, J=15.6 Hz, 1H), 2.77-2.72 (m, 5H), 2.69 (t, J=7.2 Hz, 4H), 2.64-2.58 (m, 1H), 2.08 (s, 3H), 1.90 (quin, J=7.6 Hz, 4H), 1.75-1.70 (m, 3H), 1.62-1.60 (m, 1H), 1.01 (s, 3H); MS (ESI): m/z (%)=404.21 (100%) (M−K)⁺.

Example-137 tert-butyl(E)-(2-(2-(2-(N-((1,2,3,5,6,7-hexahydro-s-indacen-4-yl)carbamoyl)sulfamoyl)vinyl)azetidin-1-yl)ethyl)(methyl)carbamate

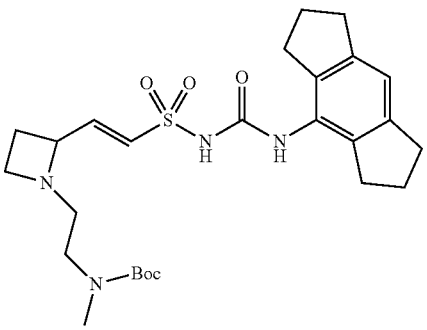 [SMILES: CN(CCN1CCC1/C=C/S(=O)(=O)NC(=O)Nc1c2c(cc3c1CCC3)CCC2)C(=O)OC(C)(C)C]

$^1$H NMR (400 MHz, DMSO-d$_6$): δ=8.03 (s, 1H), 6.94 (m, 1H), 6.85-6.64 (m, 2H), 3.88-3.72 (m, 1H), 2.96-2.88 (m, 1H), 2.80 (t, J=7.2 Hz, 4H), 2.75-2.71 (m, 4H), 2.67 (t, J=7.2 Hz, 4H), 2.61-2.54 (m, 1H), 2.46-2.40 (m, 1H), 2.25-2.19 (m, 1H), 1.99-1.92 (m, 2H), 1.41-1.38 (m, 12H); MS (ESI): m/z (%)=519.26 (90%) (M+H)$^+$, 517.20 (90%) (M−1).

Example-138

(S,E)-2-(1-(cyclohexylmethyl)-2-methylpyrrolidin-2-yl)-N-((1,2,3,5,6,7-hexahydro-s-indacen-4-yl)carbamoyl)ethene-1-sulfonamide

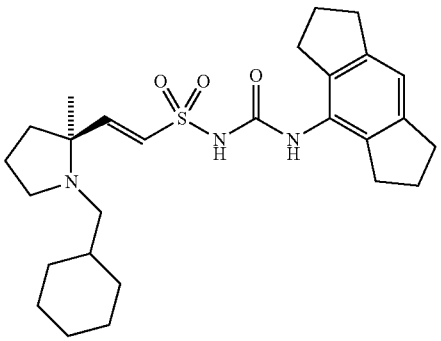 [SMILES: C[C@@]1(/C=C/S(=O)(=O)NC(=O)Nc2c3c(cc4c2CCC4)CCC3)CCCN1CC1CCCCC1]

$^1$H NMR (400 MHz, DMSO-d$_6$): δ=10.36 (brs, 1H), 8.04 (s, 1H), 6.95 (m, 1H), 6.78-6.62 (m, 2H), 2.81 (t, J=7.2 Hz, 4H), 2.68 (t, J=7.2 Hz, 4H), 2.65-2.55 (m, 1H), 2.26-2.02 (m, 2H), 2.00-1.91 (m, 5H), 1.86-1.71 (m, 4H), 1.70-1.50 (m, 5H), 1.43-1.24 (m, 1H), 1.23-1.13 (m, 2H), 1.12-1.00 (m, 4H), 0.86-0.67 (m, 2H); MS (TOF): m/z (%)=486.2891 (100%) (M+H)$^+$, 484.2571 (100%) (M−1).

Example-139

Sodium(R,E)-((1,2,3,5,6,7-hexahydro-s-indacen-4-yl)carbamoyl)((2-(1-(tetrahydro-2H-thiopyran-4-yl)pyrrolidin-2-yl)vinyl)sulfonyl)amide

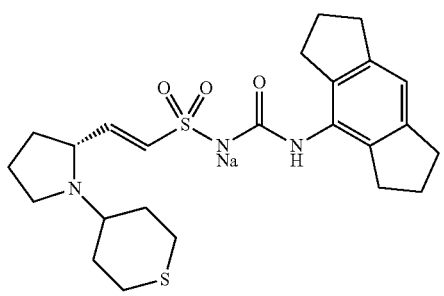

$^1$H NMR (400 MHz, DMSO-d$_6$): δ=7.31 (s, 1H), 6.76 (s, 1H), 6.63 (d, J=15.2 Hz, 1H), 6.06 (dd, J=15.2 Hz, J=7.6 Hz, 1H), 3.43-3.36 (m, 1H), 2.87-2.64 (m, 10H), 2.65-2.42 (m, 5H), 2.03-1.84 (m, 7H), 1.68-1.43 (m, 5H); MS (ESI): m/z (%)=476.25 (100%) (M+H)$^+$, 474.20 (100%) (M−1).

Example-140 sodium(R,E)-((2-(1-cyclohexylpyrrolidin-2-yl)vinyl)sulfonyl)((1,2,3,5,6,7-hexahydro-s-indacen-4-yl)carbamoyl)amide

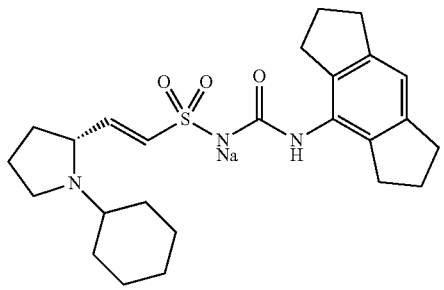

$^1$H NMR (400 MHz, DMSO-d$_6$): δ=7.33 (s, 1H), 6.77 (s, 1H), 6.63 (d, J=15.2 Hz, 1H), 6.09 (dd, J=15.2 Hz, J=7.6 Hz, 1H), 3.34-3.42 (m, 1H), 2.84-2.79 (m, 1H), 2.76 (t, J=7.2 Hz, 4H), 2.70 (t, J=7.2 Hz, 4H), 2.41-2.31 (m, 1H), 1.94-1.80 (m, 5H), 1.75-1.61 (m, 7H), 1.54-1.41 (m, 2H), 1.24-1.07 (m, 5H); MS (TOF): m/z (%)=458.2811 (100%) (M+H)$^+$.

Example-141 sodium(S,E)-((2,6-diisopropylphenyl)carbamoyl)((2-(1,2-dimethylpyrrolidin-2-yl)vinyl)sulfonyl)amide

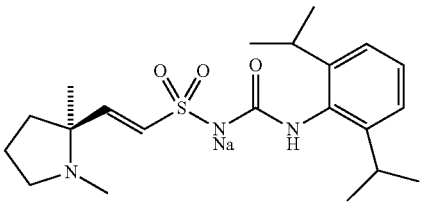

$^1$H NMR (400 MHz, DMSO-d$_6$): δ=7.24 (s, 1H), 7.11 (t, J=8.4 Hz, 1H), 7.04 (d, J=7.6 Hz, 2H), 6.54 (d, J=15.6 Hz, 1H), 6.21 (d, J=16.0 Hz, 1H), 3.23-3.16 (m, 2H), 2.74-2.67

(m, 1H), 2.65-2.59 (m, 1H), 2.08 (s, 3H), 1.75-1.71 (m, 3H), 1.61-1.59 (m, 1H), 1.1 (d, J=6.4 Hz, 12H), 1.0 (s, 3H); MS (ESI): m/z (%)=408.25 (100%) (M−Na)⁺.

Example-142 sodium(R,E)-((1,2,3,5,6,7-hexahydro-s-indacen-4-yl)carbamoyl)(2-(1-methylpyrrolidin-2-yl)vinyl)sulfonyl)amide

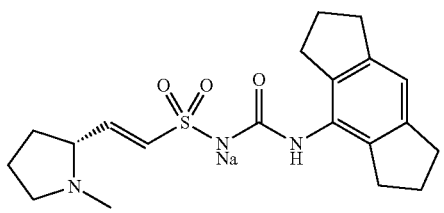

¹H NMR (400 MHz, DMSO-d₆): δ=7.37 (s, 1H), 6.77 (s, 1H), 6.64 (d, J=15.2 Hz, 1H), 6.07 (d, J=15.2 Hz, 1H), 3.0-2.95 (m, 1H), 2.76 (t, J=7.2 Hz, 4H), 2.69 (t, J=7.2 Hz, 4H), 2.59-2.53 (m, 1H), 2.14 (s, 3H), 2.13-2.06 (m, 2H), 1.91 (quin, J=7.2 Hz, 4H), 1.73-1.60 (m, 3H), 1.54-1.49 (m, 1H); MS (ESI): m/z (%)=390.20 (100%) (M−Na)⁺.

Example-143 potassium(R,E)-((1,2,3,5,6,7-hexahydro-s-indacen-4-yl)carbamoyl)((2-(1-methylpyrrolidin-2-yl)vinyl)sulfonyl)amide

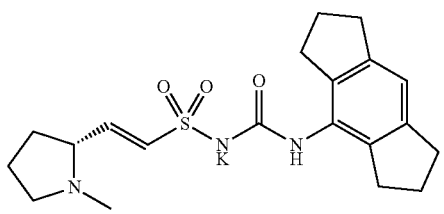

¹H NMR (400 MHz, DMSO-d₆): δ=7.31 (s, 1H), 6.76 (s, 1H), 6.67 (d, J=15.2 Hz, 1H), 6.03-6.01 (m, 1H), 2.97 (bs, 1H), 2.76 (bs, 4H), 2.69 (bs, 4H), 2.14-2.08 (m, 4H), 1.91 (bs, 5H), 1.68 (bs, 3H), 1.49 (bs, 1H); MS (ESI): m/z (%)=390.20 (100%) (M−K)⁺.

Example-144 sodium(S,E)-((2-(1,2-dimethylpyrrolidin-2-yl)vinyl)sulfonyl)((1,2,3,5,6,7-hexahydro-s-indacen-4-yl)carbamoyl)amide

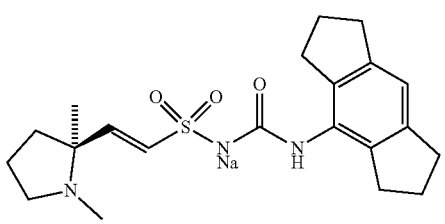

1H NMR (400 MHz, DMSO-d6): δ=7.33 (s, 1H), 6.77 (s, 1H), 6.56 (d, J=15.2 Hz, 1H), 6.16 (d, J=16 Hz, 1H), 2.76 (t, J=7.2 Hz, 4H), 2.69 (t, J=7.2 Hz, 4H), 2.62 (m, 1H), 2.08 (s, 3H), 1.90 (m, 4H), 1.72 (m, 4H), 1.60 (m, 3H), 1.01 (s, 3H); MS (ESI): m/z (%)=404.20 (100%) (M+1).

Example-145 sodium(S,E)-((2-(1-ethylpyrrolidin-2-yl)vinyl)sulfonyl)((1,2,3,5,6,7-hexahydro-s-indacen-4-yl)carbamoyl)amide

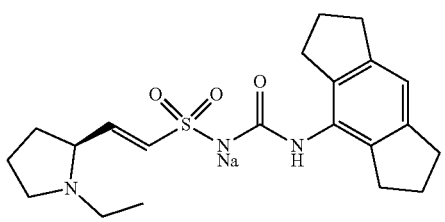

¹H NMR (400 MHz, DMSO-d₆): δ=7.36 (s, 1H), 6.77 (s, 1H), 6.61 (d, J=15.2 Hz, 1H); 6.05 (dd, J=8.0 Hz, J=15.2 Hz, 1H); 3.10-3.05 (m, 1H), 2.78-2.65 (m, 10H), 2.12-1.85 (m, 7H), 1.71-1.66 (m, 2H), 1.49-1.44 (m, 1H), 0.98 (t, J=7.2 Hz, 3H); MS (ESI): m/z (%)=426.20 (50%) (M+H)⁺.

Example-146

(S,E)-N-((1,2,3,5,6,7-hexahydro-s-indacen-4-yl)carbamoyl)-2-(1-(2-hydroxyethyl)pyrrolidin-2-yl)ethene-1-sulfonamide

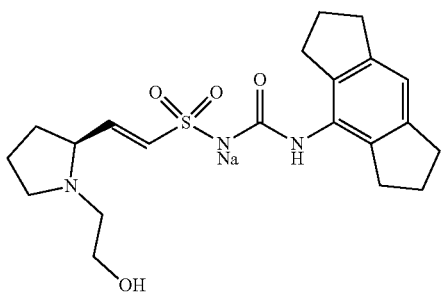

1H NMR (400 MHz, DMSO-d6): δ=7.90 (s, 1H), 6.90 (s, 1H), 6.84 (d, J=15.8 Hz, 1H), 6.51 (d, J=14.8 Hz, 1H), 4.57 (s, 1H), 3.57 (d, J=8.8 Hz, 2H), 3.17 (s, 2H), 2.80 (t, J=7.2 Hz, 1H), 2.72 (t, J=7.2 Hz, 4H), 2.33 (d, J=1.6 Hz, 2H), 1.96 (m, 4H), 1.91 (s, 2H), 1.72 (m, 2H), 1.56 (m, 1H); MS (ESI): m/z (%)=420.23 (100%) (M+1).

Example-147 tert-butyl(E)-2-(2-(N-((1,2,3,5,6,7-hexahydro-s-indacen-4-yl)carbamoyl)sulfamoyl)vinyl)-2-methyl-azetidine-1-carboxylate

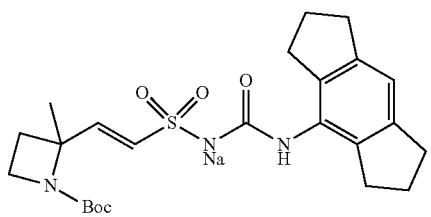

Example 147 was prepared as per the procedure described for synthesis of Intermediate-3a using Intermediate-12, together with conventional techniques known to those skilled in the art of organic synthesis.

$^1$H NMR (400 MHz, DMSO-d$_6$): δ=10.47 (br s, 1H), 8.12 (s, 1H), 6.96 (s, 1H), 6.92 (d, J=15.2 Hz, 1H), 6.70 (d, J=15.2 Hz, 1H), 3.82-3.61 (m, 2H), 2.81 (t, J=7.2 Hz, 4H), 2.68 (t, J=6.8 Hz, 4H), 2.20-2.08 (m, 2H), 2.00-1.93 (m, 4H), 1.52 (s, 3H), 1.38-1.33 (m, 9H); MS (TOF): m/z (%)=498.2359 (90%) (M+Na)$^+$, 474.2308 (100%) (M-1).

Example-148

(E)-2-(1,2-dimethylazetidin-2-yl)-N-((1,2,3,50,6,7-hexahydro-s-indacen-4-yl)carbamoyl)ethene-1-sulfonamide

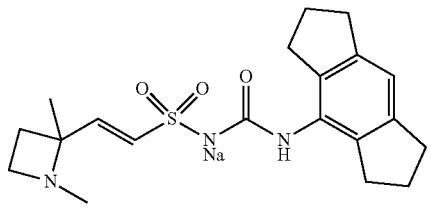

$^1$H NMR (400 MHz, DMSO-d$_6$): δ=7.91 (s, 1H), 6.91 (s, 1H), 6.79 (d, J=14.8 Hz, 1H), 6.72 (d, J=15.2 Hz, 1H), 3.33-3.16 (m, 2H), 2.79 (t, J=7.2 Hz, 4H), 2.68 (t, J=7.2 Hz, 4H), 2.22 (s, 3H), 2.18-2.11 (m, 1H), 2.00-1.91 (m, 5H), 1.34 (s, 3H); MS (TOF): m/z (%)=390.2279 (70%) (M+H)$^+$, 388.2130 (100%) (M-1).

Example-149 tert-butyl(S,E)-2-ethyl-2-(2-(N-((1,2,3,5,6,7-hexahydro-s-indacen-4-yl)carbamoyl)sulfamoyl)vinyl)pyrrolidine-1-carboxylate

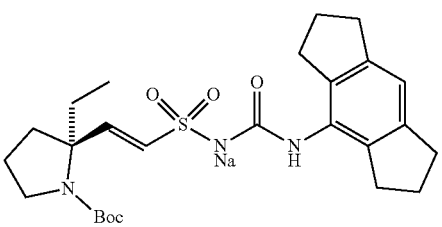

$^1$H NMR (400 MHz, DMSO-d$_6$): δ=10.38 (s, 1H), 8.0 (d, J=4.4 Hz, 1H), 6.99 (s, 1H), 6.89 (d, J=15.2 Hz, 1H), 6.50 (d, J=15.2 Hz, 1H), 3.50 (m, 1H), 3.25 (m, 1H), 2.81 (t, J=7.2 Hz, 4H), 2.65 (t, J=7.2 Hz, 5H), 1.95 (m, 4H), 1.77 (s, 3H), 1.80 (m, 4H), 1.58 (m, 1H), 1.36 (d, J=10 Hz, 9H), 0.81 (m, 3H); MS (ESI): m/z (%)=502.23 (100%) (M-1).

Example-150 tert-butyl(S,E)-2-(2-(N-((1,2,3,6,7,8-hexahydro-as-indacen-4-yl)carbamoyl)sulfamoyl)vinyl)-2-methylpyrrolidine-1-carboxylate

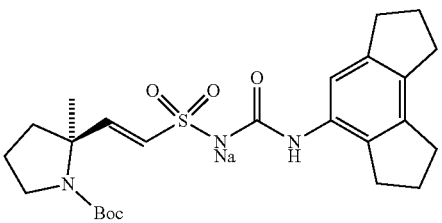

$^1$H NMR (400 MHz, DMSO-d$_6$): δ=7.95 (s, 1H), 7.42 (d, J=15.2 Hz, 1H), 6.79 (d, J=7.68 Hz, 1H), 6.55 (d, J=15.2 Hz, 1H), 3.39 (m, 2H), 2.80 (q, J=7.6 Hz, 4H), 2.70 (t, J=7.2 Hz, 5H), 2.01 (m, 6H), 1.82 (m, 2H), 1.68 (m, 1H), 1.46 (d, J=10 Hz, 3H), 1.38 (s, 3H), 1.32 (s, 7H); MS (ESI): m/z (%)=488.24 (100%) (M-1).

Example-151

(S,E)-2-(2-ethylpyrrolidin-2-yl)-N-((1,2,3,5,6,7-hexahydro-s-indacen-4-yl)carbamoyl)ethene-1-sulfonamide 2,2,2-trifluoroacetate

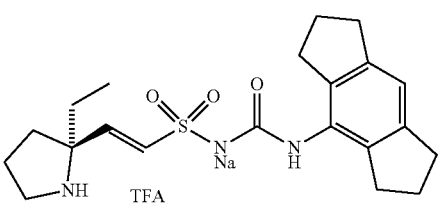

¹H NMR (400 MHz, DMSO-d₆): δ=9.19 (s, 1H), 90.6 (s, 1H), 8.39 (s, 1H), 7.56 (s, 1H), 7.11 (s, 1H), 6.97 (s, 1H), 6.84 (d, J=15.6 Hz, 1H), 3.32 (s, 1H), 3.17 (s, 1H), 2.81 (t, J=6.8 Hz, 4H), 2.65 (t, J=7.2 Hz, 4H), 2.24 (m, 1H), 1.96 (m, 6H), 1.83 (m, 4H), 0.85 (q, J=6.8 Hz, 3H); MS (ESI): m/z (%)=404.3 (100%) (M+1).

Example-152

(S,E)-N-((1,2,3,6,7,8-hexahydro-as-indacen-4-yl)carbamoyl)-2-(2-methylpyrrolidin-2-yl)ethene-1-sulfonamide 2,2,2-trifluoroacetate

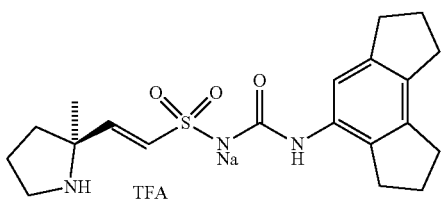

¹H NMR (400 MHz, DMSO-d₆): δ=7.39 (s, 1H), 7.11 (d, J=15.6 Hz, 1H), 7.02 (d, J=15.6 Hz, 1H), 2.79 (q, J=7.6 Hz, 5H), 2.71 (t, J=7.2 Hz, 4H), 2.01 (m, 9H), 1.47 (q, J=7.2 Hz, 3H), 1.04 (d, J=6.0 Hz, 2H); MS (ESI): m/z (%)=390.24 (100%) (M+1).

Example-153

(S,E)-2-(1,2-dimethylpyrrolidin-2-yl)-N-((1,2,3,6,7,8-hexahydro-as-indacen-4-yl)carbamoyl)ethene-1-sulfonamide

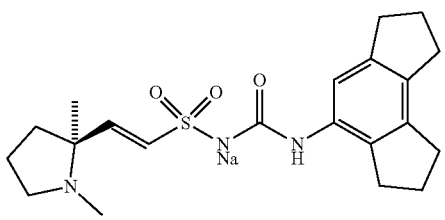

1H NMR (400 MHz, DMSO-d6): δ=7.88 (s, 1H), 7.43 (s, 1H), 6.72 (d, J=15.2 Hz, 1H), 6.62 (d, J=15.2 Hz, 1H), 3.09 (q, J=7.2 Hz, 4H), 2.75 (m, 4H), 2.60 (t, J=6.8 Hz, 4H), 2.21 (s, 3H), 1.95 (m, 4H), 1.78 (t, J=10 Hz, 4H), 1.17 (m, 8H); MS (ESI): m/z (%)=404.30 (100%) (M+1).

Example-154 tert-butyl(R,E)-2-(2-(N-((1,2,3,6,7,8-hexahydro-as-indacen-4-yl)carbamoyl)sulfamoyl)vinyl)-2-methylpyrrolidine-1-carboxylate

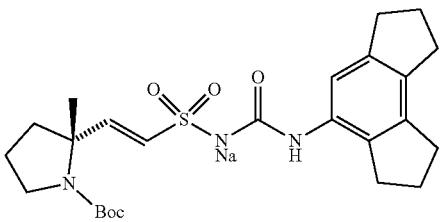

¹H NMR (400 MHz, DMSO-d₆): δ=10.85 (s, 1H), 7.98 (s, 1H), 7.43 (d, J=9.2 Hz, 1H), 6.89 (q, J=15.6 Hz, 1H), 6.58 (d, J=15.2 Hz, 1H), 3.42-3.36 (m, 2H), 2.81-2.74 (m, 4H), 2.70 (t, J=7.2 Hz, 4H), 2.21-1.94 (m, 5H), 1.88-1.75 (m, 2H), 1.72-1.66 (m, 1H), 1.48 (d, J=9.6 Hz, 3H), 1.32 (s, 9H); MS (ESI): m/z (%)=512.21 (40%) (M+Na)⁺; 502.28 (100%) (M−H)⁻.

Example-155

(R,E)-N-((1,2,3,6,7,8-hexahydro-as-indacen-4-yl)carbamoyl)-2-(2-methylpyrrolidin-2-yl)ethene-1-sulfonamide 2,2,2-trifluoroacetate

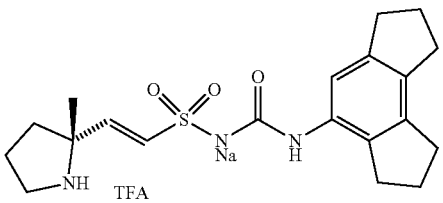

¹H NMR (400 MHz, DMSO-d₆): δ=9.09 (bs, 2H), 8.21 (s, 1H), 7.39 (s, 1H), 7.13 (d, J=15.6 Hz, 1H), 7.03 (d, J=15.2 Hz, 1H), 2.81-2.64 (m, 10H), 2.10-1.89 (m, 9H), 1.48 (s, 3H); MS (ESI): m/z (%)=390.18 (100%) (M-TFA)⁺.

Example-156

(R,E)-2-(1,2-dimethylpyrrolidin-2-yl)-N-((1,2,3,6,7,8-hexahydro-as-indacen-4-yl)carbamoyl)ethene-1-sulfonamide

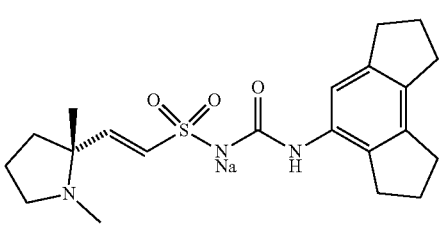

¹H NMR (400 MHz, DMSO-d₆): δ=7.86 (s, 1H), 7.44 (s, 1H), 6.75 (d, J=15.6 Hz, 1H), 6.63 (d, J=15.2 Hz, 1H), 2.90-2.88 (m, 4H), 2.80 (q, J=7.2 Hz, 5H), 2.20 (s, 3H), 2.04 (quin, J=7.2 Hz, 4H), 1.84-1.72 (m, 4H), 1.13 (s, 3H); MS (ESI): m/z (%)=404.30 (100%) (M+H)⁺; 402.50 (100%) (M−1)⁻.

Example-157 tert-butyl(R,E)-2-(3-(N-((1,2,3,5,6,7-hexahydro-s-indacen-4-yl)carbamoyl)sulfamoyl)allyl)-2-methylpyrrolidine-1-carboxylate

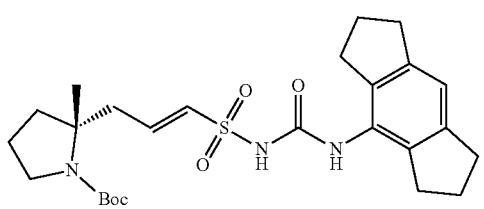 [SMILES: CC(C)(C)OC(=O)N1CCC[C@]1(C)C/C=C/S(=O)(=O)NC(=O)Nc1c2c(cc3c1CCC3)CCC2]

¹H NMR (400 MHz, DMSO-d₆): δ=10.38 (s, 1H), 8.07 (d, J=7.2 Hz, 1H), 6.95 (s, 1H), 6.81 (q, J=15.2 Hz, 1H), 6.64 (dd, J; =8.0 Hz, J₂=15.2 Hz, 1H), 3.19-3.17 (m, 1H), 2.91-2.86 (m, 1H), 2.81 (t, J=7.2 Hz, 4H), 2.67 (t, J=7.2 Hz, 5H), 2.63-2.58 (m, 1H), 1.97 (quin, J=7.2 Hz, 4H), 1.88-1.83 (m, 1H), 1.70-1.62 (m, 3H), 1.41 (d, J=6.8 Hz, 9H), 1.30 (s, 3H); MS (ESI): m/z (%)=526.28 (50%) (M+Na)⁺; 502.28 (100%) (M−H)⁻.

Example-158 tert-butyl(R,E)-(2-(2-(3-(N-((1,2,3,5,6,7-hexahydro-s-indacen-4-yl)carbamoyl)sulfamoyl)allyl)-2-methylpyrrolidin-1-yl)ethylxmethyl)carbamate

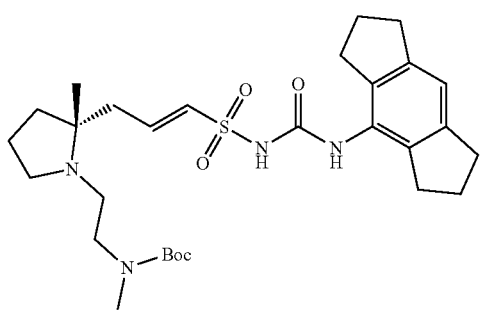 [SMILES: CN(CCN1CCC[C@]1(C)C/C=C/S(=O)(=O)NC(=O)Nc1c2c(cc3c1CCC3)CCC2)C(=O)OC(C)(C)C]

¹H NMR (400 MHz, DMSO-d₆): δ=10.37 (bs, 1H), 8.03 (s, 1H), 6.95 (s, 1H), 6.74 (d, J=8.0 Hz, 2H), 3.12 (q, J=7.2 Hz, 2H), 2.90 (bs, 1H), 2.80 (t, J=7.2 Hz, 6H), 2.67 (t, J=6.8 Hz, 5H), 2.29-2.26 (m, 2H), 1.96 (quin, J=7.2 Hz, 4H), 1.68-1.67 (m, 4H), 1.38 (s, 12H), 1.28 (s, 3H); MS (ESI): m/z (%)=560.31 (100%) (M+H)⁺; 559.29 (100%) (M−1)⁻.

Example-159

(R,E)-3-(1,2-dimethylpyrrolidin-2-yl)-N-((1,2,3,5,6,7-hexahydro-s-indacen-4-yl)carbamoyl)prop-1-ene-1-sulfonamide

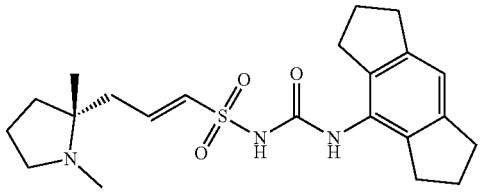 [SMILES: CN1CCC[C@]1(C)C/C=C/S(=O)(=O)NC(=O)Nc1c2c(cc3c1CCC3)CCC2]

¹H NMR (400 MHz, DMSO-d₆): δ=8.04 (s, 1H), 6.90 (s, 1H), 6.75-6.72 (m, 1H), 6.62-6.54 (m, 1H), 3.17-3.00 (m, 1H), 2.79 (t, J=6.8 Hz, 5H), 2.69 (bs, 4H), 2.36 (s, 5H), 1.95 (t, J=7.2 Hz, 4H), 1.81-1.74 (m, 3H), 1.58 (bs, 1H), 1.04 (s, 3H); MS (ESI): m/z (%)=418.21 (100%) (M+H)⁺.

Example-160 tert-butyl(S,E)-(3-(2-(2-(N-((1,2,3,5,6,7-hexahydro-s-indacen-4-yl)carbamoyl)sulfamoyl)vinyl)pyrrolidin-1-yl)propyl)(methyl)carbamate

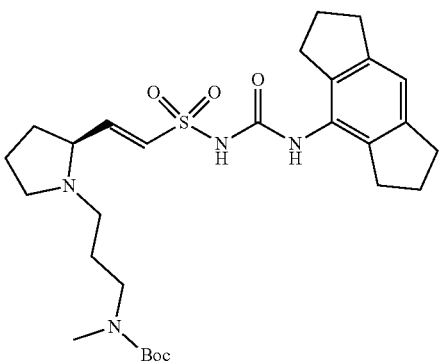 [SMILES: CN(CCCN1CCC[C@H]1/C=C/S(=O)(=O)NC(=O)Nc1c2c(cc3c1CCC3)CCC2)C(=O)OC(C)(C)C]

¹H NMR (400 MHz, DMSO-d₆): δ=8.05 (s, 1H), 6.94 (s, 1H), 6.82 (d, J=15.2 Hz, 1H), 6.62-6.57 (m, 1H), 3.26-3.22 (m, 1H), 3.30-2.94 (m, 1H), 2.82-2.65 (m, 13H), 2.20-2.18 (m, 2H), 2.03-1.92 (m, 5H), 1.77-1.71 (m, 3H), 1.59-1.48 (m, 3H), 1.40-1.37 (m, 9H); MS (ESI): m/z (%)=547.5 (100%) (M+H)⁺.

Example-161 tert-butyl (E)-(3-(2-(2-(N-((1,2,3,5,6,7-hexahydro-s-indacen-4-yl)carbamoyl)sulfamoyl)vinyl)-2-methyl-azetidin-1-yl)propyl)(methyl)carbamate

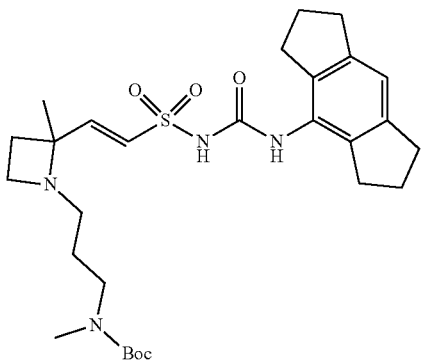 [SMILES: CN(CCCN1CCC1(C)/C=C/S(=O)(=O)NC(=O)Nc1c2c(cc3c1CCC3)CCC2)C(=O)OC(C)(C)C]

$^1$H NMR (400 MHz, DMSO-d$_6$): δ=8.04 (s, 1H), 6.94 (s, 1H), 6.83 (d, J=15.2 Hz, 1H), 6.77 (d, J=15.2 Hz, 1H), 3.29-3.27 (m, 2H), 2.80 (t, J=7.2 Hz, 4H), 2.75-2.72 (m, 1H), 2.68 (t, J=7.2 Hz, 4H), 2.50 (s, 3H), 2.37-2.33 (m, 2H), 2.08-2.06 (m, 1H), 2.00-1.92 (m, 4H), 1.58-1.49 (m, 2H), 1.39-1.37 (m, 9H), 1.32 (s, 3H), 1.28-1.22 (m, 1H); MS (ESI): m/z (%)=547.5 (100%) (M+H)$^+$, 545.7 (100%) (M−1).

Example-162 tert-butyl(E)-(2-(2-(2-(N-((1,2,3,5,6,7-hexahydro-s-indacen-4-yl)carbamoyl)sulfamoyl)vinyl)-2-methyl-azetidin-1-yl)ethyl)(methyl)carbamate

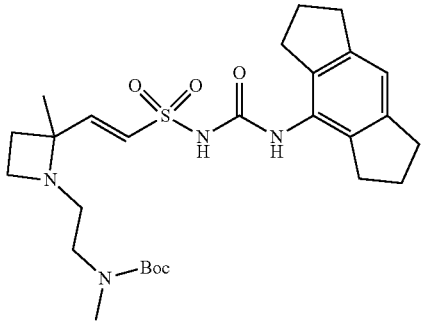 [SMILES: CN(CCN1CCC1(C)/C=C/S(=O)(=O)NC(=O)Nc1c2c(cc3c1CCC3)CCC2)C(=O)OC(C)(C)C]

$^1$H NMR (400 MHz, DMSO-d$_6$): δ=8.05 (s, 1H), 6.95 (s, 1H), 6.83 (d, J=14.8 Hz, 1H), 6.75-6.68 (m, 1H), 3.32-3.23 (m, 1H), 3.09-3.02 (m, 1H), 2.80 (t, J=7.2 Hz, 4H), 2.75-2.71 (m, 2H), 2.67 (t, J=7.2 Hz, 4H), 2.56-2.52 (m, 1H), 2.51 (s, 3H), 2.48-2.43 (m, 1H), 2.05-1.89 (m, 6H), 1.39-1.38 (m, 9H), 1.32 (s, 3H); MS (TOF): m/z (%)=533.3222 (40%) (M+H)$^+$, 531.3039 (100%) (M−1).

Example-163

(E)-N-((1,2,3,5,6,7-hexahydro-s-indacen-4-yl)carbamoyl)-2-(2-methyl-1-(2-(methylthio)ethyl)azetidin-2-yl)ethene-1-sulfonamide

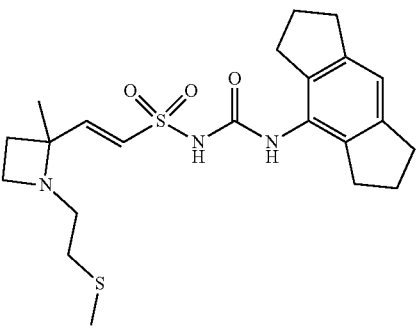 [SMILES: CSCCN1CCC1(C)/C=C/S(=O)(=O)NC(=O)Nc1c2c(cc3c1CCC3)CCC2]

$^1$H NMR (400 MHz, DMSO-d$_6$): δ=10.36 (brs, 1H), 8.07 (s, 1H), 6.95 (s, 1H), 6.87 (d, J=14.8 Hz, 1H), 6.83 (d, J=14.8 Hz, 1H), 3.40-3.22 (m, 2H), 3.18-3.04 (m, 1H), 2.81 (t, J=7.2 Hz, 4H), 2.68 (t, J=7.2 Hz, 4H), 2.59-2.53 (m, 2H), 2.41-2.38 (m, 2H), 2.08-1.88 (m, 8H), 1.32 (s, 3H); MS (TOF): m/z (%)=450.1660 (100%) (M+H)$^+$.

Example-164

(E)-N-((1,2,3,5,6,7-hexahydro-s-indacen-4-yl)carbamoyl)-2-(2-methyl-1-(oxetan-3-yl)azetidin-2-yl)ethene-1-sulfonamide

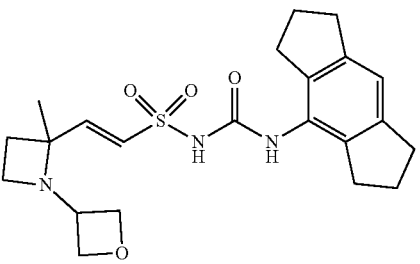 [SMILES: CC1(/C=C/S(=O)(=O)NC(=O)Nc2c3c(cc4c2CCC4)CCC3)CCN1C1COC1]

$^1$H NMR (400 MHz, DMSO-d$_6$): δ=10.4 (brs, 1H), 8.13 (s, 1H), 6.96 (s, 1H), 6.84 (d, J=15.2 Hz, 1H), 6.80 (d, J=15.2 Hz, 1H), 4.56 (t, J=6.0 Hz, 1H), 4.48-4.44 (m, 2H), 4.31 (t, J=6.4 Hz, 1H), 3.93-3.87 (m, 1H), 3.38-3.28 (m, 3H), 2.81 (t, J=7.2 Hz, 4H), 2.68 (t, J=7.2 Hz, 4H), 2.12-2.06 (m, 1H), 2.01-1.97 (m, 5H), 1.24 (s, 3H); MS (TOF): m/z (%)=432.1744 (80%) (M+H)$^+$.

Example-165 tert-butyl(S)-2-(((S)-2-((E)-2-(N-((1,2,3,5,6,7-hexahydro-s-indacen-4-yl)carbamoyl)sulfamoyl)vinyl)-2-methylazetidin-1-yl)methyl)-2-methylpyrrolidine-1-carboxylate

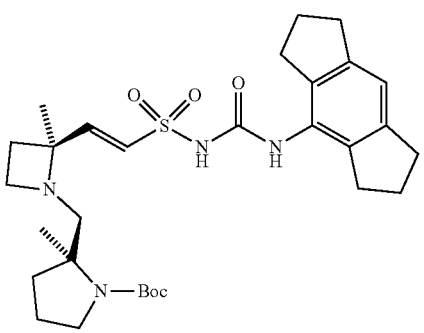

¹H NMR (400 MHz, DMSO-d₆): δ=10.4 (brs, 1H), 8.10 (s, 1H), 6.98-6.93 (m, 2H), 6.74 (dd, J=15.6 Hz, J=5.2 Hz, 1H), 3.30-3.27 (m, 2H), 3.20-3.16 (m, 2H), 2.80 (t, J=7.2 Hz, 4H), 2.69 (t, J=6.8 Hz, 4H), 2.04-1.91 (m, 7H), 1.75-1.46 (m, 3H), 1.39-1.37 (m, 9H), 1.27 (s, 3H), 1.17 (s, 3H); MS (TOF): m/z (%)=573.2813 (100%) (M+H)⁺;

Example-166 tert-butyl(S)-2-(((R)-2-((E)-2-(N-((1,2,3,5,6,7-hexahydro-s-indacen-4-yl)carbamoyl)sulfamoyl)vinyl)-2-methylazetidin-1-yl)methyl)-2-methylpyrrolidine-1-carboxylate

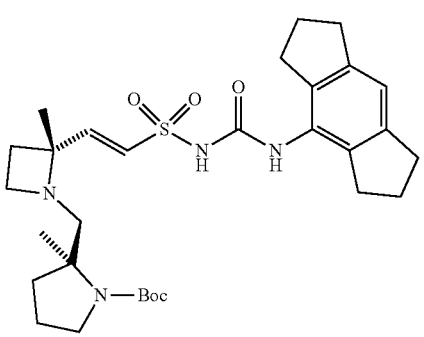

¹H NMR (400 MHz, DMSO-d₆): δ=10.41 (brs, 1H), 8.10 (s, 1H), 6.96 (s, 1H), 6.77-6.73 (m, 2H), 3.41-3.34 (m, 1H), 3.26-3.15 (m, 3H), 2.81 (t, J=7.2 Hz, 4H), 2.57 (t, J=7.2 Hz, 4H), 2.16-1.89 (m, 7H), 1.79-1.47 (m, 3H), 1.40-1.37 (m, 9H), 1.30-1.28 (m, 3H), 1.21-1.20 (m, 3H); MS (TOF): m/z (%)=573.2814 (80%) (M+H)⁺;

Example-167

(R,E)-N-((1,2,3,5,6,7-hexahydro-s-indacen-4-yl)carbamoyl)-2-(1-(2-sulfamoylethyl)pyrrolidin-2-yl)ethene-1-sulfonamide

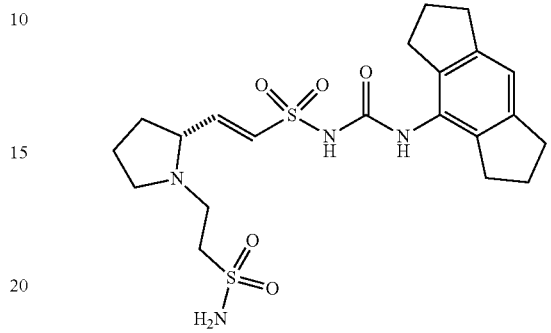

¹H NMR (400 MHz, DMSO-d₆): δ=10.42 (br s, 1H), 8.09 (s, 1H), 6.95 (s, 1H), 6.87 (d, J=14.8 Hz, 1H), 6.75 (s, 2H), 6.66 (dd, J=14.8 Hz, J=7.2 Hz, 1H), 3.23-3.07 (m, 4H), 3.01-2.94 (m, 1H), 2.80 (t, J=7.2 Hz, 4H), 2.67 (t, J=7.2 Hz, 4H), 2.63-2.56 (m, 1H), 2.33-2.27 (m, 1H), 2.02-1.93 (m, 5H), 1.73-1.70 (m, 2H), 1.55-1.50 (m, 1H); MS (TOF): m/z (%)=483.1490 (80%) (M+H)⁺.

Example-168

(S,E)-2-(2-ethyl-1-methylpyrrolidin-2-yl)-N-((1,2,3,5,6,7-hexahydro-s-indacen-4-yl)carbamoyl)ethene-1-sulfonamide

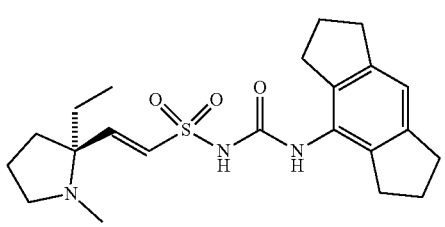 [SMILES: CC[C@@]1(/C=C/S(=O)(=O)NC(=O)Nc2c3c(cc4c2CCC4)CCC3)CCCN1C]

1H NMR (400 MHz, DMSO-d6): δ=8.01 (s, 1H), 6.93 (s, 1H), 6.71 (d, J=15.2 Hz, 1H), 6.58 (d, J=15.6 Hz, 1H), 2.99 (m, 1H), 2.80 (t, J=7.2 Hz, 4H), 2.66 (t, J=7.2 Hz, 4H), 2.57 (m, 1H), 2.24 (s, 3H), 1.95 (m, 4H), 1.85 (m, 1H), 1.72 (m, 4H), 1.45 (m, 1H), 0.8 (t, J=7.2 Hz, 3H); MS (ESI): m/z (%)=418.19 (100%) (M+1);

Example-169

(R,E)-2-(1-(but-2-yn-1-yl)pyrrolidin-2-yl)-N-((1,2,3,5,6,7-hexahydro-s-indacen-4-yl)carbamoyl)ethene-1-sulfonamide

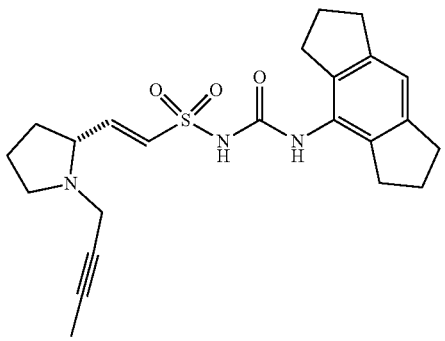

$^1$H NMR (400 MHz, DMSO-$d_6$): δ=8.84 (s, 1H), 7.03 (d, J=15.6 Hz, 1H), 6.91 (s, 1H), 6.35-6.23 (m, 1H), 4.31-4.03 (m, 3H), 3.26-3.07 (m, 2H), 2.82-2.67 (m, 8H), 2.20-2.05 (m, 1H), 1.97-1.83 (m, 6H), 1.74-1.61 (m, 4H); MS (TOF): m/z (%)=428.1884 (100%) (M+H)$^+$.

Biological Activity:

In-Vitro Assay:

THP1 monocytes were differentiated with PMA (100 ng/mL) and incubated at 37 deg C. for 20 hrs in presence of 5% CO2. 2×10$^5$ differentiated cells were plated per well of 96 well tissue culture plates. The cells were primed using 500 ng/mL Lipopolysaccharide and incubating for 4 h under the same condition. The cells were then treated with various concentrations of the compounds for 30 min followed by treatment with 5 mM ATP for 1 hr. The supernatants were collected and analyzed by IL-1b (Mabtech Cat #3415-1H-20) or TNF-α (Mabtech; Cat #3510-1H-20) detection kit. The data were analyzed using GraphPad Prism V7.0. Dose Response Curve (DRC) was constructed to determine the IC$_{50}$ value by fitting percentage cell survival data to the GraphPad Prism using nonlinear regression analysis. The invitro IL-1β inhibitory activity (IC$_{50}$) for representative compounds are listed in Table 1.

TABLE 1

| Compound | IC$_{50}$ (nM) |
| --- | --- |
| Example 4 | 7.4 |
| Example 8 | 10.7 |
| Example 10 | 64 |
| Example 13 | 9 |
| Example 14 | 17 |
| Example 21 | 2.4 |
| Example 23 | 14 |
| Example 56 | 8.8 |
| Example 63 | 8 |
| Example 71 | 87 |
| Example 84 | 8.5 |
| Example 90 | 16 |
| Example 91 | 2.9 |
| Example 100 | 70 |
| Example 105 | 61 |
| Example 111 | 4.3 |
| Example 125 | 16.4 |
| Example 127 | 5.6 |
| Example 129 | 5.9 |
| Example 131 | 16 |

TABLE 1-continued

| Compound | IC$_{50}$ (nM) |
| --- | --- |
| Example 139 | 21 |
| Example 144 | 8.6 |
| Example 147 | 11 |
| Example 149 | 11 |
| Example 153 | 32 |

In-Vivo Efficacy Studies:

Demonstration of in vivo efficacy of test compounds in rats mice, oral routes of administration.

Animals

All the animal experiments were carried out in female rats and mice, bred in-house. Animals were housed in groups of 6 animals per cage, for a week, in order to habituate them to vivarium conditions (25 f 4° C., 60-65% relative humidity, 12:12 h light:dark cycle, with lights on at 7.30 am). All the animal experiments were carried out according to the internationally valid guidelines following approval by the 'Zydus Research Center animal ethical committee'.

In-Vivo LPS and ATP Induced IL-1β Assay:

Female C57 mice (6-8 weeks) received intraperitoneal injection of 50 µg/mouse of lipopolysaccharide (LPS) in PBS. Animals were treated immediately with the test compounds or the vehicle. After 2 h of LPS injection, animals were administered with ATP at 12.5 mg/mouse dissolved in PBS via intraperitoneal route. After 30 minutes of ATP injection, serum was collected for IL-1β estimation by ELISA.

The novel compounds of the present invention can be formulated into suitable pharmaceutically acceptable compositions by combining with suitable excipients by techniques and processes and concentrations as are well known.

Representative data of some of the test compounds are listed in Table-2:

TABLE 2

| Compounds (Dose 10 mpk, po) | % IL-1β inhibition in LPS + ATP challenged C57 mice |
| --- | --- |
| Example 4 | 90% |
| Example 5 | 70% |
| Example 22 | 83% |
| Example 40 | 86% |
| Example 55 | 82.5% |
| Example 69 | 84% |
| Example 73 | 80% |
| Example 77 | 47% |
| Example 101 | 82% |
| Example 102 | 74% |

The compounds of formula (I) or pharmaceutical compositions containing them are useful as a medicament for the inhibition of NLRP3 activity and suitable for humans and other warm blooded animals, and may be administered either by oral, topical or parenteral administration.

Thus, a pharmaceutical composition comprising the compounds of the present invention may comprise a suitable binder, suitable bulking agent &/or diluent and any other suitable agents as may be necessary. Optionally, the pharmaceutical composition may be suitably coated with suitable coating agents.

The compounds of the present invention (I) are NLRP3 inhibitors and are useful in the treatment of disease states mediated by NLRP3, preferably diseases or conditions in which interleukin 1 β activity is implicated and related disorders.

The quantity of active component, that is, the compounds of Formula (I) according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

The compounds of the present invention, formula (I), may be used alone or in any combination with one or more other therapeutic agents which a skilled medical practitioner can easily identify. Such other therapeutic agent may be selected depending on the type of disease being treated, the severity, other medications being taken by the patients etc. Thus for example, for treatment of rheumatoid arthritis, one or more DMARDs may be used in combination with the compounds of the present invention.

In one of the embodiments compound of formula (I) of the present invention may be used in combination with one or more suitable pharmaceutically active agents selected from following therapeutic agents in any combination. Inhibitors of interleukin-1β (e.g. rilonacept, canakinumab, and anakinra); immune-suppressants (e.g., Methotrexate, mercaptopurine, cyclophosphamide), metabolic disorders drugs, glucocorticoids, non-steroidal anti-inflammatory drugs, Cox-2 specific inhibitors, TNF-α binding proteins (eg., Infliximab, etanercept), interferon-13, interferon, interleukin-2, antihistamines, beta-agonist, BTK inhibitors, anti-colinergics, anti-cancer agents or their suitable pharmaceutically acceptable salts. Further examples for use in combination with Non-Alcoholic Steato-Hepatitis (NASH) and fibrosis drugs, anticancer antibiotics, hormones, Aromatase inhibitors, antibodies, cytokines, vaccines, drug conjugates, inhibitors of mitogen-activated protein kinase signaling (ex: BAY 43-9006), Syk inhibitors, mTOR inhibitors, antibodies (Rituxan), and BCR/ABL antagonist.

While the present invention has been described in terms of its specific embodiments, certain modifications and equivalents will be apparent to those skilled in the art and are intended to be included within the scope of the present invention.

We claim:

1. A compound having the structure of general formula (I)

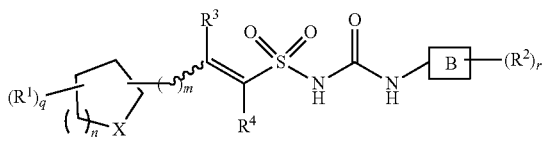

Formula (I)

or a tautomeric form, a stereoisomer, an enantiomer, or a pharmaceutically acceptable salt, thereof, wherein, $R^1$ at each occurrence is independently selected from hydrogen, halogen, haloalkyl, cyano, and optionally substituted groups selected from $(C_1-C_6)$alkyl, $(C_1-C_6)$haloalkyl, $(C_2-C_6)$alkenyl, $(C_1-C_6)$alkoxy, $(C_3-C_7)$cycloalkyl, $NH_2$, $NH(C_1-C_6)$alkyl, $N(C_3-C_7)$cycloalkyl, $N(C_1-C_6$ alkyl$)_2$, aryl, heteroaryl, heterocyclyl, benzyl, thiol, mercapto alkyl, $SO_2(C_1-C_6)$alkyl, $(C_1-C_6)$thioalkoxy, and amide;

X is N—$R^5$, O, S, or $SO_2$;

$R^5$ at each occurrence is independently selected from hydrogen, halogen, haloalkyl, cyano, and optionally substituted groups selected from $(C_1-C_6)$alkyl, $(C_1-C_6)$haloalkyl, $(C_2-C_6)$alkenyl, $(C_2-C_6)$alkynyl, $(C_1-C_6)$alkoxy, $(C_3-C_7)$cycloalkyl, $(C_1-C_6)$alkylSO$_2(C_1-C_6)$alkyl, $(C_1-C_6)$alkylN$(C_1-C_6)$alkyl, $(C_1-C_6)$alkylN$(C_3-C_7)$cycloalkyl, aryl, heteroaryl, heterocyclyl, benzyl, tert-butyloxycarbonyl, thiol, mercapto alkyl, $SO_2(C_1-C_6)$alkyl, $SO_2(C_3-C_7)$cycloalkyl, $SO_2$-aryl, $SO_2$-heterocyclyl, $(C_1-C_6)$thioalkyl, $(C_1-C_6)$thioalkoxy, $(C_1-C_6)$alkylSO$_2$NH$_2$, —CONH$_2$, —CO(C$_1$-C$_6$)alkyl, —CO(C$_1$-C$_6$)haloalkyl, —CO-aryl, —CO-heteroaryl, —CO-heterocyclyl, 4- to 7-membered heterocyclic ring, 7- to 14-membered bicyclic heterocyclic ring system, and bridged or spiro ring system having optionally one or more than one heteroatoms;

m and n is independently selected from integer 0-3;

q and r is independently selected from integer 1-4;

$R^2$ at each occurrence is independently selected from hydrogen, halogen, cyano, and optionally substituted groups selected from $(C_1-C_6)$alkyl, $(C_2-C_6)$alkenyl, $(C_1-C_6)$alkoxy, $(C_3-C_7)$cycloalkyl, benzyl, aryl, heteroaryl, heterocyclyl, thiol, thioalkyl, thio-alkoxy, $SO_2(C_1-C_6)$alkyl, $SO(C_1-C_6)$alkyl, and bridged or spiro ring system having optionally one or more than one heteroatoms;

each of $R^3$ and $R^4$ at each occurrence is independently selected from hydrogen, halogen, haloalkyl, cyano, nitro, amide, sulphonamide, acyl, hydroxyl, and optionally substituted groups selected from $(C_1-C_6)$alkyl, $(C_1-C_6)$haloalkyl, $(C_3-C_6)$cycloalkyl, $(C_1-C_6)$alkoxy, $SO_2(C_1-C_6)$alkyl, thiol, mercapto alkyl, benzyl, aryl, heteroaryl, and heterocyclyl; alternatively $R^3$ and $R^4$ forms a bond;

'B' is selected from the following ring systems

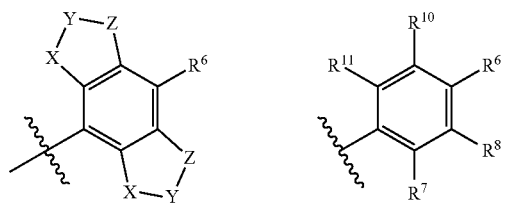

wherein X, Y, Z at each occurrence are independently selected from C, N, S, SO$_2$ and O, which may, wherever possible be optionally substituted;

each of $R^6$, $R^7$, $R^8$, $R^9$, $R^{10}$ and $R^{11}$ at each occurrence are independently selected from hydrogen, halogen, cyano, amide, sulphonamide, acyl, hydroxyl, and optionally substituted groups selected from $(C_1-C_6)$alkyl, $(C_1-C_6)$haloalkyl, $(C_3-C_6)$cycloalkyl, $(C_1-C_6)$alkoxy, benzyl, aryl, heteroaryl, and heterocyclyl; alternatively each of $R^7$ and $R^8$, $R^8$ and $R^9$, $R^9$ and $R^{10}$ or $R^{10}$ and $R^{11}$ wherever possible, together may form a 4 to 7 membered saturated or partially saturated ring containing from 0-2 additional heteroatoms selected from the group consisting of N, O, and S(O)$_p$; and p is 1 or 2.

2. The compound of claim 1, wherein $R^1$ at each occurrence is selected from hydrogen, halogen, haloalkyl, and optionally substituted $(C_1-C_6)$alkyl.

3. The compound of claim 1, wherein $R^2$ at each occurrence is selected from hydrogen, halogen, haloalkyl, and optionally substituted $(C_1-C_6)$alkyl.

4. The compound of claim 1, wherein $R^3$ and $R^4$ at each occurrence are independently selected from hydrogen, halogen, haloalkyl, and optionally substituted $(C_1-C_6)$alkyl.

5. The compound of claim 1, wherein each of $R^6$, $R^7$, $R^8$, $R^9$, $R^{10}$ and $R^{11}$ at each occurrence are independently selected from hydrogen, halogen, and optionally substituted groups selected from $(C_1-C_6)$alkyl and $(C_1-C_6)$haloalkyl.

6. The compound of claim 1, wherein when any of the optionally substituted groups is substituted, the substituents are selected from hydrogen, hydroxy, cyano, halo, haloalkyl, haloalkyloxy, alkylthio $(C_1-C_6)$alkyl, $(C_2-C_6)$alkenyl, $(C_2-C_6)$alkynyl, $(C_3-C_7)$cycloalkyl, $(C_1-C_6)$alkoxy, aryl, heterocyclyl, heteroaryl, —$COR_{12}$, —$CSR_{12}$, $C(O)OR_{12}$, $C(O)$—$R_{12}$, —$C(O)$—$NR_{12}R_{13}$, —$C(S)$—$NR_{12}R_{13}$, and —$SO_2R_{12}$, wherein each of $R_{12}$ and $R_{13}$ is independently selected from hydrogen and an optionally substituted group selected from $(C_1-C_6)$alkyl, $(C_2-C_6)$alkenyl, $(C_2-C_6)$alkynyl, $(C_3-C_7)$cycloalkyl, aryl, heteroaryl, and heterocyclyl.

7. The compound of claim 1 selected from the group consisting of:
(R,E)-2-(1-ethylpyrrolidin-2-yl)-N-((1,2,3,5,6,7-hexahydro-s-indacen-4-yl)carbamoyl)-ethanesulfonamide;
(S,E)-2-(1-ethylpyrrolidin-2-yl)-N-((1,2,3,5,6,7-hexahydro-s-indacen-4-yl)carbamoyl)-ethanesulfonamide;
(R,E)-N-((1,2,3,5,6,7-hexahydro-s-indacen-4-yl)carbamoyl)-2-(pyrrolidin-2-yl)ethene-1-sulfonamide;
(R,E)-N-((1,2,3,5,6,7-hexahydro-s-indacen-4-yl)carbamoyl)-2-(1-propylpyrrolidin-2-yl)ethene-1-sulfonamide;
(R,E)-2-(1-(cyclopropylmethyl)pyrrolidin-2-yl)-N-((1,2,3,5,6,7-hexahydro-s-indacen-4-yl)carbamoyl)ethene-1-sulfonamide;
(R,E)-N-((1,2,3,5,6,7-hexahydro-s-indacen-4-yl)carbamoyl)-2-(1-methylpyrrolidin-2-yl)ethene-1-sulfonamide;
(R,E)-N-((1,2,3,5,6,7-hexahydro-s-indacen-4-yl)carbamoyl)-2-(1-(methylsulfonyl)-pyrrolidin-2-yl)ethene-1-sulfonamide;
(R,E)-2-(1-acetylpyrrolidin-2-yl)-N-((1,2,3,5,6,7-hexahydro-s-indacen-4-yl)carbamoyl)-ethene-1-sulfonamide;
(E)-2-(1-benzylpiperidin-4-yl)-N-((1,2,3,5,6,7-hexahydro-s-indacen-4-yl)carbamoyl)-ethanesulfonamide;
tert-butyl(R,E)-2-(2-(N-((1,2,3,5,6,7-hexahydro-s-indacen-4-yl)carbamoyl) sulfamoyl)-vinyl)pyrrolidine-1-carboxylate;
(R,E)-N-((1,2,3,5,6,7-hexahydro-s-indacen-4-yl)carbamoyl)-2-(1-(2-methoxyethyl)pyrrolidin-2-yl)ethenesulfonamide;
(R,E)-N-((1,2,3,5,6,7-hexahydro-s-indacen-4-yl)carbamoyl)-2-(1-(isopropylsulfonyl)pyrrolidin-2-yl)ethenesulfonamide;
(R,E)-2-(1-((3-fluorophenyl)sulfonyl)pyrrolidin-2-yl)-N-((1,2,3,5,6,7-hexahydro-s-indacen-4-yl)carbamoyl)ethenesulfonamide;
(R,E)-N-((1,2,3,5,6,7-hexahydro-s-indacen-4-yl)carbamoyl)-2-(1-(pyrazine-2-carbonyl)pyrrolidin-2-yl)ethenesulfonamide;
(R,E)-2-(2-(N-((1,2,3,5,6,7-hexahydro-s-indacen-4-yl)carbamoyl)sulfamoyl)vinyl)pyrrolidine-1-carboxamide;
(R,E)-2-(1-(cyclopropanecarbonyl)pyrrolidin-2-yl)-N-((1,2,3,5,6,7-hexahydro-s-indacen-4-yl)carbamoyl)ethene-1-sulfonamide;
(R,E)-N-((1,2,3,5,6,7-hexahydro-s-indacen-4-yl)carbamoyl)-2-(1-(2,2,2-trifluoroacetyl)pyrrolidin-2-yl)ethene-1-sulfonamide;
(R,E)-N-((1,2,3,5,6,7-hexahydro-s-indacen-4-yl)carbamoyl)-2-(1-(2-(methylthio)ethyl)pyrrolidin-2-yl)ethene-1-sulfonamide;
(R,E)-N-((1,2,3,5,6,7-hexahydro-s-indacen-4-yl)carbamoyl)-2-(1-(2,2,2-trifluoroethyl)pyrrolidin-2-yl)ethene-1-sulfonamide;
(R,E)-N-((1,2,3,5,6,7-hexahydro-s-indacen-4-yl)carbamoyl)-2-(1-isobutylpyrrolidin-2-yl)ethene-1-sulfonamide;
(R,E)-2-(1-(ethylsulfonyl)pyrrolidin-2-yl)-N-((1,2,3,5,6,7-hexahydro-s-indacen-4-yl)carbamoyl)ethene-1-sulfonamide;
(R,E)-N-((1,2,3,5,6,7-hexahydro-s-indacen-4-yl)carbamoyl)-2-(1-isopropylpyrrolidin-2-yl)ethene-1-sulfonamide;
(R,E)-N-((1,2,3,5,6,7-hexahydro-s-indacen-4-yl)carbamoyl)-2-(1-(3-(methylsulfonyl)propyl)pyrrolidin-2-yl)ethenesulfonamide;
(R,E)-2-(1-benzoylpyrrolidin-2-yl)-N-((1,2,3,5,6,7-hexahydro-s-indacen-4-yl)carbamoyl)ethenesulfonamide;
(R,E)-N-((2-(1-benzoylpyrrolidin-2-yl)vinyl)sulfonyl)-N-((1,2,3,5,6,7-hexahydro-s-indacen-4-yl)carbamoyl)benzamide;
(R,E)-N-((1,2,3,5,6,7-hexahydro-s-indacen-4-yl)carbamoyl)-2-(pyrrolidin-2-yl)ethenesulfonamide;
(R,E)-N-((1,2,3,5,6,7-hexahydro-s-indacen-4-yl)carbamoyl)-2-(1-(thiophene-3-carbonyl)pyrrolidin-2-yl)ethenesulfonamide;
(R,E)-N-((1,2,3,5,6,7-hexahydro-s-indacen-4-yl)carbamoyl)-2-(pyrrolidin-2-yl)ethene-1-sulfonamide methane sulfonate;
(R,E)-N-((1,2,3,5,6,7-hexahydro-s-indacen-4-yl)carbamoyl)-2-(pyrrolidin-2-yl)ethene-1-sulfonamide maleate;
(R,Z)—N-((1,2,3,5,6,7-hexahydro-s-indacen-4-yl)carbamoyl)-2-(pyrrolidin-2-yl)ethene-1-sulfonamide;
(S,E)-N-((1,2,3,5,6,7-hexahydro-s-indacen-4-yl)carbamoyl)-3-(pyrrolidin-2-yl)prop-1-ene-1-sulfonamide;
(R,E)-2-(1-(cyclohexylsulfonyl)pyrrolidin-2-yl)-N-((1,2,3,5,6,7-hexahydro-s-indacen-4-yl)carbamoyl)ethene-1-sulfonamide;
(R,Z)—N-((1,2,3,5,6,7-hexahydro-s-indacen-4-yl)carbamoyl)-2-(1-methylpyrrolidin-2-yl)ethene-1-sulfonamide;
(R,E)-2-(1-(cyclohexylmethyl)pyrrolidin-2-yl)-N-((1,2,3,5,6,7-hexahydro-s-indacen-4-yl)carbamoyl)ethene-1-sulfonamide;
(R,E)-2-(1-cyclohexylpyrrolidin-2-yl)-N-((1,2,3,5,6,7-hexahydro-s-indacen-4-yl)carbamoyl)ethene-1-sulfonamide;
(R,E)-N-((1,2,3,5,6,7-hexahydro-s-indacen-4-yl)carbamoyl)-2-(1-(1-methylpiperidin-4-yl)pyrrolidin-2-yl)ethene-1-sulfonamide;
(R,Z)—N-((1,2,3,5,6,7-hexahydro-s-indacen-4-yl)carbamoyl)-2-(1-isopropylpyrrolidin-2-yl)ethene-1-sulfonamide;
(R,E)-N-((1,2,3,5,6,7-hexahydro-s-indacen-4-yl)carbamoyl)-2-(1-(tetrahydro-2H-pyran-4-yl)pyrrolidin-2-yl)ethene-1-sulfonamide;
(R,E)-N-((1,2,3,5,6,7-hexahydro-s-indacen-4-yl)carbamoyl)-2-(1-(oxetan-3-yl)pyrrolidin-2-yl)ethene-1-sulfonamide;
(R,E)-N-((1,2,3,5,6,7-hexahydro-s-indacen-4-yl)carbamoyl)-2-(1-(tetrahydro-2H-thiopyran-4-yl)pyrrolidin-2-yl)ethene-1-sulfonamide;
(R,E)-N-((1,2,3,5,6,7-hexahydro-s-indacen-4-yl)carbamoyl)-2-(1-(thiazol-2-ylmethyl)pyrrolidin-2-yl)ethene-1-sulfonamide;

(E)-N-((1,2,3,5,6,7-hexahydro-s-indacen-4-yl)carbamoyl)-2-(piperidin-4-yl)ethenesulfonamide;
(E)-N-((1,2,3,5,6,7-hexahydro-s-indacen-4-yl)carbamoyl)-2-(1-methylpiperidin-4-yl)ethenesulfonamide;
(E)-N-((1,2,3,5,6,7-hexahydro-s-indacen-4-yl)carbamoyl)-2-(1-(methylsulfonyl)piperidin-4-yl)ethenesulfonamide;
(E)-2-(1-acetylpiperidin-4-yl)-N-((1,2,3,5,6,7-hexahydro-s-indacen-4-yl)carbamoyl)ethene-sulfonamide;
tert-butyl (E)-4-(2-(N-((1,2,3,5,6,7-hexahydro-s-indacen-4-yl)carbamoyl) sulfamoyl)vinyl)-piperidine-1-carboxylate;
(E)-2-(1-ethylpiperidin-4-yl)-N-((1,2,3,5,6,7-hexahydro-s-indacen-4-yl)carbamoyl)ethene-1-sulfonamide;
(R,E)-2-(1-ethylpyrrolidin-3-yl)-N-((1,2,3,5,6,7-hexahydro-s-indacen-4-yl)carbamoyl)-ethenesulfonamide;
(R,E)-1,1-diethyl-3-(2-(N-((1,2,3,5,6,7-hexahydro-s-indacen-4-yl)carbamoyl)sulfamoyl)-vinyl)pyrrolidin-1-iumbromide;
(E)-N-((1,2,3,5,6,7-hexahydro-s-indacen-4-yl)carbamoyl)-2-(pyrrolidin-3-yl)ethene-sulfonamide;
(R,E)-N-((1,2,3,5,6,7-hexahydro-s-indacen-4-yl)carbamoyl)-2-(2-methylpyrrolidin-2-yl)ethene-1-sulfonamide;
tert-butyl (R,E)-2-(2-(N-((1,2,3,5,6,7-hexahydro-s-indacen-4-yl)carbamoyl) sulfamoyl)vinyl)-2-methylpyrrolidine-1-carboxylate;
(R,E)-2-(1-acetyl-2-methylpyrrolidin-2-yl)-N-((1,2,3,5,6,7-hexahydro-s-indacen-4-yl)carbamoyl)ethene-1-sulfonamide;
(R,E)-1,1-diethyl-2-(2-(N-((1,2,3,5,6,7-hexahydro-s-indacen-4-yl)carbamoyl)sulfamoyl)-vinyl)-2-methylpyrrolidin-1-ium bromide;
(R,E)-N-((1,2,3,5,6,7-hexahydro-s-indacen-4-yl)carbamoyl)-2-(2-methyl-1-(methylsulfonyl)-pyrrolidin-2-yl)ethene-1-sulfonamide;
(R,E)-2-(1,2-dimethylpyrrolidin-2-yl)-N-((1,2,3,5,6,7-hexahydro-s-indacen-4-yl)carbamoyl)ethene-1-sulfonamide;
(R,E)-2-(1-ethyl-2-methylpyrrolidin-2-yl)-N-((1,2,3,5,6,7-hexahydro-s-indacen-4-yl)carbamoyl)ethene-1-sulfonamide;
(R,E)-2-(1-(cyclopropylmethyl)-2-methylpyrrolidin-2-yl)-N-((1,2,3,5,6,7-hexahydro-s-indacen-4-yl)carbamoyl)ethene-1-sulfonamide;
(S,E)-N-((1,2,3,5,6,7-hexahydro-s-indacen-4-yl)carbamoyl)-2-(pyrrolidin-2-yl)ethene-sulfonamide;
(S,E)-N-((1,2,3,5,6,7-hexahydro-s-indacen-4-yl)carbamoyl)-2-(1-methylpyrrolidin-2-yl)ethenesulfonamide;
(S,E)-tert-butyl 2-(2-(N-((1,2,3,5,6,7-hexahydro-s-indacen-4-yl)carbamoyl) sulfamoyl) vinyl)pyrrolidine-1-carboxylate;
(S,E)-2-(1-(cyclopropylmethyl)pyrrolidin-2-yl)-N-((1,2,3,5,6,7-hexahydro-s-indacen-4-yl)carbamoyl)ethenesulfonamide;
(S,E)-N-((1,2,3,5,6,7-hexahydro-s-indacen-4-yl)carbamoyl)-2-(1-(pyridin-3-ylsulfonyl)-pyrrolidin-2-yl)ethenesulfonamide;
(S,E)-N-((2,6-diisopropylphenyl)carbamoyl)-2-(pyrrolidin-2-yl)ethenesulfonamide;
(S,E)-N-((2,6-diisopropylphenyl)carbamoyl)-2-(1-ethylpyrrolidin-2-yl)ethenesulfonamide;
(S,E)-N-((2,6-diisopropylphenyl)carbamoyl)-2-(1-(methylsulfonyl) pyrrolidin-2-yl)ethene-sulfonamide;
(S,E)-N-((2,6-diisopropylphenyl)carbamoyl)-2-(1-methylpyrrolidin-2-yl)ethenesulfonamide;
(S,E)-2-(1-acetylpyrrolidin-2-yl)-N-((2,6-diisopropylphenyl) carbamoyl)ethenesulfonamide;
(S,E)-2-(1-acetylpyrrolidin-2-yl)-N-((1,2,3,5,6,7-hexahydro-s-indacen-4-yl)carbamoyl)-ethenesulfonamide;
(S,E)-N-((1,2,3,5,6,7-hexahydro-s-indacen-4-yl)carbamoyl)-2-(1-(tetrahydro-2H-pyran-4-carbonyl)pyrrolidin-2-yl)ethenesulfonamide;
(E)-N-((1,2,3,5,6,7-hexahydro-s-indacen-4-yl)carbamoyl)-2-(tetrahydro-2H-pyran-4-yl)ethenesulfonamide;
(S,E)-N-((1,2,3,5,6,7-hexahydro-s-indacen-4-yl)carbamoyl)-2-(1-nicotinoylpyrrolidin-2-yl)ethenesulfonamide;
(E)-N-((1,2,3,5,6,7-hexahydro-s-indacen-4-yl)carbamoyl)-2-(tetrahydrofuran-2-yl)ethene-1-sulfonamide;
(S,E)-N-((1,2,3,5,6,7-hexahydro-s-indacen-4-yl)carbamoyl)-2-(1-(thiophen-2-ylmethyl)-pyrrolidin-2-yl)ethene-1-sulfonamide;
tert-butyl(S,E)-2-(2-(N-((4-fluoro-2,6-diisopropylphenyl)carbamoyl) sulfamoyl) vinyl)-pyrrolidine-1-carboxylate;
(S,E)-N-((4-fluoro-2,6-diisopropylphenyl)carbamoyl)-2-(pyrrolidin-2-yl)ethene-1-sulfonamide;
(S,E)-N-((4-fluoro-2,6-diisopropylphenyl)carbamoyl)-2-(1-methylpyrrolidin-2-yl) ethene-1-sulfonamide;
(R,E)-N-((1,2,3,5,6,7-hexahydro-s-indacen-4-yl)carbamoyl)-2-(1-isobutyl-2-methyl-pyrrolidin-2-yl)ethene-1-sulfonamide;
(R,E)-N-((1,2,3,5,6,7-hexahydro-s-indacen-4-yl)carbamoyl)-2-(2-methyl-1-propylpyrrolidin-2-yl)ethene-1-sulfonamide;
(S,E)-N-((1,2,3,5,6,7-hexahydro-s-indacen-4-yl)carbamoyl)-2-(1-(thiazol-2-yl)pyrrolidin-2-yl)ethene-1-sulfonamide;
(E)-N-((1,2,3,5,6,7-hexahydro-s-indacen-4-yl)carbamoyl)-2-(piperidin-3-yl)ethene-sulfonamide;
(E)-2-(1-ethylpiperidin-3-yl)-N-((1,2,3,5,6,7-hexahydro-s-indacen-4-yl)carbamoyl)ethene-sulfonamide;
(E)-tert-butyl 3-(2-(N-((1,2,3,5,6,7-hexahydro-s-indacen-4-yl)carbamoyl) sulfamoyl)vinyl)-piperidine-1-carboxylate;
(E)-N-((1,2,3,5,6,7-hexahydro-s-indacen-4-yl)carbamoyl)-2-(1-(methylsulfonyl) piperidin-3-yl)ethenesulfonamide;
(E)-2-(1-acetylpiperidin-3-yl)-N-((1,2,3,5,6,7-hexahydro-s-indacen-4-yl)carbamoyl)ethene-sulfonamide;
tert-butyl(E)-2-(2-(N-((1,2,3,5,6,7-hexahydro-s-indacen-4-yl)carbamoyl)sulfamoyl)vinyl)-azetidine-1-carboxylate;
(E)-N-((1,2,3,5,6,7-hexahydro-s-indacen-4-yl)carbamoyl)-2-(1-methylazetidin-2-yl)ethene-1-sulfonamide;
(E)-2-(azetidin-2-yl)-N-((1,2,3,5,6,7-hexahydro-s-indacen-4-yl)carbamoyl)ethene-1-sulfonamide;
(R,E)-N-((1,2,3,5,6,7-hexahydro-s-indacen-4-yl)carbamoyl)-2-(1-(tetrahydro-2H-pyran-4-yl)pyrrolidin-2-yl) ethene-1-sulfonamide;
(S,E)-2-(1-((5-chlorothiophen-2-yl)sulfonyl)pyrrolidin-2-yl)-N-((1,2,3,5,6,7-hexahydro-s-indacen-4-yl)carbamoyl)ethenesulfonamide;
(S,E)-2-(1-(benzylsulfonyl)pyrrolidin-2-yl)-N-((1,2,3,5,6,7-hexahydro-s-indacen-4-yl)carbamoyl)ethenesulfonamide;
(S,E)-N-((1,2,3,5,6,7-hexahydro-s-indacen-4-yl)carbamoyl)-2-(1-((4-methoxyphenyl)sulfonyl) pyrrolidin-2-yl)ethenesulfonamide;
(S,E)-N-((1,2,3,5,6,7-hexahydro-s-indacen-4-yl)carbamoyl)-2-(1-((4-fluorophenyl)sulfonyl) pyrrolidin-2-yl) ethenesulfonamide;

(S,E)-2-(1-((2-cyanophenyl)sulfonyl)pyrrolidin-2-yl)-N-((1,2,3,5,6,7-hexahydro-s-indacen-4-yl)carbamoyl) ethenesulfonamide;

(S,E)-2-(1-(cyclohexylsulfonyl)pyrrolidin-2-yl)-N-((1,2,3,5,6,7-hexahydro-s-indacen-4-yl)carbamoyl)ethenesulfonamide;

(S,E)-2-(1-(4-fluorobenzyl)pyrrolidin-2-yl)-N-((1,2,3,5,6,7-hexahydro-s-indacen-4-yl)carbamoyl)ethenesulfonamide;

(S,E)-2-(1-((4-cyanophenyl)sulfonyl)pyrrolidin-2-yl)-N-((1,2,3,5,6,7-hexahydro-s-indacen-4-yl)carbamoyl) ethene-1-sulfonamide;

(S,E)-2-(1-(4-cyanobenzyl)pyrrolidin-2-yl)-N-((1,2,3,5,6,7-hexahydro-s-indacen-4-yl)carbamoyl)ethene-1-sulfonamide;

(S,E)-N-((1,2,3,6,7,8-hexahydro-as-indacen-4-yl)carbamoyl)-2-(pyrrolidin-2-yl)ethene-1-sulfonamide;

(E)-N-((1,2,3,5,6,7-hexahydro-s-indacen-4-yl)carbamoyl)-2-(piperidin-2-yl)ethene-1-sulfonamide;

(E)-N-((1,2,3,5,6,7-hexahydro-s-indacen-4-yl)carbamoyl)-2-(1-methylpiperidin-2-yl)ethene-1-sulfonamide;

(E)-N-((1,2,3,6,7,8-hexahydro-as-indacen-4-yl)carbamoyl)-2-(1-methylpyrrolidin-2-yl)ethene-1-sulfonamide;

(E)-N-((1,2,3,6,7,8-hexahydro-as-indacen-4-yl)carbamoyl)-2-(1-(methylsulfonyl)pyrrolidin-2-yl)ethene-1-sulfonamide;

((E)-N-((1,2,3,5,6,7-hexahydro-s-indacen-4-yl)carbamoyl)-3-(piperidin-2-yl)prop-1-ene-1-sulfonamide;

(S,E)-N-((1,2,3,5,6,7-hexahydro-s-indacen-4-yl)carbamoyl)-2-(2-methylpyrrolidin-2-yl)ethene-1-sulfonamide;

(S,E)-2-(1,2-dimethylpyrrolidin-2-yl)-N-((1,2,3,5,6,7-hexahydro-s-indacen-4-yl)carbamoyl)ethene-1-sulfonamide;

(E)-N-((1,2,3,5,6,7-hexahydro-s-indacen-4-yl)carbamoyl)-2-(indolin-2-yl)ethene-1-sulfonamide;

tert-butyl(E)-2-(2-(N-((1,2,3,5,6,7-hexahydro-s-indacen-4-yl)carbamoyl) sulfamoyl) vinyl)indoline-1-carboxylate;

((S,E)-2-(1-(cyclopropylmethyl)-2-methylpyrrolidin-2-yl)-N-((1,2,3,5,6,7-hexahydro-s-indacen-4-yl)carbamoyl)ethene-1-sulfonamide;

(S,E)-2-(1-(cyclopropylsulfonyl)pyrrolidin-2-yl)-N-((1,2,3,5,6,7-hexahydro-s-indacen-4-yl)carbamoyl)ethene-1-sulfonamide;

tert-butyl (S,E)-2-(2-(N-((1,2,3,5,6,7-hexahydro-s-indacen-4-yl)carbamoyl) sulfamoyl)vinyl)-2-methylpyrrolidine-1-carboxylate;

tert-butyl (R,E)-2-(2-(N-((2,6-diisopropylphenyl)carbamoyl) sulfamoyl) vinyl)-2-methylpyrrolidine-1-carboxylate;

(R,E)-N-((2,6-diisopropylphenyl)carbamoyl)-2-(2-methylpyrrolidin-2-yl)ethane-1-sulfonamide 2,2,2-trifluoroacetate;

(R,E)-N-((2,6-diisopropylphenyl)carbamoyl)-2-(1,2-dimethylpyrrolidin-2-yl)ethene-1-sulfonamide;

(S,E)-2-(1-ethyl-2-methylpyrrolidin-2-yl)-N-((1,2,3,5,6,7-hexahydro-s-indacen-4-yl)carbamoyl)ethene-1-sulfonamide;

Bis sodium (R,E)-((2-(1,2-dimethylpyrrolidin-2-yl)vinyl)sulfonyl)((1,2,3,5,6,7-hexahydro-s-indacen-4-yl)carbamoyl)amide;

Sodium (R,E)-((2-(1,2-dimethylpyrrolidin-2-yl)vinyl)sulfonyl)((1,2,3,5,6,7-hexahydro-s-indacen-4-yl)carbamoyl)amide;

tert-butyl (S,E)-2-(2-(N-((2,6-diisopropylphenyl)carbamoyl)sulfamoyl) vinyl)-2-methylpyrrolidine-1-carboxylate;

(S,E)-N-((2,6-diisopropylphenyl)carbamoyl)-2-(2-methylpyrrolidin-2-yl)ethene-1-sulfonamide 2,2,2-trifluoroacetate;

(S,E)-N-((2,6-diisopropylphenyl)carbamoyl)-2-(1,2-dimethylpyrrolidin-2-yl)ethene-1-sulfonamide;

(R,E)-N-((1,2,3,5,6,7-hexahydro-s-indacen-4-yl)carbamoyl)-2-(2-methyl-1-(oxetan-3-yl)pyrrolidin-2-yl)ethene-1-sulfonamide;

tert-butyl (S,E)-2-(2-(N-((4-fluoro-2,6-diisopropylphenyl)carbamoyl) sulfamoyl)vinyl)-2-methylpyrrolidine-1-carboxylate;

(S,E)-N-((4-fluoro-2,6-diisopropylphenyl)carbamoyl)-2-(2-methylpyrrolidin-2-yl)ethene-1-sulfonamide 2,2,2-trifluoroacetate;

(S,E)-2-(1,2-dimethylpyrrolidin-2-yl)-N-((4-fluoro-2,6-diisopropylphenyl)carbamoyl)ethene-1-sulfonamide;

(E)-2-(1-acetylazetidin-2-yl)-N-((1,2,3,5,6,7-hexahydro-s-indacen-4-yl)carbamoyl)ethene-1-sulfonamide;

tert-butyl (R,E)-(2-(2-(2-(N-((1,2,3,5,6,7-hexahydro-s-indacen-4-yl)carbamoyl)sulfamoyl)vinyl)pyrrolidin-1-yl)ethyl)(methyl)carbamate;

(S,E)-2-(1-allylpyrrolidin-2-yl)-N-((1,2,3,5,6,7-hexahydro-s-indacen-4-yl)carbamoyl)ethene-1-sulfonamide;

(S,E)-2-(1-(1H-benzo[d]imidazole-6-carbonyl)pyrrolidin-2-yl)-N-((1,2,3,5,6,7-hexahydro-s-indacen-4-yl)carbamoyl)ethene-1-sulfonamide;

(S,E)-2-(1-(cyclopropylsulfonyl)-2-methylpyrrolidin-2-yl)-N-((1,2,3,5,6,7-hexahydro-s-indacen-4-yl)carbamoyl)ethene-1-sulfonamide;

(S,E)-N-((1,2,3,5,6,7-hexahydro-s-indacen-4-yl)carbamoyl)-2-(1-(4-methoxybenzyl)pyrrolidin-2-yl)ethene-1-sulfonamide;

tert-butyl 5-((R)-2-((E)-2-(N-((1,2,3,5,6,7-hexahydro-s-indacen-4-yl) carbamoyl)sulfamoyl)vinyl)pyrrolidin-1-yl)hexahydrocyclopenta[c]pyrrole-2(1H)-carboxylate;

(E)-N-((1,2,3,5,6,7-hexahydro-s-indacen-4-yl)carbamoyl)-2-((2R)-1-(octahydrocyclo-penta[c]pyrrol-5-yl)pyrrolidin-2-yl)ethene-1-sulfonamide 2,2,2-trifluoroacetate;

(E)-2-(1-(cyclopropylsulfonyl)azetidin-2-yl)-N-((1,2,3,5,6,7-hexahydro-s-indacen-4-yl)carbamoyl)ethene-1-sulfonamide;

(S,E)-N-((2,6-diisopropylphenyl)carbamoyl)-2-(1-(thiazol-2-yl)pyrrolidin-2-yl)ethene-1-sulfonamide;

tert-butyl (S,E)-2-(2-(2-(N-((1,2,3,5,6,7-hexahydro-s-indacen-4-yl)carbamoyl)sulfamoyl)vinyl)-2-methylpyrrolidin-1-yl)ethyl)(methyl)carbamate;

potassium (R,E)-((2-(1,2-dimethylpyrrolidin-2-yl)vinyl)sulfonyl)((1,2,3,5,6,7-hexahydro-s-indacen-4-yl)carbamoyl)amide;

tert-butyl (E)-(2-(2-(2-(N-((1,2,3,5,6,7-hexahydro-s-indacen-4-yl)carbamoyl)sulfamoyl)vinyl)azetidin-1-yl)ethyl)(methyl)carbamate;

(S,E)-2-(1-(cyclohexylmethyl)-2-methylpyrrolidin-2-yl)-N-((1,2,3,5,6,7-hexahydro-s-indacen-4-yl)carbamoyl)ethene-1-sulfonamide;

Sodium (R,E)-((1,2,3,5,6,7-hexahydro-s-indacen-4-yl)carbamoyl)((2-(1-(tetrahydro-2H-thiopyran-4-yl)pyrrolidin-2-yl)vinyl)sulfonyl)amide;

sodium (R,E)-((2-(1-cyclohexylpyrrolidin-2-yl)vinyl)sulfonyl)((1,2,3,5,6,7-hexahydro-s-indacen-4-yl)carbamoyl)amide;

sodium (S,E)-((2,6-diisopropylphenyl)carbamoyl)((2-(1,2-dimethylpyrrolidin-2-yl)vinyl)sulfonyl)amide;

sodium (R,E)-((1,2,3,5,6,7-hexahydro-s-indacen-4-yl)carbamoyl)((2-(1-methylpyrrolidin-2-yl)vinyl)sulfonyl)amide;
potassium (R,E)-((1,2,3,5,6,7-hexahydro-s-indacen-4-yl)carbamoyl)((2-(1-methylpyrrolidin-2-yl)vinyl)sulfonyl)amide;
sodium (S,E)-((2-(1,2-dimethylpyrrolidin-2-yl)vinyl)sulfonyl)((1,2,3,5,6,7-hexahydro-s-indacen-4-yl)carbamoyl)amide;
sodium (S,E)-((2-(1-ethylpyrrolidin-2-yl)vinyl)sulfonyl)((1,2,3,5,6,7-hexahydro-s-indacen-4-yl)carbamoyl)amide;
(S,E)-N-((1,2,3,5,6,7-hexahydro-s-indacen-4-yl)carbamoyl)-2-(1-(2-hydroxyethyl)pyrrolidin-2-yl)ethene-1-sulfonamide;
tert-butyl (E)-2-(2-(N-((1,2,3,5,6,7-hexahydro-s-indacen-4-yl)carbamoyl)sulfamoyl)vinyl)-2-methylazetidine-1-carboxylate;
(E)-2-(1,2-dimethylazetidin-2-yl)-N-((1,2,3,5,6,7-hexahydro-s-indacen-4-yl)carbamoyl)ethene-1-sulfonamide;
tert-butyl (S,E)-2-ethyl-2-(2-(N-((1,2,3,5,6,7-hexahydro-s-indacen-4-yl)carbamoyl)sulfamoyl)vinyl)pyrrolidine-1-carboxylate;
tert-butyl (S,E)-2-(2-(N-((1,2,3,6,7,8-hexahydro-as-indacen-4-yl)carbamoyl)sulfamoyl)vinyl)-2-methylpyrrolidine-1-carboxylate;
(S,E)-2-(2-ethylpyrrolidin-2-yl)-N-((1,2,3,5,6,7-hexahydro-s-indacen-4-yl)carbamoyl)ethene-1-sulfonamide 2,2,2-trifluoroacetate;
(S,E)-N-((1,2,3,6,7,8-hexahydro-as-indacen-4-yl)carbamoyl)-2-(2-methylpyrrolidin-2-yl)ethene-1-sulfonamide 2,2,2-trifluoroacetate;
(S,E)-2-(1,2-dimethylpyrrolidin-2-yl)-N-((1,2,3,6,7,8-hexahydro-as-indacen-4-yl)carbamoyl)ethene-1-sulfonamide;
tert-butyl (R,E)-2-(2-(N-((1,2,3,6,7,8-hexahydro-as-indacen-4-yl)carbamoyl)sulfamoyl)vinyl)-2-methylpyrrolidine-1-carboxylate;
(R,E)-N-((1,2,3,6,7,8-hexahydro-as-indacen-4-yl)carbamoyl)-2-(2-methylpyrrolidin-2-yl)ethene-1-sulfonamide 2,2,2-trifluoroacetate;
(R,E)-2-(1,2-dimethylpyrrolidin-2-yl)-N-((1,2,3,6,7,8-hexahydro-as-indacen-4-yl)carbamoyl)ethene-1-sulfonamide;
tert-butyl (R,E)-2-(3-(N-((1,2,3,5,6,7-hexahydro-s-indacen-4-yl)carbamoyl)sulfamoyl)allyl)-2-methylpyrrolidine-1-carboxylate;
tert-butyl (R,E)-(2-(2-(3-(N-((1,2,3,5,6,7-hexahydro-s-indacen-4-yl)carbamoyl)sulfamoyl)allyl)-2-methylpyrrolidin-1-yl)ethyl)(methyl)carbamate;
(R,E)-3-(1,2-dimethylpyrrolidin-2-yl)-N-((1,2,3,5,6,7-hexahydro-s-indacen-4-yl)carbamoyl)prop-1-ene-1-sulfonamide;
tert-butyl (S,E)-(3-(2-(2-(N-((1,2,3,5,6,7-hexahydro-s-indacen-4-yl)carbamoyl)sulfamoyl)vinyl)pyrrolidin-1-yl)propyl)(methyl)carbamate;
tert-butyl (E)-(3-(2-(2-(N-((1,2,3,5,6,7-hexahydro-s-indacen-4-yl)carbamoyl)sulfamoyl)vinyl)-2-methylazetidin-1-yl)propyl)(methyl)carbamate;
tert-butyl (E)-(2-(2-(2-(N-((1,2,3,5,6,7-hexahydro-s-indacen-4-yl)carbamoyl)sulfamoyl)vinyl)-2-methylazetidin-1-yl)ethyl)(methyl)carbamate;
(E)-N-((1,2,3,5,6,7-hexahydro-s-indacen-4-yl)carbamoyl)-2-(2-methyl-1-(2-(methylthio)ethyl)azetidin-2-yl)ethene-1-sulfonamide;
(E)-N-((1,2,3,5,6,7-hexahydro-s-indacen-4-yl)carbamoyl)-2-(2-methyl-1-(oxetan-3-yl)azetidin-2-yl)ethene-1-sulfonamide;
tert-butyl (S)-2-(((S)-2-((E)-2-(N-((1,2,3,5,6,7-hexahydro-s-indacen-4-yl)carbamoyl)sulfamoyl)vinyl)-2-methylazetidin-1-yl)methyl)-2-methylpyrrolidine-1-carboxylate;
tert-butyl (S)-2-(((R)-2-((E)-2-(N-((1,2,3,5,6,7-hexahydro-s-indacen-4-yl)carbamoyl)sulfamoyl)vinyl)-2-methylazetidin-1-yl)methyl)-2-methylpyrrolidine-1-carboxylate;
(R,E)-N-((1,2,3,5,6,7-hexahydro-s-indacen-4-yl)carbamoyl)-2-(1-(2-sulfamoylethyl)pyrrolidin-2-yl)ethene-1-sulfonamide;
(S,E)-2-(2-ethyl-1-methylpyrrolidin-2-yl)-N-((1,2,3,5,6,7-hexahydro-s-indacen-4-yl)carbamoyl)ethene-1-sulfonamide; and
(R,E)-2-(1-(but-2-yn-1-yl)pyrrolidin-2-yl)-N-((1,2,3,5,6,7-hexahydro-s-indacen-4-yl)carbamoyl)ethene-1-sulfonamide.

8. A pharmaceutical composition comprising a therapeutically effective amount of a compound of claim 1 and one or more pharmaceutically acceptable carriers, diluents or excipients.

9. A method of treating a disease or condition mediated by NLRP3 modulators, interleukin 1β activity, or interleukin-18 (IL-18) activity in a patient in need thereof, the method comprising administering to the patient an effective amount of a compound of claim 1.

10. The method of claim 9, wherein the NLRP3 modulator has a pathophysiological function.

11. The pharmaceutical composition of claim 8 in combination with one or more suitable pharmaceutically active agents selected from inhibitors of interleukin-1β; immunesuppressants; metabolic disorders drugs, glucocorticoids, non-steroidal anti-inflammatory drugs, COX-2 specific inhibitors, anti-inflammatory drugs, TNF-α binding proteins, interferon-13, interferon, interleukin-2, antihistamines, beta-agonist, BTK inhibitors, anticolinergics, anticancer agents or their suitable pharmaceutically acceptable salts, non-alcoholic steato-hepatitis (NASH) and fibrosis drugs, anticancer drugs, antibiotics, hormones, aromatase inhibitors, inhibitors of mitogen-activated protein kinase signaling, Syk inhibitors, mTOR inhibitors, and BCR/ABL antagonists.

12. A process for the preparation of a compound of claim 1, comprising the following steps:
(i) reacting compound of formula (5) with DMSO where all substituents are as defined in claim 1 to obtain compound of formula (6)

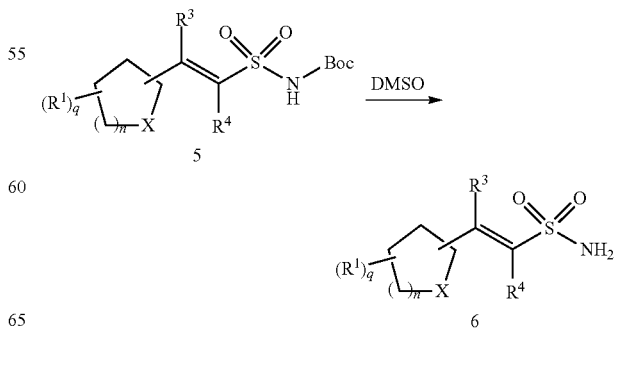

(ii) reacting compound of formula (6) with isocyanato derivative of compound of formula (7) where all substituents are as defined in claim 1 to obtain compound of formula (I)

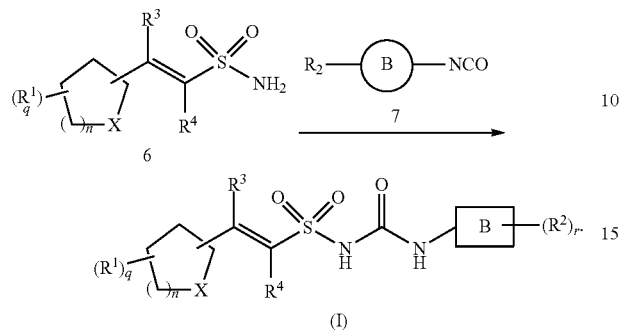

13. A process for the preparation of a compound of claim 1, comprising the following steps:
(a) (i) reacting compound of formula (12) with compound of formula (3) where all substituents are as defined in claim 1 to obtain compound of formula (13)

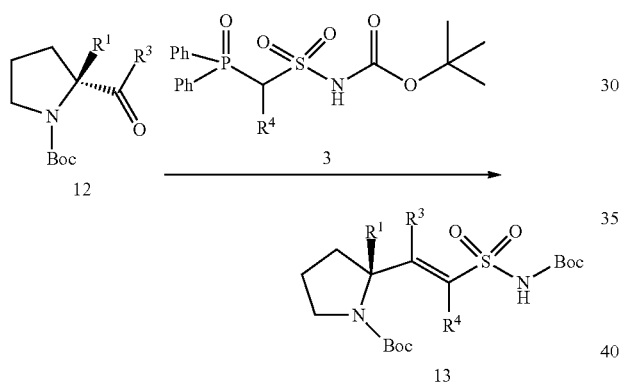

(ii) reacting compound of formula (13) with DMSO where all substituents are as defined in claim 1 to obtain compound of formula (14)

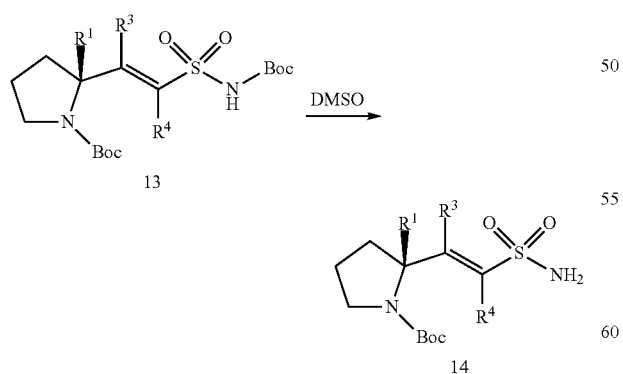

(iii) reacting compound of formula (14) with isocyanato derivative of compound of formula (7) where all substituents are as defined in claim 1 to obtain compound of formula (I)

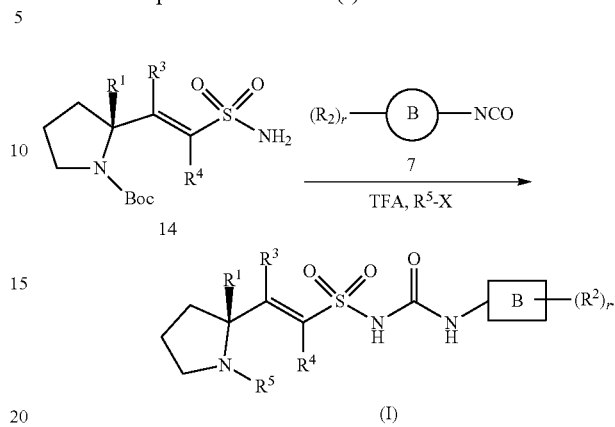

(b) (i) reacting compound of formula (15) with isocyanato derivative of compound of formula (7) where all substituents are as defined in claim 1 to obtain compound of formula (16)

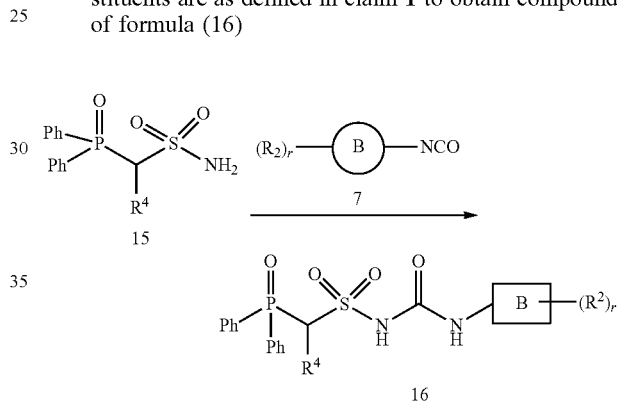

(ii) reacting compound of formula (16) with the compound of formula (4) where all substituents are as defined in claim 1 to obtain compound of formula (I)

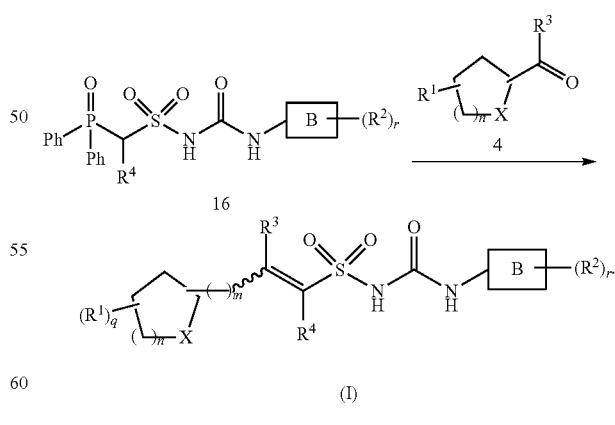

\* \* \* \* \*

UNITED STATES PATENT AND TRADEMARK OFFICE
CERTIFICATE OF CORRECTION

| | | |
|---|---|---|
| PATENT NO. | : 12,084,416 B2 | Page 1 of 1 |
| APPLICATION NO. | : 17/422500 | |
| DATED | : September 10, 2024 | |
| INVENTOR(S) | : Sharma et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 417 days.

Signed and Sealed this
Twelfth Day of August, 2025

Coke Morgan Stewart
*Acting Director of the United States Patent and Trademark Office*